US011459306B2

(12) United States Patent
Landry et al.

(10) Patent No.: US 11,459,306 B2
(45) Date of Patent: Oct. 4, 2022

(54) COMPOUNDS, COMPOSITIONS, AND METHODS FOR TREATING T-CELL ACUTE LYMPHOBLASTIC LEUKEMIA

(71) Applicant: The Trustees of Columbia University in the City of New York, New York, NY (US)

(72) Inventors: Donald W. Landry, New York, NY (US); Shi-Xian Deng, White Plains, NY (US); Xiaoming Xu, Fair Lawn, NJ (US); Thomas Diacovo, Larchmont, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 81 days.

(21) Appl. No.: 16/633,074

(22) PCT Filed: Jul. 31, 2018

(86) PCT No.: PCT/US2018/044659
§ 371 (c)(1),
(2) Date: Jan. 22, 2020

(87) PCT Pub. No.: WO2019/028055
PCT Pub. Date: Feb. 7, 2019

(65) Prior Publication Data
US 2020/0165211 A1 May 28, 2020

Related U.S. Application Data

(60) Provisional application No. 62/539,012, filed on Jul. 31, 2017.

(51) Int. Cl.
| | |
|---|---|
| *C07D 403/12* | (2006.01) |
| *C07D 239/90* | (2006.01) |
| *A61P 35/00* | (2006.01) |
| *A61K 31/506* | (2006.01) |
| *A61K 31/517* | (2006.01) |
| *A61K 31/52* | (2006.01) |
| *A61K 31/573* | (2006.01) |
| *C07D 401/12* | (2006.01) |
| *C07D 403/14* | (2006.01) |
| *C07D 473/16* | (2006.01) |

(52) U.S. Cl.
CPC .......... *C07D 239/90* (2013.01); *A61K 31/506* (2013.01); *A61K 31/517* (2013.01); *A61K 31/52* (2013.01); *A61K 31/573* (2013.01); *A61P 35/00* (2018.01); *C07D 401/12* (2013.01); *C07D 403/14* (2013.01); *C07D 473/16* (2013.01)

(58) Field of Classification Search
CPC ... C07D 401/12; C07D 403/12; C07D 473/16
USPC ...... 544/272, 324; 514/263.21, 263, 22, 275
See application file for complete search history.

(56) References Cited

U.S. PATENT DOCUMENTS

| | | | |
|---|---|---|---|
| 5,034,506 | A | 7/1991 | Summerton et al. |
| 5,235,033 | A | 8/1993 | Summerton et al. |
| 5,270,163 | A | 12/1993 | Gold et al. |
| 6,632,789 | B1 | 10/2003 | June |
| 7,642,348 | B2 | 1/2010 | Bentwich et al. |
| 7,825,229 | B2 | 11/2010 | Itzhak et al. |
| 7,888,352 | B2 | 2/2011 | Bayliss et al. |

(Continued)

FOREIGN PATENT DOCUMENTS

| | | | | |
|---|---|---|---|---|
| WO | WO 2001081346 | * 11/2001 | ........... C07D 473/00 |
| WO | 2005113556 A1 | 12/2005 | |

(Continued)

OTHER PUBLICATIONS

International Preliminary Report on Patentability dated Feb. 13, 2020 issued in PCT/US2018/044659.
International Search Report and Written Opinion issued in application No. PCT/US2018/044659, dated Sep. 20, 2018.
Cante-Barrett et al., "MEK and PI3K-AKT inhibitors synergistically block activated IL& receptor signaling in T-cell acute lymphoblastic leukemia", Leukemia, Advanced online publication, May 2016, pp. 1832-1843.
Diacovo, "Elucidating and Targeting Non-classical Oncogenes for Therapy in T-ALL", Cancer Cell Article, Global Technology Community—Protein Kinases and Drug Design, Nov. 2012, pp. 459-472.

(Continued)

*Primary Examiner* — Jeffrey H Murray
(74) *Attorney, Agent, or Firm* — Potomac Law Group, PLLC

(57) ABSTRACT

In an aspect, the disclosure provides for compounds (II), compositions, and methods of administering the compounds and compositions to a patient in need thereof. In another aspect, the disclosure relates to compounds and compositions for treating cancer, for example, lymphoid leukemia. The disclosure further provides for compounds which inhibit two phosphoinositide 3-kinase (PI3K) isoforms, γ and δ, pharmaceutical compositions comprising said compounds, and methods of using said compounds and pharmaceutical compositions for treatment, amelioration, and/or prevention of non-Hodgkin lymphoma.

28 Claims, 25 Drawing Sheets

(56) References Cited

U.S. PATENT DOCUMENTS

| | | | |
|---|---|---|---|
| 8,785,470 B2* | 7/2014 | Castro | A61K 31/517 514/283 |
| 2002/0115080 A1 | 8/2002 | Skouv et al. | |
| 2002/0161014 A1* | 10/2002 | Sadhu | A61P 35/00 514/266.2 |
| 2005/0107325 A1 | 5/2005 | Manoharan et al. | |
| 2005/0182005 A1 | 8/2005 | Tuschl et al. | |
| 2006/0106038 A1 | 5/2006 | Bouscary et al. | |
| 2007/0010548 A1 | 1/2007 | Drees et al. | |
| 2009/0093026 A1 | 4/2009 | Dowdy et al. | |
| 2011/0223619 A1 | 9/2011 | Belvin et al. | |
| 2013/0071323 A1 | 3/2013 | Gallatin et al. | |
| 2014/0213630 A1 | 7/2014 | Diacovo | |

FOREIGN PATENT DOCUMENTS

| | | | |
|---|---|---|---|
| WO | 2005116250 A2 | 12/2005 | |
| WO | 2006126040 A1 | 11/2006 | |
| WO | 2010057048 A1 | 5/2010 | |
| WO | 2011008302 A1 | 1/2011 | |
| WO | 2013082540 A1 | 6/2013 | |
| WO | 2014071109 A1 | 5/2014 | |
| WO | 2014100767 A1 | 6/2014 | |
| WO | WO 2014100767 * | 6/2014 | ........... C07D 403/12 |
| WO | 2015200352 A1 | 12/2015 | |

OTHER PUBLICATIONS

Gutierrez et al., "High frequency of PTEN, PI3K, and AKT abnormalities in T-cell acute lymphoblastic leukemia", Blood, Jul. 2009, vol. 114, No. 3, pp. 647-650.

Krutzfeldt et al., "Silencing of microRNAs in vivo with 'antagomirs'," Letters, Dec. 2005, vol. 438, pp. 685-689, Nature Publishing Group.

Lonetti et al., "PI3K pan-inhibition impairs more efficiently proliferation and survival of T-cell acute lymphoblastic eukemia cell lines when compared to isoform-selective PI3K inhibitors". Oncotarget. vol. 6/Issue 12, pp. 10399-10414, Apr. 2015.

NIH Grant# 5R01CA164346-04; Awardee Organization: University of Texas MD Anderson Cancer Center, "Characterization and targeted therapy of T-ALL deficient for PTEN and INK4A/AFf" PI: You.

Pereira et al., "Molecular effects of the phosphatidylinositol-3-kinase inhibitor NVP-BKM120 on T and B-cell acute lymphoblastic leukaemia". European Journal of Cancer, vol. 41/Issue 14, pp. 2076-2085, Sep. 2015.

Salmena et al., "Tenets of PTEN tumor suppression", Cell, May 2008, vol. 133, pp. 403-414.

Soutschek, et al., Therapeutic silencing of an endogenous gene by systemic administration of modified siRNAs, Nature, Nov. 2004, vol. 432, pp. 173-178, Nature Publishing Group.

Subramaniam et al., "Targeting Nonclassical Oncogenes for Therapy in T-All", Cancer Cell, vol. 21/Issue 4, pp. 459-472, Apr. 2012.

Wheler et al., "Presence of both alterations in FGFR/FGF and PI3K/AKT/mTor confer improved outcomes for patients with metastatic breast cancer treated with PI3K/AKT/mTOR inhibitors", Onoscience, vol. 3/Issue 5-6, pp. 164-172, Jun. 2016.

CAL-130 (Racemate) I C23H22N8O—PubChem (downloaded from https://pubchem.ncbi.nlm.nih.gov/compound/CAL-130-_Racemate on May 14, 2020).

NIH Grant#: 4R01CA169162-05 Awardee Organization: Columbia University Health Sciences Targeting non-classical oncogenes as therapy for T-ALL PI: Diacovo, Apr. 21, 2016.

NIH Grant #: 5K08CA184418-02 Awardee Organization: Children's Hospital of Philadelphia "PI3K pathway inhibition for Philadelphia-like acute lymphoblastic leukemia" PI: Tasian, Jul. 22, 2015.

\* cited by examiner

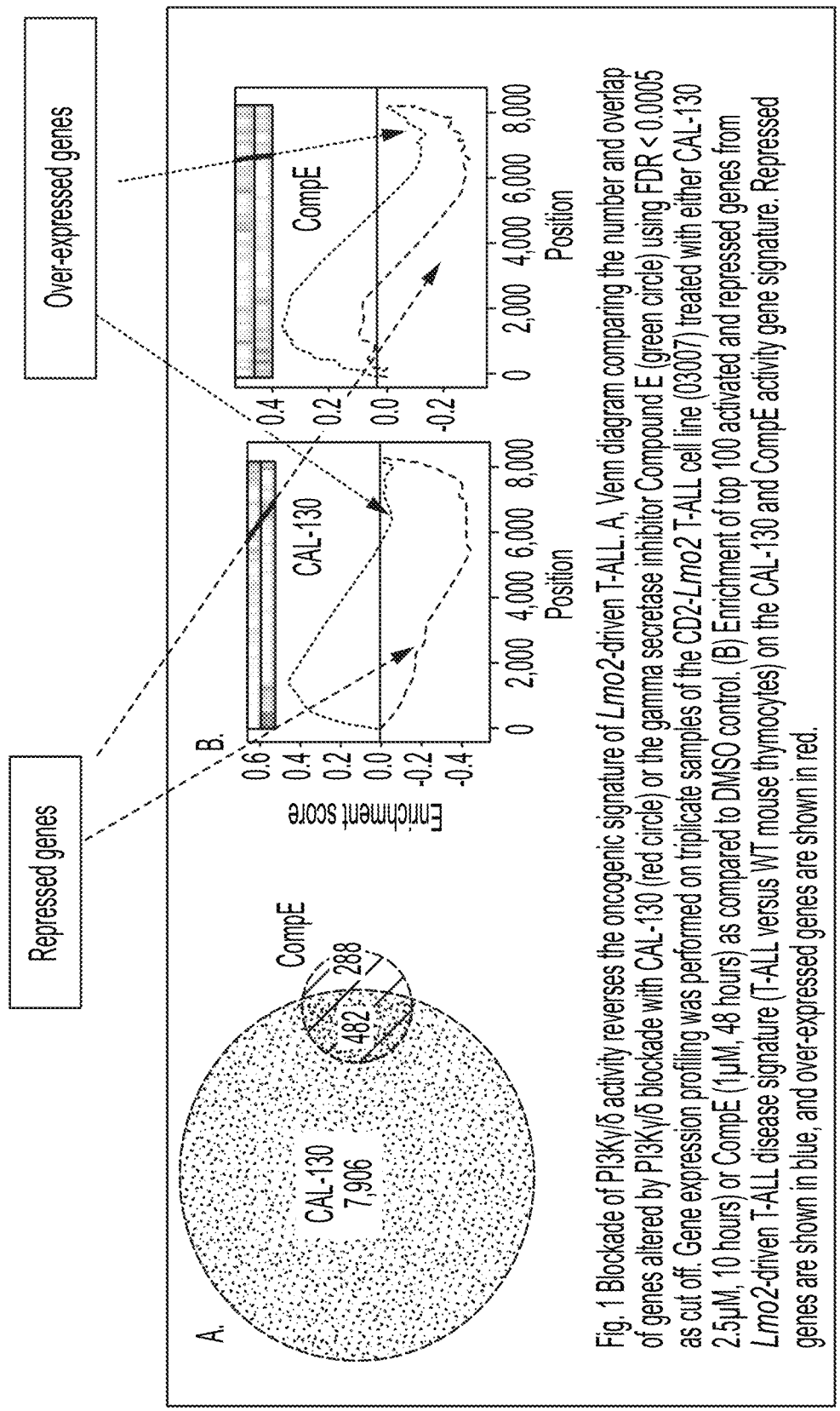

Fig. 1 Blockade of PI3Kγ/δ activity reverses the oncogenic signature of Lmo2-driven T-ALL. A, Venn diagram comparing the number and overlap of genes altered by PI3Kγ/δ blockade with CAL-130 (red circle) or the gamma secretase inhibitor Compound E (green circle) using FDR < 0.0005 as cut off. Gene expression profiling was performed on triplicate samples of the CD2-Lmo2 T-ALL cell line (03007) treated with either CAL-130 2.5μM, 10 hours) or CompE (1μM, 48 hours) as compared to DMSO control. (B) Enrichment of top 100 activated and repressed genes from Lmo2-driven T-ALL disease signature (T-ALL versus WT mouse thymocytes) on the CAL-130 and CompE activity gene signature. Repressed genes are shown in blue, and over-expressed genes are shown in red.

FIG. 1

Fig. 2 Biological assessment of dual PI3K γ/δ inhibitors (A) Plasma concentrations of CAL-130 vs. IPI-145 after administration of a single oral dose to mice. (B) Bioluminescent images of Lck/Pten^fl/fl / Luc with T-ALL immediately before and 4 days after treatment with CAL-130 vs. IPI-145. Blast counts pre/post drug treatments are shown.

A
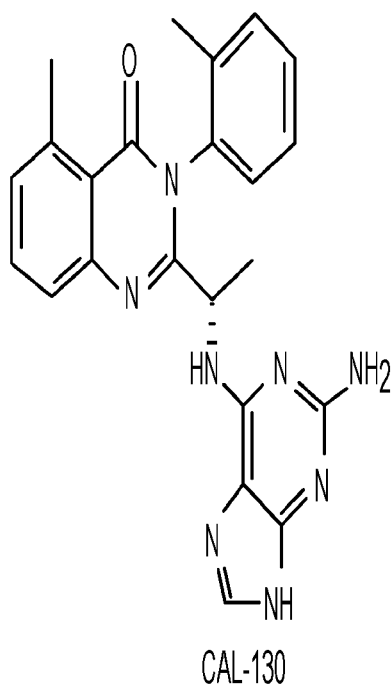
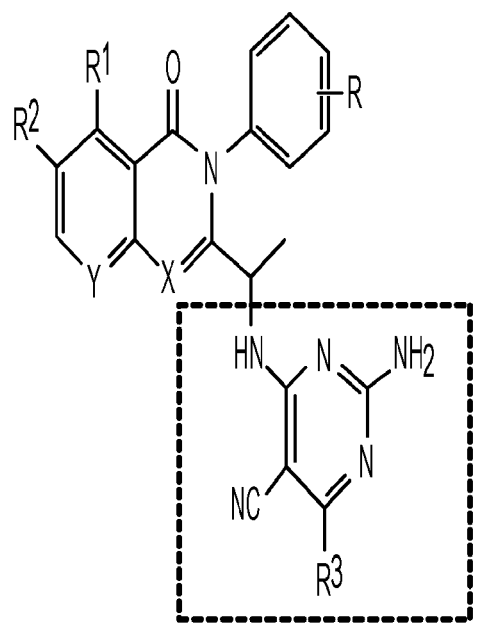
CAL-130
CU-17037
$R^1$ = CH3, Cl, F, N(CH3)2, etc.
$R^2$ = Br, Cl, CH3, X, Y=C or N
$R^3$ = NH2 or CH3
R = H, F, Cl, CH3, etc.
FIG. 4

COMPOUNDS, COMPOSITIONS, AND METHODS FOR TREATING T-CELL ACUTE LYMPHOBLASTIC LEUKEMIA

FIELD

In an aspect, the disclosure provides for compounds, compositions, and methods of administering the compounds and compositions to a patient in need thereof. In another aspect, the disclosure relates to compounds and compositions for treating cancer, for example, lymphoid leukemia or lymphoma. The disclosure further provides for compounds which inhibit two phosphoinositide 3-kinase (PI3K) isoforms, γ and δ, pharmaceutical compositions comprising such compounds, and methods of using the compounds and/or pharmaceutical compositions for treatment, amelioration, and/or prevention of diseases arising from PI3K hyperactivity, such as non-Hodgkin's lymphoma.

BACKGROUND

The PI3K signaling pathway is one of the most highly mutated systems in human cancers. PI3K signaling is also a key factor in many other diseases in humans. PI3K signaling is involved in many disease states including allergic contact dermatitis, rheumatoid arthritis, osteoarthritis, inflammatory bowel diseases, chronic obstructive pulmonary disorder, psoriasis, multiple sclerosis, asthma, disorders related to diabetic complications, and inflammatory complications of the cardiovascular system such as acute coronary syndrome. PI3K/Akt signaling pathway promotes the growth, proliferation and survival of many types of tumors.

PI3Ks exist as heterodimeric complexes, including a p110 catalytic (classified as α, β, γ, or δ) and a p50, p55, p85, or p101 regulatory subunit. PI3Ks can be divided into 2 subclasses, Ia and Ib, defined by mechanism of activation.

Class Ia PI3Ks include the p110α, p110β, and p110δ catalytic domains, each of which associates with a regulatory protein and is activated directly or indirectly on engagement of several cell surface receptors, including TCR.

Class Ib PI3Ks consist only of p110γ, which associates with the p101 adaptor molecule and is primarily stimulated by G protein-coupled receptors.

Initial activation of this pathway, through growth factor interactions with a cell surface receptor for instance, results in the phosphorylation of specific lipids contained within the inner layer of the plasma membrane, yielding the second messenger phosphatidylinositol (3,4,5)-trisphosphate (PIP3). PIP3 then activates key downstream effectors such as PDK-1 and Akt, the latter critical for promoting the biological activities associated class I PI3K.

Once activated, Akt mediates downstream responses—including cell survival, growth, proliferation, migration and angiogenesis—by phosphorylating a range of intracellular proteins. This pathway is present in all cells of higher eukaryotes and is highly conserved.

PTEN is a non-redundant plasma-membrane phosphatase responsible for counteracting the potential cancer-promoting activities of PI3K by limiting the levels of PIP3 generated in response to the activation of these lipid kinases. Mutations in the PTEN tumor suppressor gene are common in multiple types of human cancer. These mutations result in overactive PI3K/Akt signaling and resistance to chemotherapeutic agents). It has been reported that a loss of PTEN function due to mutations has been observed in approximately 40% of primary T-ALL samples. This relationship suggests that hyperactivation of the PI3K/Akt signaling pathway is a common feature of this hematological malignancy.

PTEN is a tumor suppressor gene that normally counteracts the pro-survival effects of PI3K activity, and loss-of-function mutations in PTEN in T-cell progenitors are often associated with T-ALL.

Of the four PI3K isoforms discussed above, two isoforms, gamma (γ) and delta (δ), are sufficient to drive leukemogenesis in T-cell progenitors in the absence of PTEN function.

The delta (δ) isoform of class I PI3K has been implicated, in particular, in a number of diseases and biological processes. PI3K-δ (p110δ) is expressed primarily in hematopoietic cells such as T-cells, dendritic cells, neutrophils, mast cells, B-cells, and macrophages. PI3K-δ is integrally involved in mammalian immune system functions such as T-cell function, B-cell activation, mast cell activation, dendritic cell function, and neutrophil activity. Due to its integral role in immune system function, PI3K-δ is also involved in a number of diseases related to undesirable immune response such as allergic reactions, inflammatory diseases, inflammation mediated angiogenesis, rheumatoid arthritis, and auto-immune diseases such as lupus, asthma, emphysema and other respiratory diseases.

PI3K-γ (p110γ) is expressed primarily in hematopoietic cells and is also involved in inflammation, innate and adaptive immune response, myeloid cell differentiation, immune cell trafficking, and mast cell function. PI3K-γ also plays a role in leukocyte signaling and has been implicated in inflammation, rheumatoid arthritis, and autoimmune diseases such as lupus. Thus, ample evidence exists that the Class I PI3K isoforms p110γ and p110δ have similar biological roles, which may in part rely on their combined activates. This is evidenced by the observation that genetic deletion of either isoform has limited effect on overall T cell development in the thymus, whereas deletion of both p110γ and p110δ results in a severe developmental defect in T cell development.

Additionally, it has been shown through genetic deletion and dual inhibition of both PI3K-γ and PI3K-δ that it is possible to prevent the development as well as disease progression and tumor cell survival in an animal mode of T-cell acute lymphoblastic leukemia (T-ALL).

T-ALL is an aggressive hematologic malignancy that accounts for about 15% of pediatric and about 25% of adult ALL cases. Patients often present with high circulating blast counts and infiltration of the CNS. Despite intensive treatments, 25% of children and adolescents and 50% of adults will fail conventional therapies. Sadly, patients who present with primary resistant disease or relapse T-ALL have a dismal prognosis. Of additional concern for children are the late effects of current treatments including permanent organ damage, reproductive dysfunction, and second cancers. Thus, there remains an urgent need to develop drugs that selectively target key pathways in T-ALL that contribute to tumor maintenance, yet have less toxicity than standard chemotherapies.

The PI3K-AKT signaling pathway is an important mediator of multiple survival and proliferative factors controlling normal T-cell development including IL7 and the pre-TCR signaling. Aberrant activation of the PI3K-AKT pathway in PTEN deficient mice transforms thymocytes into an aggressive T-cell lymphoblastic leukemia. Moreover, mutational loss of PTEN and consequent activation of the PI3K-AKT signaling pathway is present in about 70% of human T-ALL cell lines; of note, >40% of primary T-ALL cases are reported to contain mutations in the PTEN/PI3K/Akt pathway, a figure likely underestimated due the many upstream factors controlling this key oncogenic hub (i.e. via CK2 and RAS).

PI3K inhibitors as a class have not demonstrated promising clinical activity in aggressive lymphomas like diffuse large B cell lymphoma (DLBCL) and peripheral T cell lymphoma (PTCL). Even for the approved indication of follicular lymphoma, the PI3K inhibitors idelalisib and copanlisib are limited by primary (40% of all patients have no response at all) and acquired resistance (all patients develop progression of disease ultimately). PCTL affects more than 7,000 new patients annually in the U.S. Yet the outcome of patients with PTCL remains poor, with long term survival below 15%.

There is a demand for the development of additional PI3K inhibitors for treating T-ALL and other diseases that arise from PI3K hyperactivity. In particular, there is a need for PI3K inhibitors for treating PTCL.

SUMMARY

In an embodiment, the disclosure provides for a compound of formula (I):

(I)

wherein
A represents a fused-on 5- or 6-membered aromatic or heteroaromatic group;
X represents N or CY;
Y represents hydrogen or halogen;
$R^1$, $R^2$, $R^3$, $R^4$, and $R^5$, independently, represent hydrogen, deuterium, $C_1$-$C_6$ alkyl, aryl, heteroaryl, halogen, $NO_2$, or $OCF_3$;
$R^6$ represents $C_1$-$C_6$ alkyl or $C_1$-$C_6$ cycloalkyl;
$R^7$ represents hydrogen, alkyl, or halogen; or
$R^6$ and $R^7$, together with the N to which $R^7$ is attached, form an optionally substituted 5- or 6-membered ring;
$R^8$ represents a heteroaromatic group (such as a pyridine), or a fused-on system (such as purine);
Q represents a direct bond, carbonyl, or alkylene.

In an embodiment, the disclosure provides for a compound of formula (II)

(II)

wherein
X represents N, O, or CY;
Y represents hydrogen or halogen;
$R^1$, $R^2$, $R^3$, $R^4$, and $R^5$, independently, represent hydrogen, deuterium, $C_1$-$C_6$ alkyl, aryl, heteroaryl, halogen, $NO_2$, or $OCF_3$;
$R^6$ represents $C_1$-$C_6$ alkyl or $C_1$-$C_6$ cycloalkyl;
$R^7$ represents hydrogen, alkyl, or halogen; or
$R^6$ and $R^7$, together with the N to which $R^7$ is attached, form an optionally substituted 5- or 6-membered ring;
$R^8$ represents a heteroaromatic group (such as a pyridine), or a fused-on system (such as purine);
$R^9$, $R^{10}$, $R^{11}$, and $R^{12}$, independently, represent hydrogen, $C_1$-$C_6$ alkyl, or halogen;
Q represents a direct bond, carbonyl, or alkylene.

The disclosure provides compounds of formula (IIa) or (IIb)

(IIa)

(IIb)

wherein $R_1$-$R_6$ and $R_9$-$R_{12}$ are as defined in formula (II).
In some embodiments $R^1$, $R^2$, $R^3$, $R^4$, and $R^5$ are independently hydrogen, deuterium, C1-C6 alkyl or halo; $R^6$ is methyl, ethyl, or cyclopropyl; $R^9$ is halo or methyl; and $R^{10}$, $R^{11}$, and $R^{12}$ are each hydrogen, C1-C6 alkyl or halo. For example, in some embodiments, $R^1$, $R^2$, $R^3$, $R^4$, and $R^5$ are independently hydrogen, methyl, F or deuterium; $R^9$ is Cl, F or methyl; and $R^{10}$, $R^{11}$, and $R^{12}$ are each hydrogen. In some examples, the chiral carbon that is bonded to $R^6$ has the stereochemistry shown in formula (IIa') or (IIb'), i.e., the S-enantiomer.

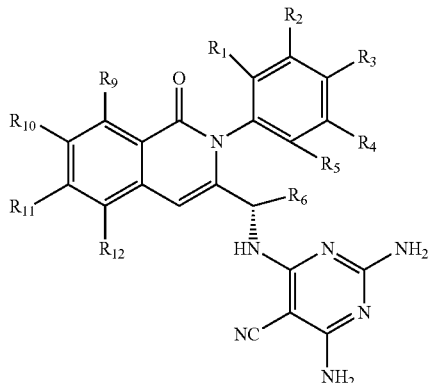

(IIa')

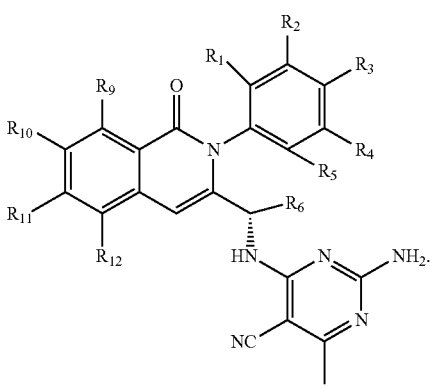

(IIb')

In an embodiment, the disclosure provides for a compound of formula (III)

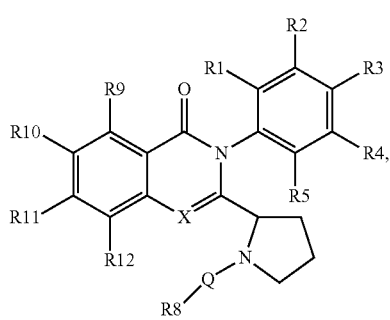

(III)

wherein
X represents N, O, or CY;
Y represents hydrogen or halogen;
$R^1$, $R^2$, $R^3$, $R^4$, and $R^5$, independently, represent hydrogen, deuterium, $C_1$-$C_6$ alkyl, aryl, heteroaryl, halogen, $NO_2$, or $OCF_3$;
$R^8$ represents a heteroaromatic group (such as a pyridine), or a fused-on system (such as purine);
$R^9$, $R^{10}$, $R^{11}$, and $R^{12}$, independently, represent hydrogen, $C_1$-$C_6$ alkyl, or halogen;
Q represents a direct bond, carbonyl, or alkylene.

In an embodiment, the disclosure provides for a compound of the formula (IV):

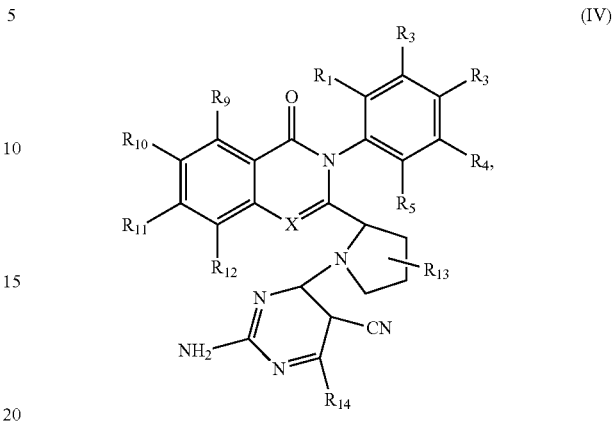

(IV)

wherein
X represents N, O, or CY;
Y represents hydrogen or halogen;
$R^1$, $R^2$, $R^3$, $R^4$, and $R^5$, independently, represent hydrogen, deuterium, $C_1$-$C_6$ alkyl, aryl, heteroaryl, halogen, $NO_2$, or $OCF_3$;
$R^9$, $R^{10}$, $R^{11}$, and $R^{12}$, independently, represent hydrogen, $C_1$-$C_6$ alkyl, or halogen; and
$R^{13}$ represents H, N, or O; and
$R^{14}$ represents $NH_2$ or methyl.

In an embodiment, the disclosure provides for methods of administering a compound described herein to a patient in need thereof. In another aspect, the disclosure provides for methods of treating, preventing, or ameliorating cancer, for example lymphoid leukemia, by administering an effective amount of a compound described herein to a patient or individual in need thereof.

In an embodiment, the disclosure refers to a method for treating, preventing, or ameliorating the effects of a lymphoid malignancy comprising administering to a subject in need thereof an effective amount of a compound described herein. In an aspect, the compound is a phosphoinositide 3-kinase-delta (PI3Kδ) inhibitor and a phosphoinositide 3-kinase-gamma (PI3Kγ) inhibitor.

In an embodiment, a phosphoinositide 3-kinase-delta (PI3Kδ) inhibitor is a compound of any of formulae (I), (II), (III), (IV), Table I, Table II, Table III, compounds Ex. 1-1 to 1-50, compounds Ex. 2-1 to 2-4, and compounds Ex. 3-1 to 3-34 of the disclosure.

The disclosure relates to methods for treating lymphoid cancers, such as lymphomas and leukemias, comprising administering to a subject in need thereof an effective amount of a compound disclosed herein. In particular embodiments, the compound that is administered is a compound of formula (I), (II), (IIa), (IIa'), (IIb) or (IIb'). The lymphoid cancer can be any lymphoma or leukemia, such as acute lymphoblastic leukemia (ALL), T cell acute lymphoblastic leukemia (T-ALL), B cell acute lymphoblastic leukemia (B-ALL), T cell lymphoma, peripheral T cell lymphoma (PTCL), cutaneous T cell lymphoma (CTCL), B cell lymphoma, follicular lymphoma, cutaneous B cell lymphoma, chronic lymphocytic leukemia (CLL) and others disclosed herein. In particular aspects, the disclosure provides a method for treating PTCL, comprising administering to a subject in need thereof an effective amount of a compound disclosed herein. In particular embodiments, the compound that is administered is a compound of formula (I), (II), (IIa), (IIa'), (IIb) or (IIb').

BRIEF DESCRIPTION OF THE FIGURES

FIG. 1A shows that a blockade of PI3Kγ/δ activity reverses the oncogenic signature of T-ALL induced by over expression of the transcription factor oncogene LMO2, which ultimately results in T-ALL by permitting the accumulation of loss of function mutations in PTEN and gain of function mutations in NOTCH1. The effect of the gamma secretase inhibitor compound E ("CompE") that blocks NOTCH1 activity is shown for comparison. FIG. 1B compares the effect of Duvelisib versus CAL-130 on cancerous mice FIG. 2A shows plasma concentrations of CAL-130 vs. IPI-145 (Ex. 1-11 as described herein) after administration of a single oral dose to wild type mice (B6 background). FIG. 2A shows bioluminescent images of Lck/Pten$^{fl/fl}$/Luc with T-ALL immediately before and 4 days after treatment with CAL-130 vs. IPI-145 (Ex. 1-11 as described herein). Blast counts pre/post drug treatment are shown.

FIG. 4A shows chemical structure of compounds of the present disclosure.

DETAILED DESCRIPTION

Figure 2:
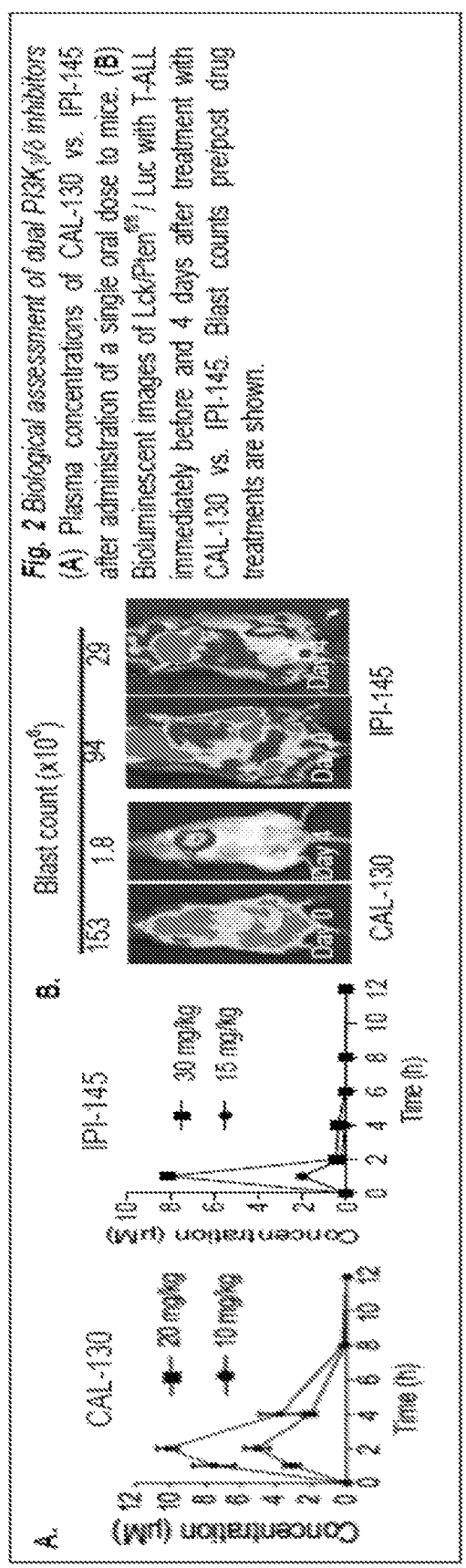
FIGS. 2A-2B show the biological assessment of dual PI3Kγ/δ inhibitors (CAL-130 vs. IPI-145).
Figure 3A:
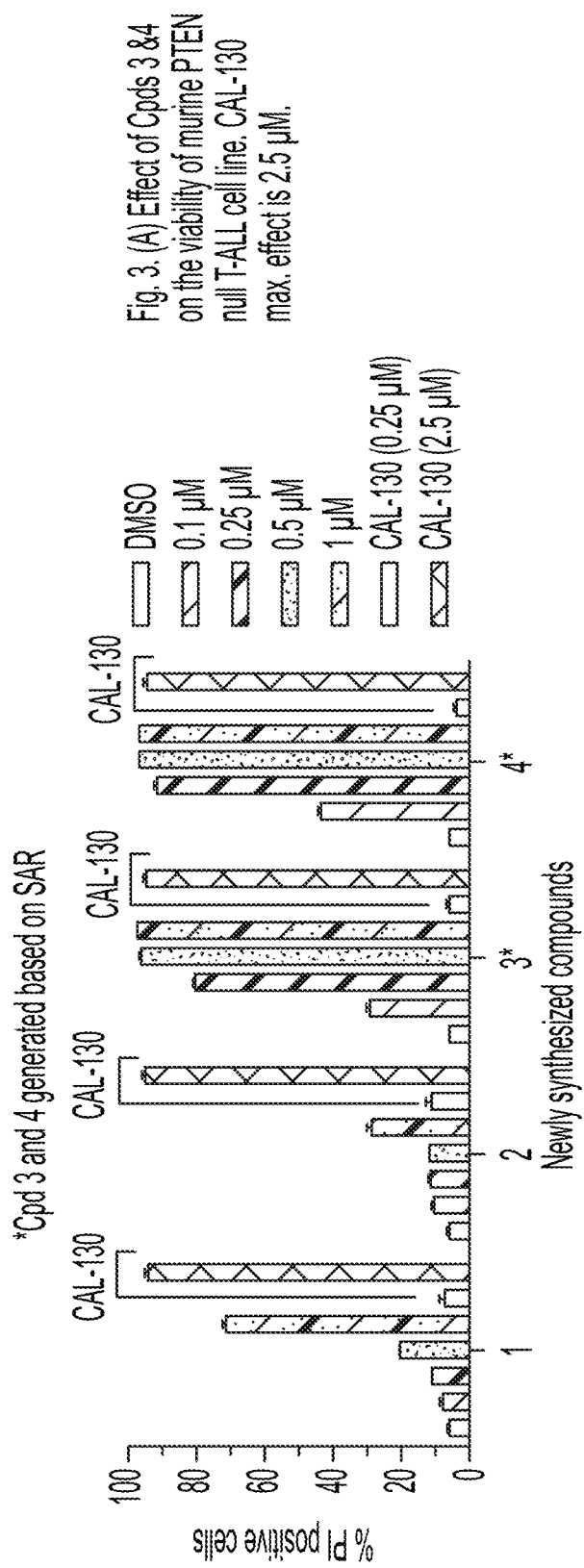
FIG. 3A shows the effect of compounds DWL-PI3K-3 and DWL-PI3K-4 (respectively, Ex. Nos. 1-3 and 1-4 as described herein) on the viability of murine PTEN null/NOTCH 1 activated T-ALL cell line.
Figure 3B:
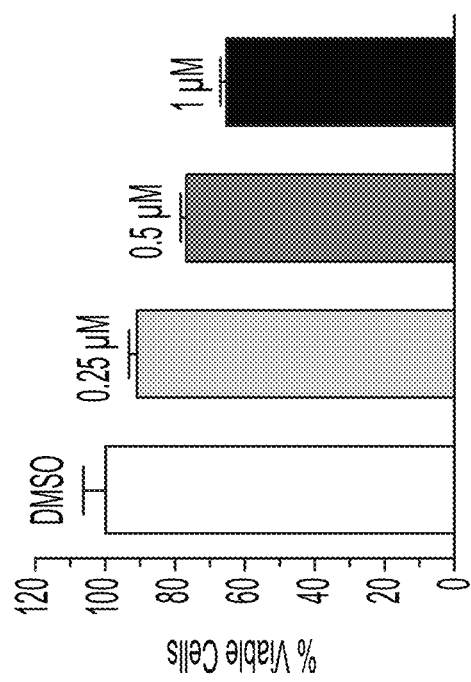
FIG. 3B shows the limited killing of effect of compound DWL-PI3K-4 (Ex. No. 1-4 as described herein) of the disclosure on murine PTEN null T-ALL cell line lacking both p110γ and p110δ catalytic domains.

The disclosure provides for compounds, compositions, and methods of administering a compound or composition described herein to a patient in need thereof. In another aspect, the disclosure provides for methods of treating, preventing, or ameliorating cancer, for example lymphoid leukemia, by administering an effective amount of a compound or composition described herein to a patient or individual in need thereof.

In another embodiment, the disclosure refers to a method for treating, preventing, or ameliorating the effects of a lymphoid malignancy comprising administering to a subject in need thereof an effective amount of a compound or composition described herein. In an aspect, the compound is a phosphoinositide 3-kinase-delta (PI3Kδ) inhibitor and a phosphoinositide 3-kinase-gamma (PI3Kγ) inhibitor. In an embodiment, the lymphoid malignancy is T-cell acute lymphoblastic leukemia (T-ALL) or T-cell acute lymphoblastic lymphoma. In an embodiment, the lymphoid malignancy is T-cell acute lymphoblastic leukemia (T-ALL).

In an embodiment, a compound described herein capable of use in compositions or methods described herein comprises, consists of, or consists essentially of a compound of formulae (I), (II), (III), (IV), Table I, Table II, Table III, and compounds Ex. 1-1 to 1-50, compounds Ex. 2-1 to 2-4, and compounds Ex. 3-1 to 3-34, and combinations thereof. In an aspect, the composition is formulated in a pharmaceutical composition or form. This disclosure includes all forms of the compounds disclosed herein and encompassed by the formulas disclosed herein, including pharmaceutically or physiologically acceptable salt forms (e.g., acid addition salts, base addition salts, hemi-salts), solvates (e.g., hydrates), tautomers (e.g., keto-enol tautomers), all isomeric forms (e.g. R- and S-enantiomers) and racemic mixtures, and compounds in which one or more hydrogen atoms is deuterium.

In an embodiment, the disclosure provides for a compound of formula (I):

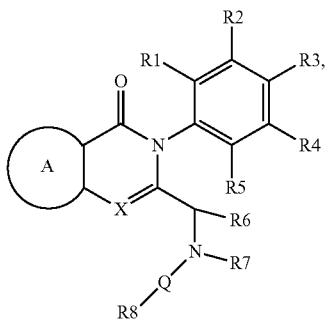

(I)

wherein

A represents a fused-on 5- or 6-membered aromatic or heteroaromatic group;

X represents N, O, or CY;

Y represents hydrogen or halogen;

$R^1$, $R^2$, $R^3$, $R^4$, and $R^5$, independently, represent hydrogen, deuterium, $C_1$-$C_6$ alkyl, aryl, heteroaryl, halogen, $NO_2$, or $OCF_3$;

$R^6$ represents $C_1$-$C_6$ alkyl or $C_1$-$C_6$ cycloalkyl;

$R^7$ represents hydrogen, alkyl, or halogen; or $R^6$ and $R^7$, together with the N to which $R^7$ is attached, form an optionally substituted 5- or 6-membered ring;

$R^8$ represents a heteroaromatic group (such as a pyridine), or a fused-on system (such as purine);

Q represents a direct bond, carbonyl, or alkylene.

In an embodiment, A represents optionally substituted phenyl, aryl, and heteroaryl. In another embodiment, A is selected from the group consisting of optionally substituted phenyl, pyridine, pyrimidine, thiophene. In another embodiment, A represents optionally substituted phenyl.

In an embodiment, the disclosure provides for a compound of formula (II):

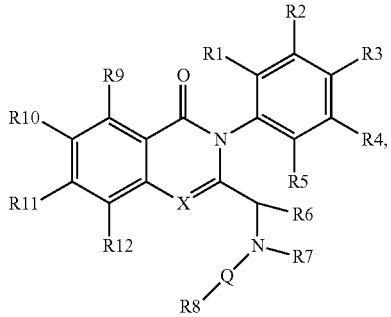

(II)

wherein

X represents N, O, or CY;

Y represents hydrogen or halogen;

$R^1$, $R^2$, $R^3$, $R^4$, and $R^5$, independently, represent hydrogen, deuterium, $C_1$-$C_6$ alkyl, aryl, heteroaryl, halogen, $NO_2$, or $OCF_3$;

$R^6$ represents $C_1$-$C_6$ alkyl or $C_1$-$C_6$ cycloalkyl;

$R^7$ represents hydrogen, alkyl, or halogen; or $R^6$ and $R^7$, together with the N to which $R^7$ is attached, form an optionally substituted 5- or 6-membered ring;

$R^8$ represents a heteroaromatic group (such as a pyridine), or a fused-on system (such as purine);

$R^9$, $R^{10}$, $R^{11}$, and $R^{12}$, independently, represent hydrogen, $C_1$-$C_6$ alkyl, or halogen;

Q represents a direct bond, carbonyl, or alkylene.

In an embodiment, the disclosure provides for a compound of formula (III):

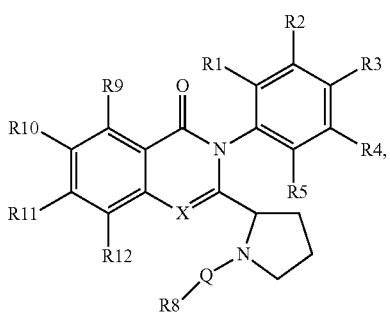

(III)

wherein

X represents N, O, or CY;

Y represents hydrogen or halogen;

$R^1$, $R^2$, $R^3$, $R^4$, and $R^5$, independently, represent hydrogen, deuterium, $C_1$-$C_6$ alkyl, aryl, heteroaryl, halogen, $NO_2$, or $OCF_3$;

$R^8$ represents a heteroaromatic group (such as a pyridine), or a fused-on system (such as purine);

$R^9$, $R^{10}$, $R^{11}$, and $R^{12}$, independently, represent hydrogen, $C_1$-$C_6$ alkyl, or halogen;

Q represents a direct bond, carbonyl, or alkylene.

In an embodiment, the disclosure provides for a compound of formula (IV):

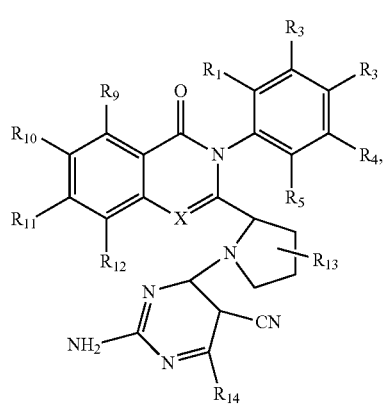

(IV)

wherein

X represents N, O, or CY;

Y represents hydrogen or halogen;

$R^1$, $R^2$, $R^3$, $R^4$, and $R^5$, independently, represent hydrogen, deuterium, $C_1$-$C_6$ alkyl, aryl, heteroaryl, halogen, $NO_2$, or $OCF_3$;

$R^9$, $R^{10}$, $R^{11}$, and $R^{12}$, independently, represent hydrogen, $C_1$-$C_6$ alkyl, or halogen; and $R^{13}$ represents H, N, or O; and (please confirm $R^{13}$)

$R^{14}$ represents $NH_2$ or methyl.

In an embodiment, Y represents hydrogen.

In an embodiment, IV, $R^2$, $R^3$, $R^4$, and $R^5$, independently, represent hydrogen, deuterium, $C_1$-$C_6$ alkyl, or halogen. In another embodiment, IV, $R^2$, $R^3$, $R^4$, and $R^5$, independently, represent hydrogen, deuterium, methyl, fluorine, or chlorine.

In an embodiment, $R^6$ represents $C_1$-$C_6$ alkyl. In another embodiment, $R^6$ represents methyl.

In an embodiment, $R^7$ represents hydrogen.

In an embodiment, $R^6$ and $R^7$, together with the N to which $R^7$ is attached, form an optionally substituted 5-membered ring.

In an embodiment, $R^8$ represents one of the following:

$R^{8a}$
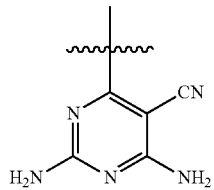

$R^{8b}$
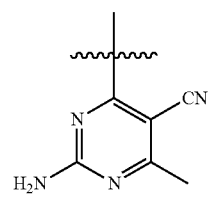

$R^{8c}$
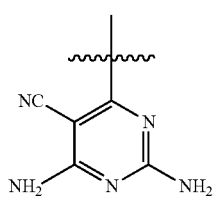 [SMILES: *c1nc(N)nc(N)c1C#N]

$R^{8d}$
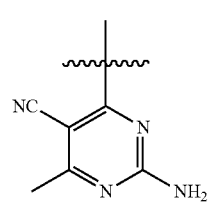

$R^{8e}$
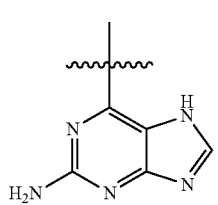

$R^{8f}$
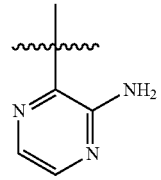

In an embodiment, a compound of formula (I), (II), or (III) does not represent CAL-130.

In an embodiment, the PI3Kδ and PI3Kγ inhibitors according to the disclosure comprise, consist of, or consist essentially of compounds of formula (I).

In another embodiment, the PI3Kδ and PI3Kγ inhibitors according to the disclosure comprise, consist of, or consist essentially of compounds of formula (II).

In another embodiment, the PI3Kδ and PI3Kγ inhibitors according to the present disclosure comprise, consist of, or consist essentially of compounds of formula (III).

In another embodiment, the PI3Kδ and PI3Kγ inhibitors according to the present disclosure comprise, consist of, or consist essentially of compounds of formula (IV).

Table 1 lists additional exemplary compounds of formula (II),

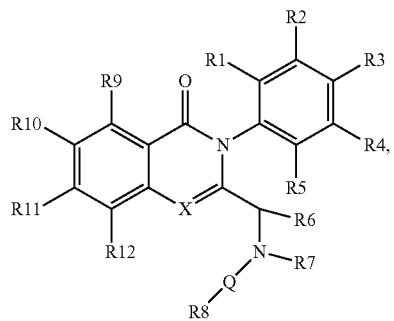

(II)

wherein $R^7$, $R^{10}$, $R^{11}$, and $R^{12}$ are each hydrogen:

Table 1

| Ex. No. | X | Y | Q | $R^1$ | $R^2$ | $R^3$ | $R^4$ | $R^5$ | $R^6$ | $R^8$ | $R^9$ |
|---|---|---|---|---|---|---|---|---|---|---|---|
| 1-1 | N | | Direct bond | Me | H | H | H | H | Me | 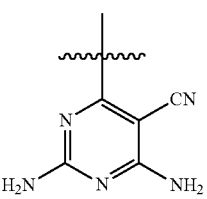 | Me |

Table 1-continued

| Ex. No. | X | Y | Q | R¹ | R² | R³ | R⁴ | R⁵ | R⁶ | R⁸ | R⁹ |
|---|---|---|---|---|---|---|---|---|---|---|---|
| 1-2 | N | | Direct bond | Me | H | H | H | H | Me | 4-methyl-2-amino-5-cyano-pyrimidin-6-yl | Me |
| 1-3 | N | | Direct bond | Me | H | H | H | H | Me | 2,4-diamino-5-cyano-pyrimidin-6-yl | Cl |
| 1-4 | N | | Direct bond | Me | H | H | H | H | Me | 4-methyl-2-amino-5-cyano-pyrimidin-6-yl | Cl |
| 1-5 | N | | Direct bond | H | H | H | H | H | Me | 2,4-diamino-5-cyano-pyrimidin-6-yl | Me |
| 1-6 | CY | H | Direct bond | H | H | H | F | H | cyclopropyl | 2,4-diamino-5-cyano-pyrimidin-6-yl | F |
| 1-7 | CY | H | Direct bond | H | H | H | H | H | Et | 4-methyl-2-amino-5-cyano-pyrimidin-6-yl | Cl |
| 1-8 | CY | H | Direct bond | H | H | H | H | H | Me | 2,4-diamino-5-cyano-pyrimidin-6-yl | Cl |

Table 1-continued
| Ex. No. | X | Y | Q | R¹ | R² | R³ | R⁴ | R⁵ | R⁶ | R⁸ | R⁹ |
|---|---|---|---|---|---|---|---|---|---|---|---|
| 1-9 | CY | H | Direct bond | H | H | H | H | H | Et | 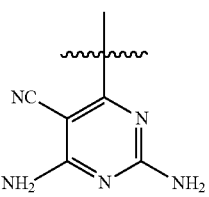 [SMILES: *c1nc(N)nc(N)c1C#N] | Cl |
| 1-10 | CY | H | Direct bond | H | H | H | H | H |  | 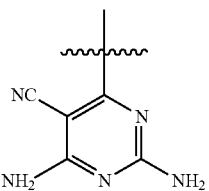 [SMILES: *c1nc(N)nc(N)c1C#N] | Cl |
| 1-11 | CY | H | Direct bond | H | H | H | H | H | Me | 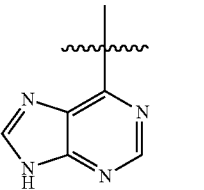 [SMILES: *c1ncnc2[nH]cnc12] | Cl |
| 1-12 | O | | Direct bond | H | H | H | F | H | Et | 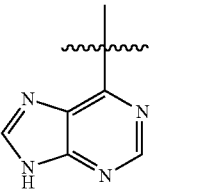 [SMILES: *c1ncnc2[nH]cnc12] | H |
| 1-13 | CY | H | Direct bond | Me | H | H | H | H | Me | 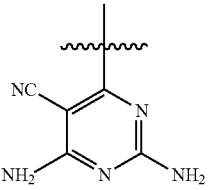 [SMILES: *c1nc(N)nc(N)c1C#N] | Cl |
| 1-14 | CY | H | Direct bond | Me | H | H | H | H | Et | 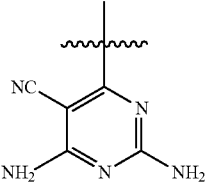 | Cl |
| 1-15 | CY | H | Direct bond | Me | H | H | H | H |  | 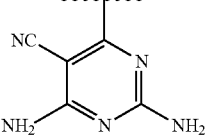 | Cl |

Table 1-continued
| Ex. No. | X | Y | Q | $R^1$ | $R^2$ | $R^3$ | $R^4$ | $R^5$ | $R^6$ | $R^8$ | $R^9$ |
|---|---|---|---|---|---|---|---|---|---|---|---|
| 1-16 | CY | H | Direct bond | H | F | H | F | H | Me | 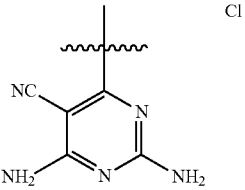 | Cl |
| 1-17 | CY | H | Direct bond | H | F | H | F | H | Et | 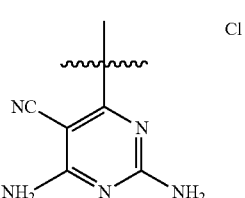 | Cl |
| 1-18 | CY | H | Direct bond | H | F | H | F | H |  | 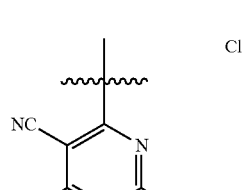 | Cl |
| 1-19 | CY | H | Direct bond | H | H | F | H | H | Me | 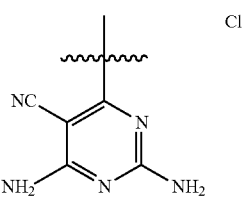 | Cl |
| 1-20 | CY | H | Direct bond | H | H | F | H | H | Et | 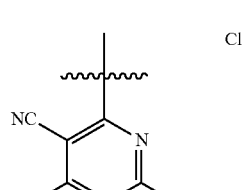 | Cl |
| 1-21 | CY | H | Direct bond | H | H | F | H | H |  | 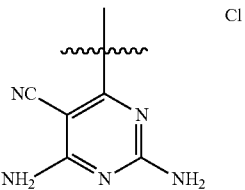 | Cl |
| 1-22 | CY | H | Direct bond | H | H | H | F | H | Me | 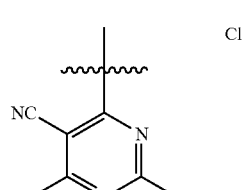 | Cl |

Table 1-continued

| Ex. No. | X | Y | Q | R¹ | R² | R³ | R⁴ | R⁵ | R⁶ | R⁸ | R⁹ |
|---|---|---|---|---|---|---|---|---|---|---|---|
| 1-23 | CY | H | Direct bond | H | H | H | F | H | Et | 2-amino-4-amino-5-cyanopyrimidin-6-yl | Cl |
| 1-24 | CY | H | Direct bond | H | H | H | F | H | cyclopropyl | 2-amino-4-amino-5-cyanopyrimidin-6-yl | Cl |
| 1-25 | CY | H | Direct bond | H | H | H | F | H | Me | 2-amino-4-amino-5-cyanopyrimidin-6-yl | F |
| 1-26 | CY | H | Direct bond | H | H | H | F | H | Et | 2-amino-4-amino-5-cyanopyrimidin-6-yl | F |
| 1-27 | CY | H | Direct bond | H | H | H | H | H | Me | 2-amino-4-amino-5-cyanopyrimidin-6-yl | F |
| 1-28 | CY | H | Direct bond | H | H | H | H | H | Et | 2-amino-4-amino-5-cyanopyrimidin-6-yl | F |
| 1-29 | CY | H | Direct bond | H | H | H | H | H | cyclopropyl | 2-amino-4-amino-5-cyanopyrimidin-6-yl | F |

Table 1-continued
| Ex. No. | X | Y | Q | R¹ | R² | R³ | R⁴ | R⁵ | R⁶ | R⁸ | R⁹ |
|---|---|---|---|---|---|---|---|---|---|---|---|
| 1-30 | CY | H | Direct bond | H | H | H | H | H | Me | 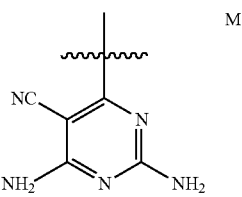 | Me |
| 1-31 | CY | H | Direct bond | H | H | H | H | H | Et | 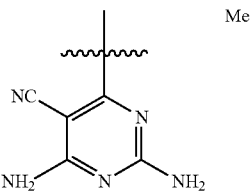 | Me |
| 1-32 | CY | H | Direct bond | H | H | H | H | H |  | 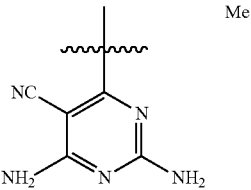 | Me |
| 1-33 | CY | H | Direct bond | Me | H | H | H | H | Me | 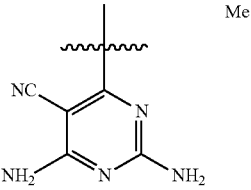 | Me |
| 1-34 | CY | H | Direct bond | Me | H | H | H | H | Et | 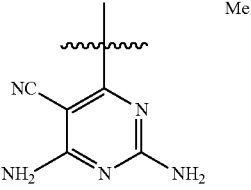 | Me |
| 1-35 | CY | H | Direct bond | Me | H | H | H | H |  | 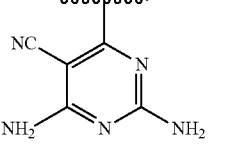 | Me |
| 1-36 | CY | H | Direct bond | H | H | H | H | H | Me | 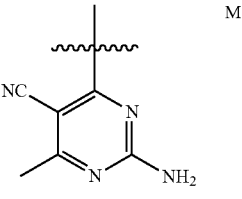 | Me |

Table 1-continued

| Ex. No. | X | Y | Q | R¹ | R² | R³ | R⁴ | R⁵ | R⁶ | R⁸ | R⁹ |
|---|---|---|---|---|---|---|---|---|---|---|---|
| 1-37 | CY | H | Direct bond | Me | H | H | H | H | Me | 2-amino-5-cyano-6-methylpyrimidin-4-yl | Me |
| 1-38 | CY | H | Direct bond | H | H | H | H | H | Me | 2-amino-5-cyano-6-methylpyrimidin-4-yl | F |
| 1-39 | CY | H | Direct bond | Me | H | H | H | H | Me | 2-amino-5-cyano-6-methylpyrimidin-4-yl | F |
| 1-40 | N |   | Direct bond | H | H | H | H | H | Et | 2,4-diamino-5-cyanopyrimidin-6-yl | Cl |
| 1-41 | N |   | Direct bond | Me | H | H | H | H | Me | 2,4-diamino-5-cyanopyrimidin-6-yl | Me |
| 1-42 | N |   | Direct bond | Me | H | H | H | H | Et | 2,4-diamino-5-cyanopyrimidin-6-yl | Me |
| 1-43 | N |   | Direct bond | Me | H | H | H | H | cyclopropyl | 2,4-diamino-5-cyanopyrimidin-6-yl | Me |

Table 1-continued

| Ex. No. | X | Y | Q | R¹ | R² | R³ | R⁴ | R⁵ | R⁶ | R⁸ | R⁹ |
|---|---|---|---|---|---|---|---|---|---|---|---|
| 1-44 | N | | Direct bond | H | H | H | H | H | Me | pyrimidine (NC, NH₂, NH₂) | Me |
| 1-45 | N | | Direct bond | H | H | H | H | H | Et | pyrimidine (NC, NH₂, NH₂) | Me |
| 1-46 | N | | Direct bond | H | H | H | H | H | cyclopropyl | pyrimidine (NC, NH₂, NH₂) | Me |
| 1-47 | N | | Direct bond | H | H | H | H | H | cyclopropyl | pyrimidine (NC, NH₂, NH₂) | Cl |
| 1-48 | N | | Direct bond | Me | H | H | H | H | Me | pyrimidine (NC, Me, NH₂) | Me |
| 1-49 | CY | H | Direct bond | H | F | H | H | H | Me | pyrimidine (NC, NH₂, NH₂) | Cl |
| 1-50 | CY | H | Direct bond | D | D | D | D | D | Me | pyrimidine (NC, NH₂, NH₂) | Cl |

Table 1-continued

| Ex. No. | X | Y | Q | R¹ | R² | R³ | R⁴ | R⁵ | R⁶ | R⁸ | R⁹ |
|---|---|---|---|---|---|---|---|---|---|---|---|
| 1-51 | CY | H | Direct bond | H | H | H | H | H | Me | 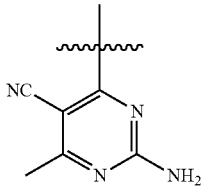 | Cl |

Table 2 lists additional exemplary compounds of formula (III),

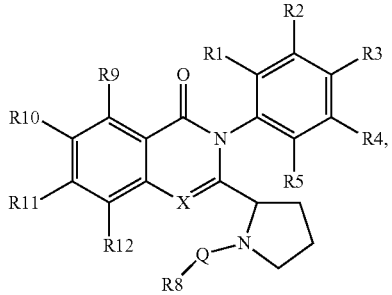

wherein X is N; R9 is F; and R1-R5 and R10-R12 are each hydrogen.

TABLE 2

| Ex. No. | Q | R⁸ |
|---|---|---|
| 2-1 | Direct bond | 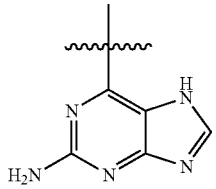 [SMILES: *c1nc(N)nc2nc[nH]c12] |
| 2-2 | carbonyl | 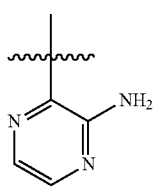 |
| 2-3 | Direct bond | 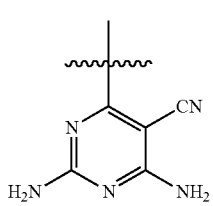 [SMILES: *c1nc(N)nc(N)c1C#N] |//

TABLE 2-continued

| Ex. No. | Q | R⁸ |
|---|---|---|
| 2-4 | Direct bond | 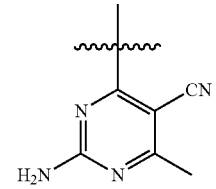 [SMILES: *c1nc(N)nc(C)c1C#N] |

Table 3 lists additional exemplary compounds of formula (IV),

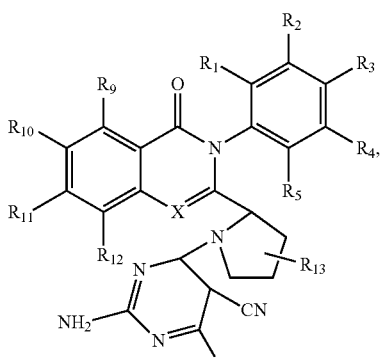

wherein $R^1$-$R^5$ and $R^{10}$-$R^{12}$ are each hydrogen.

TABLE 3

| Ex. No. | X | Y | R⁹ | R¹³ | R¹⁴ |
|---|---|---|---|---|---|
| 3-1 | CY | H | Cl | H | NH₂ |
| 3-2 | CY | H | Cl | N | NH₂ |
| 3-3 | CY | H | Cl | O | NH₂ |
| 3-4 | CY | H | Cl | H | Me |
| 3-5 | CY | H | Cl | N | Me |
| 3-6 | CY | H | Cl | O | Me |
| 3-7 | CY | H | Me | H | NH₂ |
| 3-8 | CY | H | Me | N | NH₂ |
| 3-9 | CY | H | Me | O | NH₂ |
| 3-10 | CY | H | Me | H | Me |
| 3-11 | CY | H | Me | N | Me |
| 3-12 | CY | H | Me | O | Me |
| 3-13 | CY | H | F | H | NH₂ |
| 3-14 | CY | H | F | N | NH₂ |
| 3-15 | CY | H | F | O | NH₂ |
| 3-16 | CY | H | F | H | Me |
| 3-17 | CY | H | F | N | Me |
| 3-18 | CY | H | F | O | Me |

TABLE 3-continued

| Ex. No. | X | Y | R⁹ | R¹³ | R¹⁴ |
|---|---|---|---|---|---|
| 3-19 | N | | Cl | H | NH₂ |
| 3-20 | N | | Cl | N | NH₂ |
| 3-21 | N | | Cl | O | NH₂ |
| 3-22 | N | | Cl | H | Me |
| 3-23 | N | | Cl | N | Me |
| 3-24 | N | | Cl | O | Me |
| 3-25 | N | | Me | H | NH₂ |
| 3-26 | N | | Me | N | NH₂ |
| 3-27 | N | | Me | O | NH₂ |
| 3-28 | N | | Me | H | Me |
| 3-29 | N | | Me | N | Me |
| 3-30 | N | | Me | O | Me |
| 3-31 | N | | F | N | NH₂ |
| 3-32 | N | | F | O | NH₂ |
| 3-33 | N | | F | N | Me |
| 3-34 | N | | F | O | Me |

Any of the compounds above via formulas (I), (II), (III), or (IV) or listed in Tables 1, 2, and 3, or shown as specific compounds, may be the (S) or (R) stereoisomer, with respect to the chiral carbon to which $R^6$ is attached, e.g., in formula (I). Alternatively, any one of the compounds described above may be a non-racemic mixture of (S) and (R) isomers, or the compound may be the (S) isomer alone or the (R) isomer alone.

CAL101, CAL-130, and duvelisib are examples of known PI3K inhibitors, while CU-17037 represents certain embodiments of the present invention:

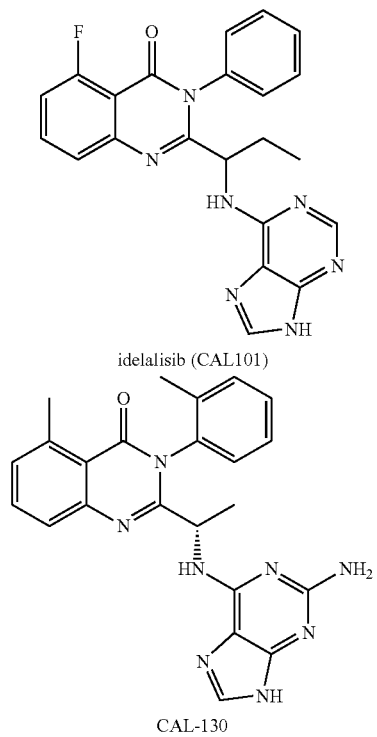

idelalisib (CAL101)

CAL-130

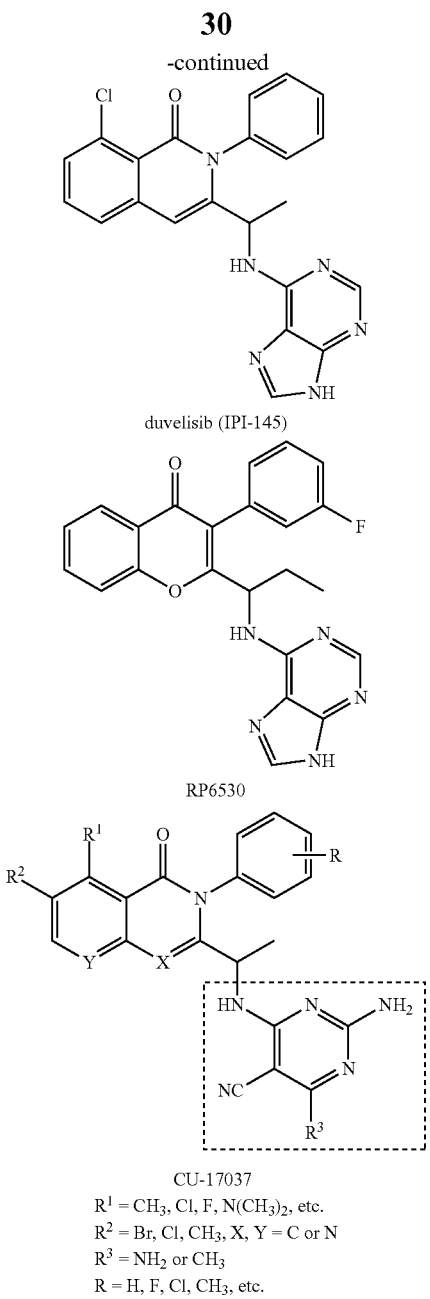

duvelisib (IPI-145)

RP6530

CU-17037
$R^1 = CH_3$, Cl, F, $N(CH_3)_2$, etc.
$R^2 = Br$, Cl, $CH_3$, X, Y = C or N
$R^3 = NH_2$ or $CH_3$
R = H, F, Cl, $CH_3$, etc.

As used herein, "Me" is methyl, "Et" is ethyl, "D" is deuterium.

In an aspect, the disclosure provides for a pharmaceutical composition for treating the effects of a lymphoid malignancy comprising a pharmaceutically acceptable carrier and an effective amount of a phosphoinositide 3-kinase-delta (PI3Kδ) inhibitor and a phosphoinositide 3-kinase-gamma (PI3Kγ) inhibitor.

In an embodiment, the pharmaceutical composition in a unit dosage form. In a further embodiment, the pharmaceutical composition further comprises an effective amount of dexamethasone.

In an embodiment, a method or composition described herein further comprises co-administering to the subject at least one chemotherapeutic agent. In an embodiment, the chemotherapeutic agent is selected from the group consisting of actinomycin, amsacrine, anthracycline, busulfan, cisplatin, cytoxan, epirubicin, hexamethylmelamineoxaliplatin, iphosphamide, mitoxantrone, taxotere, teniposide, triethylenethiophosphoramide, hydrocortisone, cortisone, methylprednisolone, prednisolone, dexamethasone, prednisone, betamethasone, triamcinolone, beclometasone, fludrocortisones, deoxycorticosterone, aldosterone, oxaliplatin, zoledronic acid, ibandronate, verapamil, podophyllotoxin, carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, transplatinum, 5-fluorouracil, vincristin, vinblastin, methotrexate, L-asparaginase, rapamycin, dibenzazepine (DBZ), uramustine, carmustine, lomustine, streptozocin, temozolomide, oxaliplatin, idarubicin, topotecan, premetrexed, 6-mercaptopurine, darcarbazine, fludarabine, 5-fluorouracil, arabinosycytosine, 5-fluorouracil, arabinosylcytosine, capecitabine, gemcitabine, decitabine, vinca alkaloids, paclitaxel (Taxol®), docetaxel (Taxotere®), ixabepilone (Ixempra®), and combinations thereof.

In an embodiment, the chemotherapeutic agent is a glucocorticoid selected from the group consisting of hydrocortisone, cortisone, methylprednisolone, prednisolone, dexamethasone, prednisone, betamethasone, triamcinolone, beclometasone, fludrocortisones, deoxycorticosterone, aldosterone, and combinations thereof.

In an embodiment, the chemotherapeutic agent is dexamethasone.

In an aspect, the disclosure provides for a method for treating, preventing, or ameliorating the effects of a lymphoid malignancy associated with activation of the PI3K/AKT signaling pathway as can occur with a mutated phosphatase and tensin homolog (PTEN) gene or in a subject comprising administering to the subject an effective amount of a phosphoinositide 3-kinase.

In an aspect, the disclosure provides for a method for treating a subject suffering from T-cell acute lymphoblastic leukemia (T-ALL) comprising administering to the subject an effective amount of a pharmaceutical composition comprising a phosphoinositide 3-kinase-delta (PI3Kδ) inhibitor and a phosphoinositide 3-kinase-gamma (PI3Kγ) inhibitor. In an embodiment, the method further comprising administering an effective amount of a glucocorticoid selected from the group consisting of hydrocortisone, cortisone, methylprednisolone, prednisolone, dexamethasone, prednisone, betamethasone, triamcinolone, beclometasone, fludrocortisones, deoxycorticosterone, aldosterone, and combinations thereof. In an embodiment, the glucocorticoid is dexamethasone.

In an aspect, the disclosure provides for a method for lowering tumor burden in a subject suffering from T-cell acute lymphoblastic leukemia (T-ALL) comprising administering to the subject an effective amount of a pharmaceutical composition comprising a compound or composition described herein to a patient in need thereof. In an aspect, the method further comprising administering an effective amount of a glucocorticoid selected from the group consisting of hydrocortisone, cortisone, methylprednisolone, prednisolone, dexamethasone, prednisone, betamethasone, triamcinolone, beclometasone, fludrocortisones, deoxycorticosterone, aldosterone, and combinations thereof. In an embodiment, the glucocorticoid is dexamethasone.

In an aspect, the disclosure provides for a method for identifying a subject who may benefit from co-treatment with a phosphoinositide 3-kinase-delta (PI3Kδ) inhibitor and a phosphoinositide 3-kinase-gamma (PI3Kγ) inhibitor comprising determining from a sample of the subject whether the subject has a mutated PTEN gene and/or activation of PI3K/AKT signaling pathway, wherein the presence of the mutated PTEN gene and/or activation of PI3K/AKT signaling pathway is indicative of a subject who may benefit from co-treatment with a PI3Kδ inhibitor and a PI3Kγ inhibitor.

In an aspect, the disclosure provides for a method for identifying a compound that has both phosphoinositide 3-kinase-delta (PI3Kδ) and phosphoinositide 3-kinase-gamma (PI3Kγ) inhibitory activity comprising:
  (a) contacting a cell with the compound; and
  (b) determining whether the compound modulates an antigen receptor-induced activity in the cell;
  wherein a compound that modulates the antigen receptor-induced activity has both PI3Kδ and PI3Kγ inhibitory activity.

In an aspect, a PI3Kδ inhibitor is an agent that is able to lower the activity level or the expression level of PI3Kδ. Preferably, the PI3Kδ inhibitor has few or no off-target effects; except that it is permissible, in accordance with the present disclosure, to also have an inhibitory effect on PI3Kγ.

Further suitable PI3Kδ inhibitors include, without limitation, AMG-319 (Amgen, Thousand Oaks, Calif.); PI3-delta inhibitors, Cellzome (Cellzome AG, Heidelberg, Germany); PI3-delta/gamma inhibitors, Cellzome (Cellzome AG); CHR-4432 (Chroma Therapeutics, Ltd., Abingdon, UK); XL-499 (Evotech, Hamburg, Germany); CAL-120 (Gilead Sciences, Foster City, Calif.); CAL-129 (Gilead Sciences); CAL-130 (Gilead Sciences); CAL-253 (Gilead Sciences); CAL-263 (Gilead Sciences); GS-1101 (CAL-101) (Gilead Sciences); benzimidazole series, Genentech (Roche Holdings Inc., South San Francisco, Calif.); PI3 kinase delta inhibitors, Genentech (Roche Holdings Inc.); PI3 kinase inhibitor, Roche-4 (Roche Holdings Inc.); PI3 kinase inhibitors, Roche (Roche Holdings Inc.); PI3 kinase inhibitors, Roche-5 (Roche Holdings Inc.); pictilisib (Roche Holdings Inc.); PI3 kinase delta inhibitors, Incozen (Incozen Therapeutics, Pvt. Ltd., Hydrabad, India); PI3 kinase delta inhibitors-2, Incozen (Incozen Therapeutics); PI3-delta inhibitors, Intellikine (Intellikine Inc., La Jolla, Calif.); PI3-delta/gamma inhibitors, Intellikine (Intellikine Inc.); PI3K delta/gamma inhibitors, Intellikine-1 (Intellikine Inc.); KAR-4139 (Karus Therapeutics, Chilworth, UK); KAR-4141 (Karus Therapeutics); PI3 kinase delta inhibitor, Merck KGaA (Merck & Co., Whitehouse Station, N.J.); OXY-111A (NormOxys Inc., Brighton, Mass.); PI3-alpha/delta inhibitors, Pathway Therapeutics (Pathway Therapeutics Ltd., South San Francisco, Calif.); PI3-delta inhibitors, Pathway Therapeutics-1 (Pathway Therapeutics Ltd.); PI3-delta inhibitors, Pathway Therapeutics-2 (Pathway Therapeutics Ltd.); PI3-delta/gamma inhibitors, Pathway Therapeutics (Pathway Therapeutics Ltd.); SF-1126 (Semafore Pharmaceuticals, Indianapolis, Ind.); X-339 (Xcovery, West Palm Beach, Fla.); IC87114 (Gilead Science); TG100-115 (Targegen Inc., San Diego, Calif.); and combinations thereof. Preferably, the PI3Kδ inhibitor is CAL-130. PI3Kδ inhibitor may also be a nucleic acid comprising an shRNA or an siRNA, preferably an shRNA.

In an aspect, a PI3Kγ inhibitor is an agent that is able to lower the activity level or the expression level of PI3Kγ. Preferably, the PI3Kγ inhibitor has few or no off-target effects; except that it is permissible, in accordance with the present disclosure, to also have an inhibitory effect on PI3Kδ as set forth in more detail above.

Further suitable PI3Kγ inhibitors include, without limitation, PI3-delta/gamma inhibitors, Cellzome (Cellzome AG);

PI3-gamma inhibitor, Cellzome (Cellzome AG); PI3-gamma inhibitor Evotec (Evotec); PI3 kinase inhibitors, Roche (Roche Holdings Inc.); pictilisib (Roche Holdings, Inc.); IPI-145 (Intellikine Inc.); PI3-delta/gamma inhibitors, Intellikine (Intellikine Inc.); PI3K delta/gamma inhibitors, Intellikine-1 (Intellikine Inc.); KIN-1 (Karus Therapeutics); PI3-delta/gamma inhibitors, Pathway Therapeutics (Pathway Therapeutics Ltd.); PI3-gamma inhibitors, Pathway Therapeutics (Pathway Therapeutics Ltd.); SC-103980 (Pfizer, New York, N.Y.); SF-1126 (Semafore Pharmaceuticals); AS-041164 (5-benzo[1,3]dioxol-5-ylmethylene-thiazolidine-2,4-dione); AS-604850 (5-(2,2-Difluoro-benzo[1,3]dioxol-5-ylmethylene)-thiazolidine-2,4-dione); TG100-115 (Targegen Inc., San Diego, Calif.); AS-605240 (5-quinoxilin-6-methylene-1,3-thiazolidine-2,4-dione); CAL-130 (Gilead Sciences); and combinations thereof. Preferably, the PI3Kγ inhibitor is CAL-130. PI3Kγ inhibitor may also be a nucleic acid comprising an shRNA or an siRNA, preferably an shRNA.

In the present disclosure, a single compound or composition that inhibits both PI3Kδ and PI3Kγ, but has no or limited effect on other PI3K isoforms, is also contemplated.

In the present disclosure, one or more PI3Kδ and/or PI3Kγ inhibitors and/or one or more chemotherapeutic agents may be co-administered to a subject in need thereof together in the same composition, simultaneously in separate compositions, or as separate compositions administered at different times, as deemed most appropriate by a physician.

In the present disclosure, an "effective amount" or "therapeutically effective amount" of a PI3K inhibitor, whether a PI3Kγ inhibitor or a PI3Kδ inhibitor, is an amount of such an inhibitor that is sufficient to effect beneficial or desired results as described herein when administered to a subject. Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of mammal, e.g., human patient, and like factors well known in the arts of medicine and veterinary medicine. In general, a suitable dose of a PI3K inhibitor according to the disclosure will be that amount of the PI3K inhibitor, which is the lowest dose effective to produce the desired effect with no or minimal side effects. The effective dose of a PI3Kγ inhibitor or a PI3Kδ inhibitor may be administered as two, three, four, five, six or more sub-doses, administered separately at appropriate intervals throughout the day, with the proviso that the doses of the PI3Kγ inhibitor or a PI3Kδ inhibitor simultaneously reduce or inhibit the activity or the expression levels of PI3Kγ and PI3Kδ.

A suitable, non-limiting example of a dosage of a PI3K inhibitor according to the present disclosure, particularly a PI3Kγ inhibitor and/or a PI3Kδ inhibitor, is from about 1 ng/kg to about 1000 mg/kg, such as from about 1 mg/kg to about 100 mg/kg, including from about 5 mg/kg to about 50 mg/kg. Other representative dosages of a PI3K inhibitor include about 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 400 mg/kg, 500 mg/kg, 600 mg/kg, 700 mg/kg, 800 mg/kg, 900 mg/kg, or 1000 mg/kg.

Another embodiment of the present disclosure is a method for treating, preventing, or ameliorating the effects of a lymphoid malignancy associated with a mutated phosphatase and tensin homolog (PTEN) gene and/or activation of PI3K/AKT signaling pathway in the subject. This method comprises administering to the subject an effective amount of a PI3Kδ inhibitor and a PI3Kγ inhibitor.

As used herein, a "mutated phosphatase and tensin homolog (PTEN) gene" means having one or more variations in the exon or the intron sequence of PTEN. A lymphoid malignancy "associated with a mutated PTEN gene" means a lymphoid malignancy in which one or more variations in the PTEN gene sequence is found and results in activation of the PI3K/AKT signaling pathway. Such lymphoid malignancies include, e.g., T-ALL, lymphoblastic lymphoma, large B-cell lymphoma, Burkitt's lymphoma, large B-cell lymphoma, and myeloma.

In an aspect, the disclosure provides for methods of treating a lymphoid malignancy or an abnormal growth of bodily tissue or cells in the lymphoid system. Such abnormal growth may invade and destroy nearby tissue, and may spread to other parts of the body. The term "lymphoid system" refers to all of the cells, tissue aggregates, and organs which function together to produce specific resistance to disease, including without limitation, the bone marrow, the thymus, lymphatic vessels, T-cells and their progenitor cells, as well as B-cells and their progenitor cells.

In an aspect, the disclosure provides for methods of treating and/or preventing Hodgkin's lymphoma, non-Hodgkin's lymphoma (NHL), and composite Hodgkin's lymphoma and NHL. Hodgkin's lymphoma include lymphocyte-rich classical Hodgkin's lymphoma, mixed-cellularity classical Hodgkin's lymphoma, lymphocyte-depleted classical Hodgkin's lymphoma, and nodular lymphocyte predominant Hodgkin's lymphoma, B-cell NHL, T-cell NHL, NHL of unknown lineage, B-cell NHL, precursor B-cell NHL (such as B lymphoblastic leukemia and B lymphoblastic lymphoma), chronic lymphocytic leukemia, small lymphocytic lymphoma, prolymphocytic leukemia, mantel-cell lymphoma, lymphoplasmacytic lymphoma, Waldenstrom macroglobulinemia, Burkitt lymphoma, follicular lymphoma, splenic marginal-zone lymphoma, extranodal marginal-zone lymphoma, nodal marginal-zone lymphoma, hairy-cell leukemia, diffuse large B-cell lymphoma, intravascular large B-cell lymphoma, primary effusion lymphoma, mediastinal large B-cell lymphoma, plasmacytoma, and multiple myeloma/plasma cell leukemia. T-cell NHL include precursor T-cell NHL (such as T-cell acute lymphoblastic leukemia (T-ALL) and T-cell acute lymphoblastic lymphoma), mycosis fungoides, Sezary syndrome, adult T-cell leukemia, adult T-cell lymphoma, NK/T-cell lymphoma, aggressive NK-cell leukemia, T-cell large granular lymphocytic leukemia, T-cell prolymphocytic leukemia, and peripheral T-cell lymphoma (such as angioimmunoblastic lymphoma, subcutaneous panniculitis-like T-cell lymphoma, anaplastic large-cell lymphoma, hepatoplenic T-cell lymphoma, enteropathy-type T-cell lymphoma, cutaneous T-cell lymphoma, primary cutaneous anaplastic large-cell lymphoma). Preferably, the lymphoid malignancy is T-ALL or T-cell acute lymphoblastic lymphoma. In another preferred embodiment, wherein the lymphoid malignancy is T-ALL.

In one aspect of this embodiment, the method further comprises administering an effective amount of a chemotherapeutic agent as disclosed herein, such as a glucocorticoid. Preferably, the chemotherapeutic agent is dexamethasone.

Yet another embodiment of the present disclosure is a pharmaceutical composition for treating the effects of a lymphoid malignancy. This pharmaceutical composition comprises a pharmaceutically acceptable carrier and an effective amount of a PI3Kδ inhibitor and a PI3Kγ inhibitor described herein. In one embodiment, the PI3Kδ inhibitor and the PI3Kγ inhibitor are selected from the group consisting of: IPI-145/Duvelisib, RP6530, CUX-03190, CUX-03193, CUX-03198A, CUX-03198B, DWL-PI3K-1, DWL-PI3K-2, DWL-PI3K-3, and DWL-PI3K-4, DWL-PI3K-5, DWL-PI3K-6, and DWL-PI3K-7.

Representative structures are as follows, including compounds designated as CU-17037:

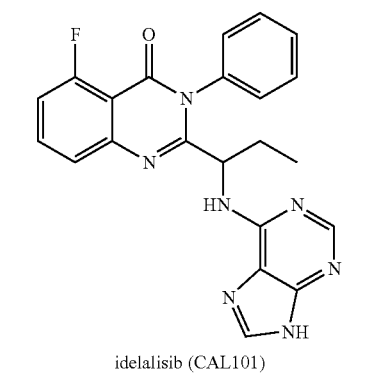

idelalisib (CAL101)

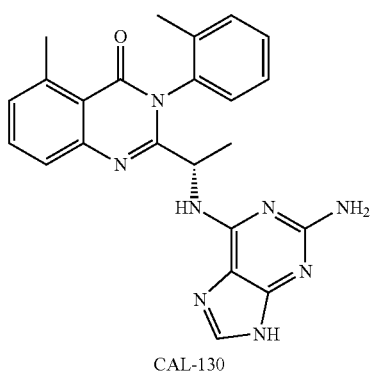

CAL-130

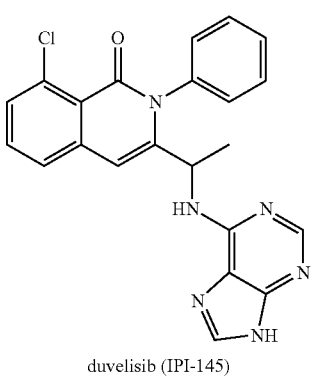

duvelisib (IPI-145)

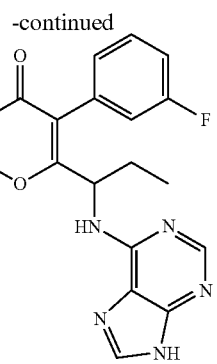

RP6530

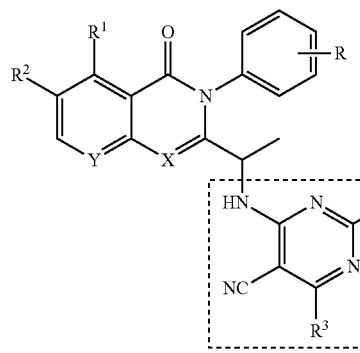

CU-17037
$R^1$ = CH$_3$, Cl, F, N(CH$_3$)$_2$, etc.
$R^2$ = Br, Cl, CH$_3$, X, Y = C or N
$R^3$ = NH$_2$ or CH$_3$
R = H, F, Cl, CH$_3$, etc.

The pharmaceutical composition of this embodiment may be a single composition containing a dual inhibitor, a single composition containing two active agents, one a PI3Kδ inhibitor and the other a PI3Kγ inhibitor, or two or more compositions each containing at least one active agent that is a PI3Kδ inhibitor or a PI3Kγ inhibitor.

In another aspect, the pharmaceutical composition further comprises an effective amount of a chemotherapeutic agent as disclosed herein, such as a glucocorticoid. Preferably, the chemotherapeutic agent is dexamethasone.

The pharmaceutical composition of this embodiment may be a single composition containing a dual inhibitor, a single composition containing two active agents, one a PI3Kδ inhibitor and the other a PI3Kγ inhibitor, or two or more compositions each containing at least one active agent that is a PI3Kδ inhibitor or a PI3Kγ inhibitor.

In an aspect of this embodiment, the method further comprises administering an effective amount of a chemotherapeutic agent as disclosed herein, such as a glucocorticoid. Preferably, the chemotherapeutic agent is dexamethasone.

Another embodiment of the present disclosure is a method for lowering tumor burden in a subject suffering from T-ALL. This method comprises administering to the subject an effective amount of a pharmaceutical composition comprising a PI3Kδ inhibitor and a PI3Kγ inhibitor described herein.

As used herein, "tumor burden" means the number of tumor (whether benign or malignant) cells in the subject's body, or the size of a tumor.

In one aspect of this embodiment, the method further comprises administering an effective amount of a chemotherapeutic agent as disclosed herein, such as a glucocorticoid also as defined herein. Preferably, the chemotherapeutic agent is dexamethasone.

Yet another embodiment of the present disclosure is a method for identifying a subject who may benefit from co-treatment with a PI3Kδ inhibitor and a PI3Kγ inhibitor. This method comprises determining from a sample of the subject whether the subject has a mutated PTEN gene, wherein the presence of the mutated PTEN gene and the subsequent activation of the PI3K/AKT signaling pathway is indicative of a subject who may benefit from co-treatment.

In this embodiment, the sample is obtained from the subject by any conventional means. Such a sample contains DNA and may be a tissue and/or blood sample, such as a peripheral blood sample. Such a sample may also be biopsy from a tumor. Determining whether a subject has a mutated PTEN gene may be carried out using any conventional genotyping methods known in the art, or by assaying for the PTEN gene product using any conventional means, including the methods disclosed herein, including in the Examples. Determining whether a subject has a activation of the PI3K/AKT pathway s carried out by Western Blot Analysis to detect the phosphorylation of AKT or by Phospho-flow assays.

An additional embodiment of the present disclosure is a method for identifying a compound that has both PI3Kδ and PI3Kγ inhibitory activity. This method comprises: (a) contacting a cell with the compound; and (b) determining whether the compound modulates an antigen receptor-induced activity in the cell; wherein a compound that modulates the antigen receptor-induced activity has both PI3Kδ and PI3Kγ inhibitory activity.

As used herein, an "antigen receptor-induced activity" means an event resulting from T-cell receptor signaling, such as, e.g., phosphorylation of AKT, GSK3β, mTOR, p70S6K, prosurvival proteins and calcium flux in CD4 T cells. Assays for such activities are as disclosed herein.

A pharmaceutical composition of the present disclosure may be administered in any desired and effective manner: for oral ingestion, or as an ointment or drop for local administration to the eyes, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. Further, a pharmaceutical composition of the present disclosure may be administered in conjunction with other treatments. A pharmaceutical composition of the present disclosure maybe encapsulated or otherwise protected against gastric or other secretions, if desired.

The pharmaceutical compositions of the disclosure are pharmaceutically acceptable and comprise one or more active ingredients in admixture with one or more pharmaceutically-acceptable carriers and, optionally, one or more other compounds, drugs, ingredients and/or materials. Regardless of the route of administration selected, the agents/compounds of the present disclosure are formulated into pharmaceutically-acceptable dosage forms by conventional methods known to those of skill in the art. See, e.g., Remington, The Science and Practice of Pharmacy (21st Edition, Lippincott Williams and Wilkins, Philadelphia, Pa.).

Pharmaceutically acceptable carriers are well known in the art (see, e.g., Remington, The Science and Practice of Pharmacy (21st Edition, Lippincott Williams and Wilkins, Philadelphia, Pa.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable carrier used in a pharmaceutical composition of the disclosure must be "acceptable" in the sense of being compatible with the other ingredients of the formulation and not injurious to the subject. Carriers suitable for a selected dosage form and intended route of administration are well known in the art, and acceptable carriers for a chosen dosage form and method of administration can be determined using ordinary skill in the art.

The pharmaceutical compositions of the disclosure may, optionally, contain additional ingredients and/or materials commonly used in such pharmaceutical compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monosterate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

Pharmaceutical compositions suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared, e.g., by mixing the active ingredient(s) with one or more pharmaceutically-acceptable carriers and, optionally, one or more fillers, extenders, binders, humectants, disintegrating agents, solution retarding agents, absorption accelerators, wetting agents, absorbents, lubricants, and/or coloring agents. Solid compositions of a similar type maybe employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. The active ingredient can also be in microencapsulated form.

Liquid dosage forms for oral administration include pharmaceutically-acceptable emulsions, microemulsions, solutions, suspensions, syrups and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

Pharmaceutical compositions for rectal or vaginal administration may be presented as a suppository, which may be prepared by mixing one or more active ingredient(s) with one or more suitable nonirritating carriers which are solid at room temperature, but liquid at body temperature and, therefore, will melt in the rectum or vaginal cavity and release the active compound. Pharmaceutical compositions which are suitable for vaginal administration also include pessaries, tampons, creams, gels, pastes, foams or spray formulations containing such pharmaceutically-acceptable carriers as are known in the art to be appropriate.

Dosage forms for the topical or transdermal administration include powders, sprays, ointments, pastes, creams, lotions, gels, solutions, patches, drops and inhalants. The active agent(s)/compound(s) may be mixed under sterile conditions with a suitable pharmaceutically-acceptable carrier. The ointments, pastes, creams and gels may contain excipients. Powders and sprays may contain excipients and propellants.

Pharmaceutical compositions suitable for parenteral administrations comprise one or more agent(s)/compound(s) in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

In some cases, to prolong the effect of a drug (e.g., pharmaceutical formulation), it is desirable to slow its absorption from subcutaneous or intramuscular injection. This may be accomplished by use of a liquid suspension of crystalline or amorphous material having poor water solubility.

The rate of absorption of the active agent/drug then depends upon its rate of dissolution which, in turn, may depend upon crystal size and crystalline form. Alternatively, delayed absorption of a parenterally-administered agent/drug may be accomplished by dissolving or suspending the active agent/drug in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

"Nucleic acid" or "oligonucleotide" or "polynucleotide" as used herein mean at least two nucleotides covalently linked together. Many variants of a nucleic acid may be used for the same purpose as a given nucleic acid. Thus, a nucleic acid also encompasses substantially identical nucleic acids and complements thereof.

Nucleic acids may be single-stranded or double-stranded, or may contain portions of both double stranded and single stranded sequences. The nucleic acid may be DNA, both genomic and cDNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine. Nucleic acids may be synthesized as a single stranded molecule or expressed in a cell (in vitro or in vivo) using a synthetic gene. Nucleic acids may be obtained by chemical synthesis methods or by recombinant methods.

The nucleic acid may also be a RNA such as a mRNA, tRNA, short hairpin RNA (shRNA), short interfering RNA (sRNA), double-stranded RNA (dsRNA), transcriptional gene silencing RNA (ptgsRNA), Piwi-interacting RNA, pri-miRNA, pre-miRNA, micro-RNA (miRNA), or anti-miRNA, as described, e.g., in U.S. patent application Ser. Nos. 11/429,720, 11/384,049, 11/418,870, and 11/429,720 and Published International Application Nos. WO 2005/116250 and WO 2006/126040.

siRNA gene-targeting may be carried out by transient siRNA transfer into cells, achieved by such classic methods as lipid-mediated transfection (such as encapsulation in liposome, complexing with cationic lipids, cholesterol, and/or condensing polymers, electroporation, or microinjection). siRNA gene-targeting may also be carried out by administration of siRNA conjugated with antibodies or siRNA complexed with a fusion protein comprising a cell-penetrating peptide conjugated to a double-stranded (ds) RNA-binding domain (DRBD) that binds to the siRNA (see, e.g., U.S. Patent Application Publication No. 2009/0093026).

An shRNA molecule has two sequence regions that are reversely complementary to one another and can form a double strand with one another in an intramolecular manner. shRNA gene-targeting may be carried out by using a vector introduced into cells, such as viral vectors (lentiviral vectors, adenoviral vectors, or adeno-associated viral vectors for example). The design and synthesis of siRNA and shRNA molecules are known in the art, and may be commercially purchased from, e.g., Gene Link (Hawthorne, N.Y.), Invitrogen Corp. (Carlsbad, Calif.), Thermo Fisher Scientific, and Dharmacon Products (Lafayette, Colo.).

The nucleic acid may also be an aptamer, an intramer, or a spiegelmer. The term "aptamer" refers to a nucleic acid or oligonucleotide molecule that binds to a specific molecular target. Aptamers are derived from an in vitro evolutionary process (e.g., SELEX (Systematic Evolution of Ligands by EXponential Enrichment), disclosed in U.S. Pat. No. 5,270,163), which selects for target-specific aptamer sequences from large combinatorial libraries. Aptamer compositions may be double-stranded or single-stranded, and may include deoxyribonucleotides, ribonucleotides, nucleotide derivatives, or other nucleotide-like molecules. The nucleotide components of an aptamer may have modified sugar groups (e.g., the 2'—OH group of a ribonucleotide may be replaced by 2'-F or 2'-NH$_2$), which may improve a desired property, e.g., resistance to nucleases or longer lifetime in blood. Aptamers may be conjugated to other molecules, e.g., a high molecular weight carrier to slow clearance of the aptamer from the circulatory system. Aptamers may be specifically cross-linked to their cognate ligands, e.g., by photo-activation of a cross-linker.

The term "intramer" refers to an aptamer which is expressed in vivo. For example, a vaccinia virus-based RNA expression system has been used to express specific RNA aptamers at high levels in the cytoplasm of leukocytes.

The term "spiegelmer" refers to an aptamer which includes L-DNA, L-RNA, or other left-handed nucleotide derivatives or nucleotide-like molecules. Aptamers containing left-handed nucleotides are resistant to degradation by naturally occurring enzymes, which normally act on substrates containing right-handed nucleotides.

A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those disclosed in U.S. Pat. Nos. 5,235,033 and 5,034,506. Nucleic acids containing one or more non-naturally occurring or modified nucleotides are also included within the definition of nucleic acid. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7-deaza-adenosine; 0- and N-alkylated nucleotides, e.g. N6-methyl adenosine are suitable. The 2'-OH-group may be replaced by a group selected from H, OR, R, halo, SH, SR, NH$_2$, NHR, NR$_2$ or CN, wherein R is C$_1$-C$_6$ alkyl, alkenyl or alkynyl and halo is F, Cl, Br or I. Modified nucleotides also include nucleotides conjugated with cholesterol through, e.g., a hydroxyprolinol linkage as disclosed in Krutzfeldt et al., Nature (Oct. 30, 2005), Soutschek et al., Nature 432:173-178 (2004), and U.S. Patent Application Publication No. 20050107325. Modified nucleotides and nucleic acids may also include locked nucleic acids (LNA), as disclosed in U.S. Patent Application Publication No. 20020115080. Additional modified nucleotides and nucleic acids are disclosed in U.S. Patent Application Publication No. 20050182005. Modifications of the ribose-phosphate backbone may be done for a variety of reasons, e.g., to increase the stability and half-life of such molecules in physiological environments, to enhance diffusion across cell membranes, or as probes on a biochip. Mixtures of naturally occurring nucleic acids and analogs may be made; alternatively, mixtures of different nucleic acid analogs, and mixtures of naturally occurring nucleic acids and analogs may be made.

As used herein, the terms "peptide," "polypeptide," and "protein" are interchangeable. In the present disclosure, these terms mean a linked sequence of amino acids, which may be natural, synthetic, or a modification, or combination of natural and synthetic. The term includes antibodies, antibody mimetics, domain antibodies, lipocalins, targeted proteases, and polypeptide mimetics. The term also includes vaccines containing a peptide or peptide fragment intended to raise antibodies against the peptide or peptide fragment.

As used herein, the term "polysaccharides" means polymeric carbohydrate structures, formed of repeating units (either mono- or di-saccharides) joined together by glycosidic bonds. The units of mono- or di-saccharides may be the same or different. Non-limiting examples of polysaccharides include starch, glycogen, cellulose, and chitin.

As used herein, the terms "small organic molecule" or "small inorganic molecule" include any chemical or other moiety, other than polysaccharides, polypeptides, and nucleic acids, that can act to affect biological processes. Small molecules can include any number of therapeutic agents presently known and used, or can be synthesized in a library of such molecules for the purpose of screening for biological function(s). Small molecules are distinguished from macromolecules by size. The small molecules of this disclosure usually have a molecular weight less than about 5,000 daltons (Da), preferably less than about 2,500 Da, more preferably less than 1,000 Da, most preferably less than about 500 Da.

As used herein, the term "organic compound" refers to any carbon-based compound other than biologics such as nucleic acids, polypeptides, and polysaccharides. In addition to carbon, organic compounds may contain calcium, chlorine, fluorine, copper, hydrogen, iron, potassium, nitrogen, oxygen, sulfur and other elements. An organic compound may be in an aromatic or aliphatic form. Non-limiting examples of organic compounds include acetones, alcohols, anilines, carbohydrates, mono-saccharides, di-saccharides, amino acids, nucleosides, nucleotides, lipids, retinoids, steroids, proteoglycans, ketones, aldehydes, saturated, unsaturated and polyunsaturated fats, oils and waxes, alkenes, esters, ethers, thiols, sulfides, cyclic compounds, heterocyclic compounds, imidizoles, and phenols. An organic compound as used herein also includes nitrated organic compounds and halogenated (e.g., chlorinated) organic compounds. Collections of small molecules, and small molecules identified according to the disclosure are characterized by techniques such as accelerator mass spectrometry (AMS).

Preferred small molecules are relatively easier and less expensively manufactured, formulated or otherwise prepared. Preferred small molecules are stable under a variety of storage conditions. Preferred small molecules may be placed in tight association with macromolecules to form molecules that are biologically active and that have improved pharmaceutical properties. Improved pharmaceutical properties include changes in circulation time, distribution, metabolism, modification, excretion, secretion, elimination, and stability that are favorable to the desired biological activity. Improved pharmaceutical properties include changes in the toxicological and efficacy characteristics of the chemical entity.

In an aspect and as described herein, PI3Kγ and PI3Kδ can act as a tumorigenic bottleneck in PTEN null T-ALL as their combined deletion significantly impaired tumor development in mice. The description further demonstrates that it is possible to exploit this PI3K "addiction" by identifying a lead dual PI3Kγ/δ inhibitor (CAL-130) that (1) significantly reduced tumor burden and prolonged survival of diseased mice, and (2) abolished Akt phosphorylation and activated pro-apoptotic pathways in human primary T-ALL cells. The disclosure further demonstrates the reliance of PTEN null T-ALL on the combined activities of PI3Kγ/δ.

This was also accomplished by generating gene expression signatures to assess the effects of drug treatment. Global gene expression profiles were obtained in triplicate using a mouse PTEN null/NOTCH activated T-ALL cell line driven by over expression of the transcription factor LMO2. In this model, tumor cells are characterized by activation of the PI3K pathways and NOTCH1, both of which are upregulated in human T-ALL. Tumor cells were cultured in the presence of CAL-130 (2.5 μM) or the gamma-secretase inhibitor (GSI) Compound E (1 μM). Compound E blocks the activity of NOTCH1, which is also believed to support T-ALL tumor formation, proliferation, and survival. Drug treated cells were harvested at time points known to affect the expression of the proto-oncogene cMyc (12 hours and 48 hours, respectively), a master regulator of cell growth, metabolism and survival. A Venn diagram was created to illustrate the overlap in genes altered by either PI3Kγ/δ blockade (red circle) or GSI (green circle) using a false discovery rate (FDR) of 0.0005 as cut off (FIG. 1A). Of note, ten-fold more genes were affected following PI3Kγ/δ blockade, including the majority (~62%) of genes altered by GSI monotherapy, a highly significant finding (Fisher's exact test, $P<2.2\times10^{-16}$).

A murine T-ALL disease signature was further defined by ranking all genes based on their differential expression in T-ALL samples compared to wild type murine thymocytes. To determine the contribution of PI3Kγ/δ and NOTCH1 to the overall disease signature, a gene set enrichment analysis (GSEA) of the 200 most transcriptionally activated and repressed genes was performed following treatment with either CAL-130 or Compound E in differentially expressed genes. Although both drugs significantly inverted the T-ALL disease signature, underscoring the importance of these signaling pathways in maintaining the leukemic phenotype (FIG. 1B), the enrichment was much more significant with CAL-130 (normalized enrichment score (NES) of −5.8 (P<0.0001) for CAL-130 versus NES of −2.6 (P=0.006) for Compound E. These results indicate that PI3Kγ/δ play a major role in T-ALL and regulate more genes that control the disease signature than NOTCH1, which was thought to be the major oncogene associated with this leukemia.

The PI3K inhibitor Duvelisib (IPI-145) was not as effective in reducing tumor burden or in prolonging overall survival of mice with T-ALL (see FIG. 1B; mean survival of 18 days (IPI-145; 30 mg/kg tid) vs. 45 days (CAL-130; 10 mg/kg tid)).

It has been found that the claimed compounds display a broad range of potencies when assayed for their abilities to kill cultured T-ALL cells. Some compounds exhibited even higher activity than CAL-130 (eg. kill at nanoMolar concentrations rather than microMolar concentration) and may have potential to be developed into treatments for aggressive or relapsed T-ALL.

This cohort of diverse PI3Kγ/δ inhibitors has potential to be developed into treatments for cancers such as T-ALL, as well as for other diseases associated with aberrant PI3K activity. These compounds further serve as promising tools for inhibiting PI3Kγ/δ activity in PI3K/Akt signaling research, as well as for inducing cell death at a variety of strengths for research.

Figure 5A:
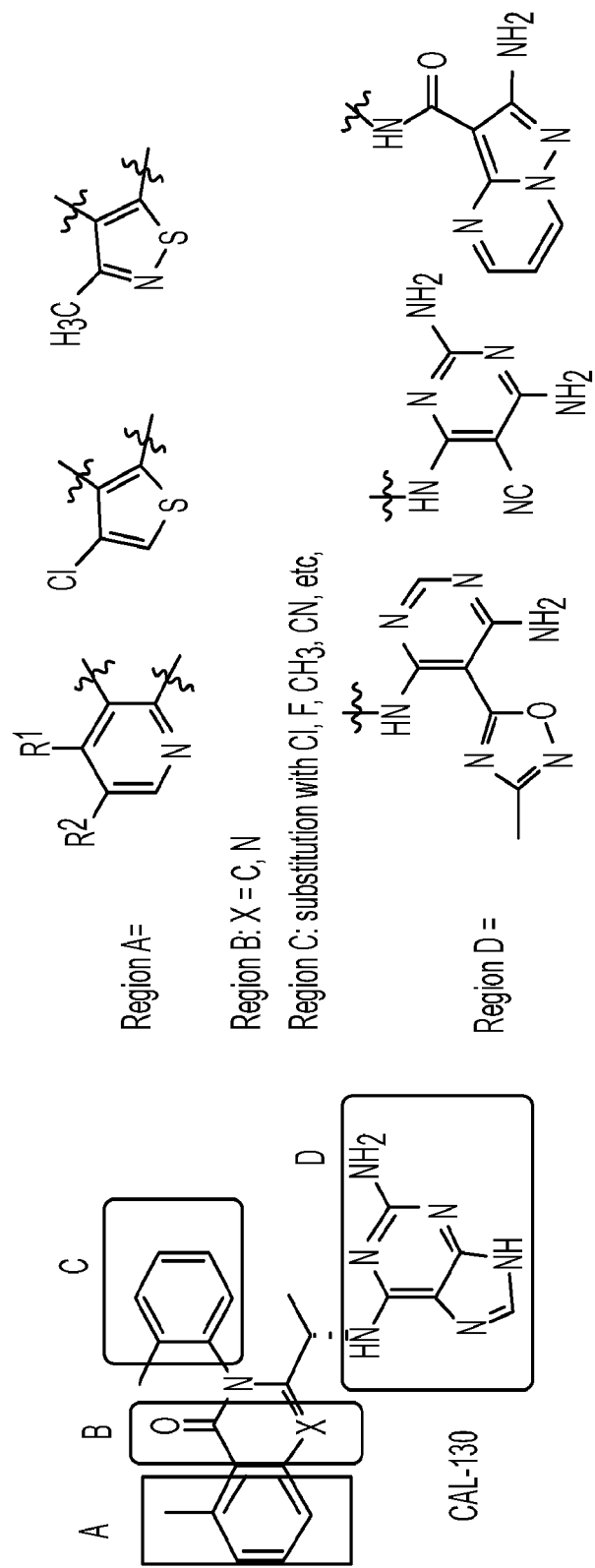
FIG. 5A shows structural analysis and modifications of CAL-130.

Further optimization of small-molecule PI3Kγ/δ dual inhibitors was performed. As illustrated in FIG. 5A, the structure of CAL-130 can be subdivided into four major regions: Regions A, B, C and D. DWL-PI3K-3 and DWL-PI3K-4 exhibit greater efficacy than CAL-130 in inducing T-ALL cell death. In Region A, the phenyl rings include different substituents, such as Cl, F, CF3, OCH3.

Figure 5B:
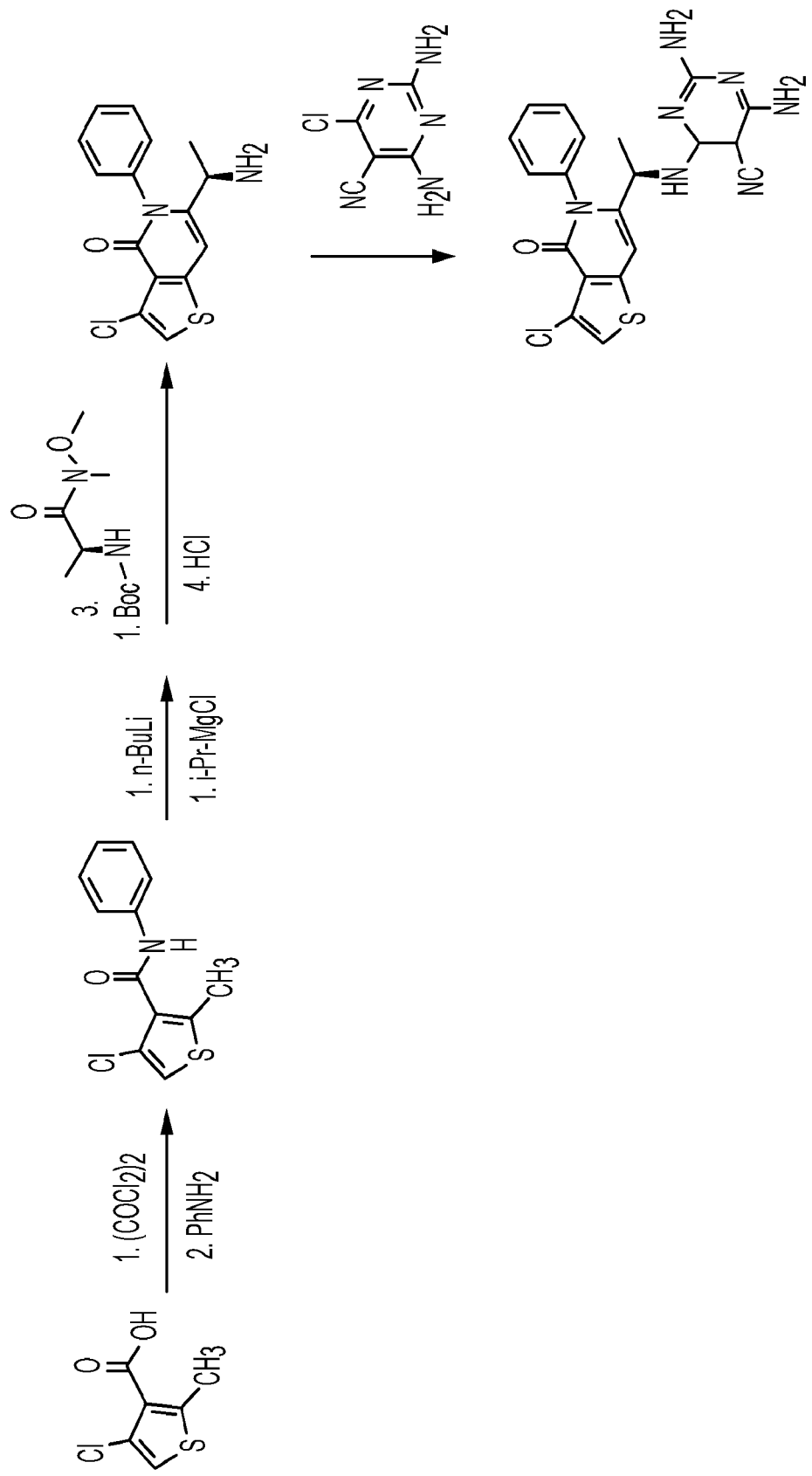
FIG. 5B depicts an example of synthesis of a PI3Kδ and PI3Kγ dual inhibitor.
Figure 6:
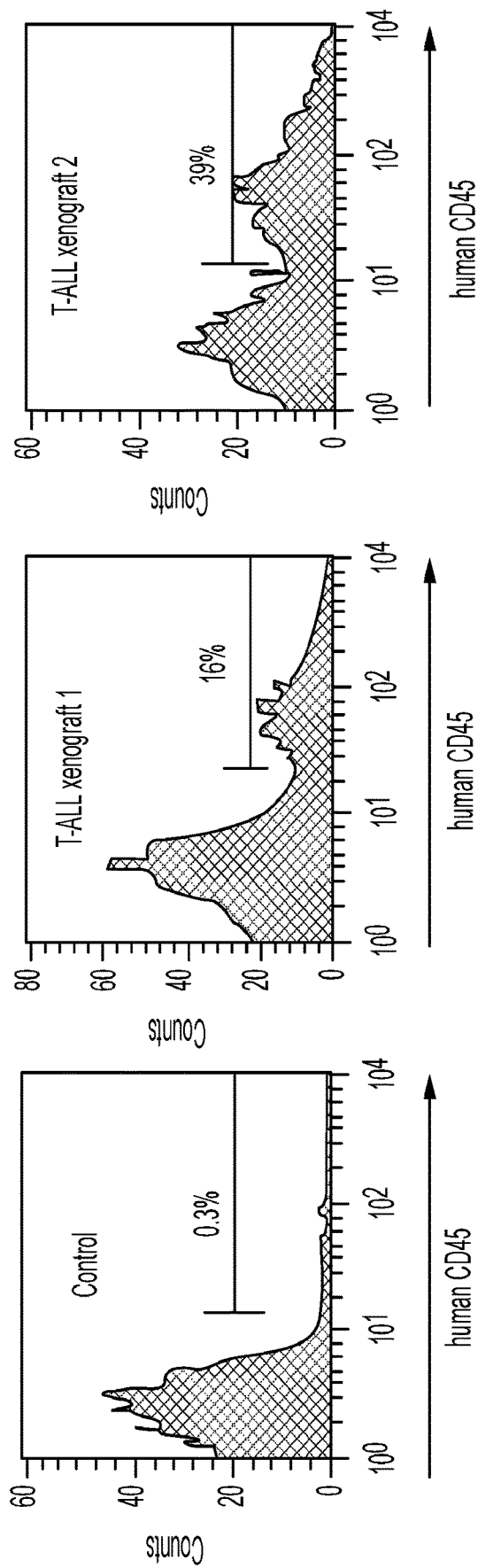
FIG. 6 shows primary T-ALL xenografts engrafted in NOD.Cg-Prkdc$^{scid}$ Il2rg$^{tm1Wjl}$/Sz mice. Tumor development is monitored by analysis of human CD45 by flow cytometry. This xenograft model would complement mouse tumor studies, by performing a detailed analysis of drug response of primary human T-ALL cells, by engrafting them into NOD.Cg-Prkdc$^{scid}$ Il2rg$^{tm1Wjl}$/Sz mice.
Figure 7:
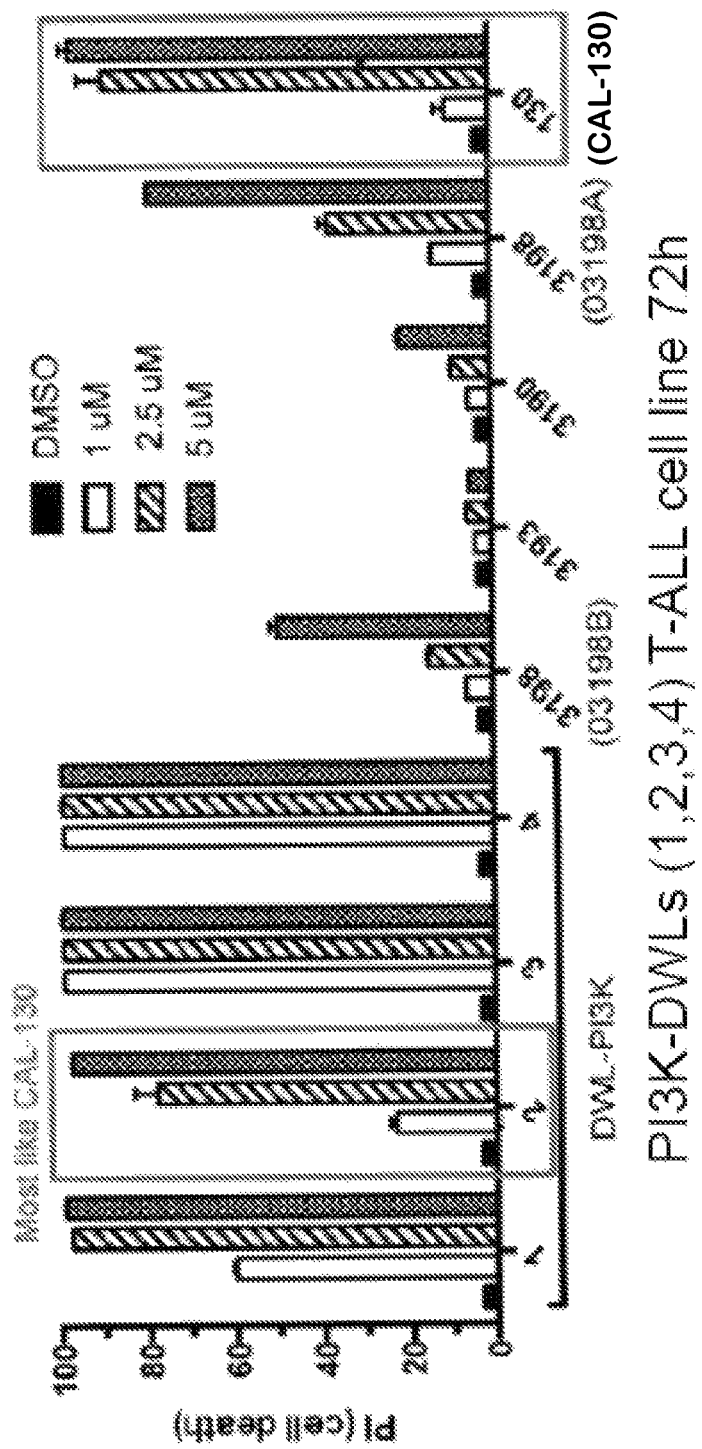
FIG. 7 is a chart comparing results (PI cell death) after treating a T-ALL cell line for 72 hours with DWL-PI3K-1, DWL-PI3K-2, DWL-PI3K-3, DWL-PI3K-4, and other PI3K inhibitors.
Figure 8:
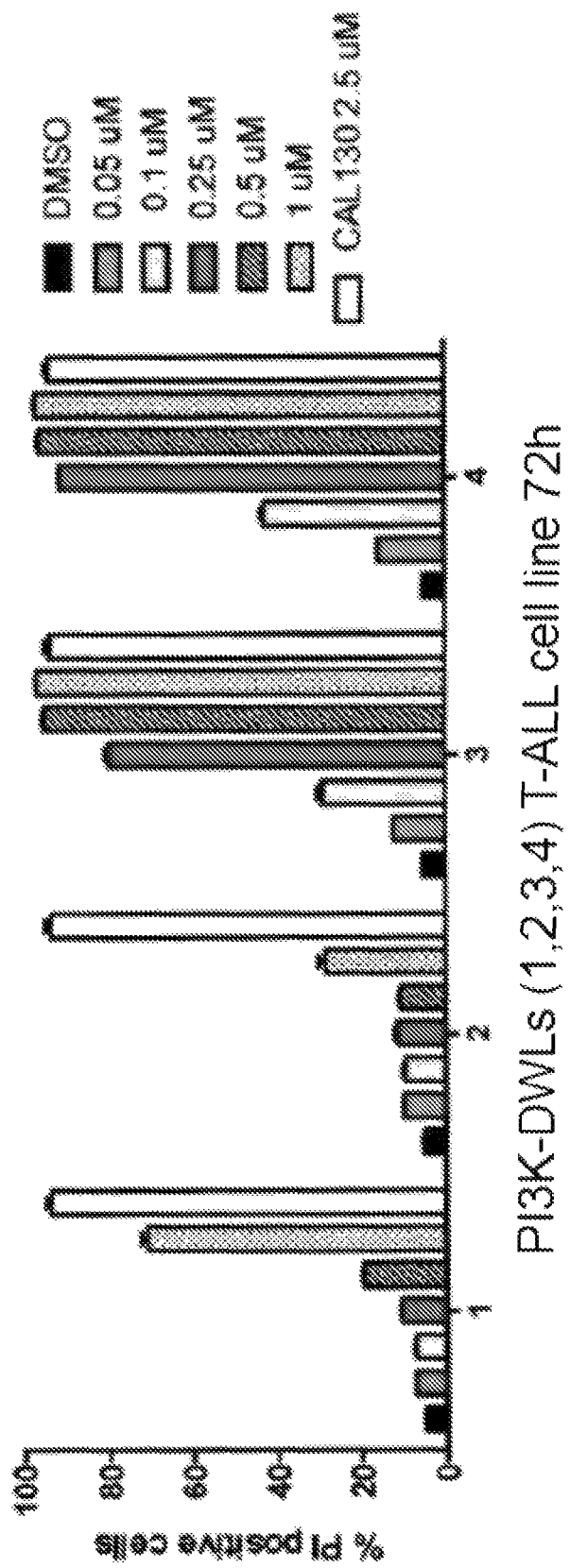
FIG. 8 is a chart showing results (PI positive cells) after treating a T-ALL cell line for 72 hours with DWL-PI3K-1, DWL-PI3K-2, DWL-PI3K-3, DWL-PI3K-4, and CAL-130.
Figure 9:
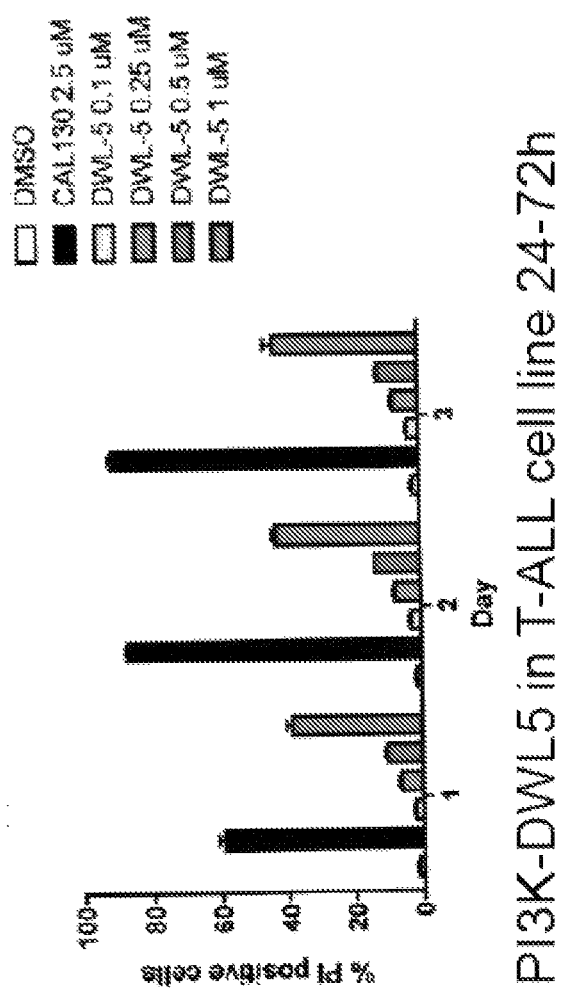
FIG. 9 is a chart showing results (PI positive cells) after treating a T-ALL cell line with DWL-PI3K-5.
Figure 10:
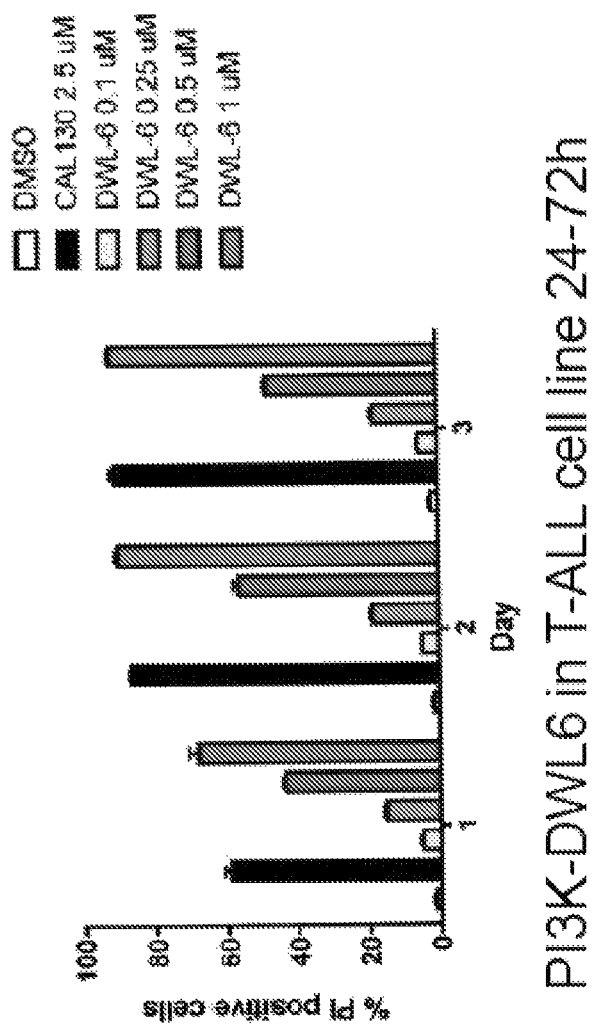
FIG. 10 is a chart showing results (PI positive cells) after treating a T-ALL cell line with DWL-PI3K-6.
Figure 11:
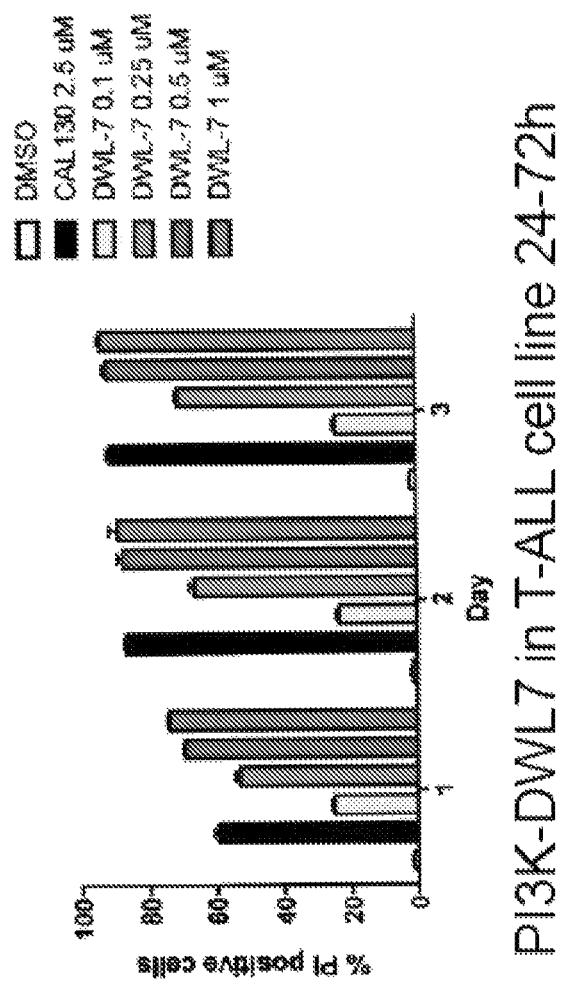
FIG. 11 is a chart showing results (PI positive cells) after treating a T-ALL cell line with DWL-PI3K-7.
Figure 12:
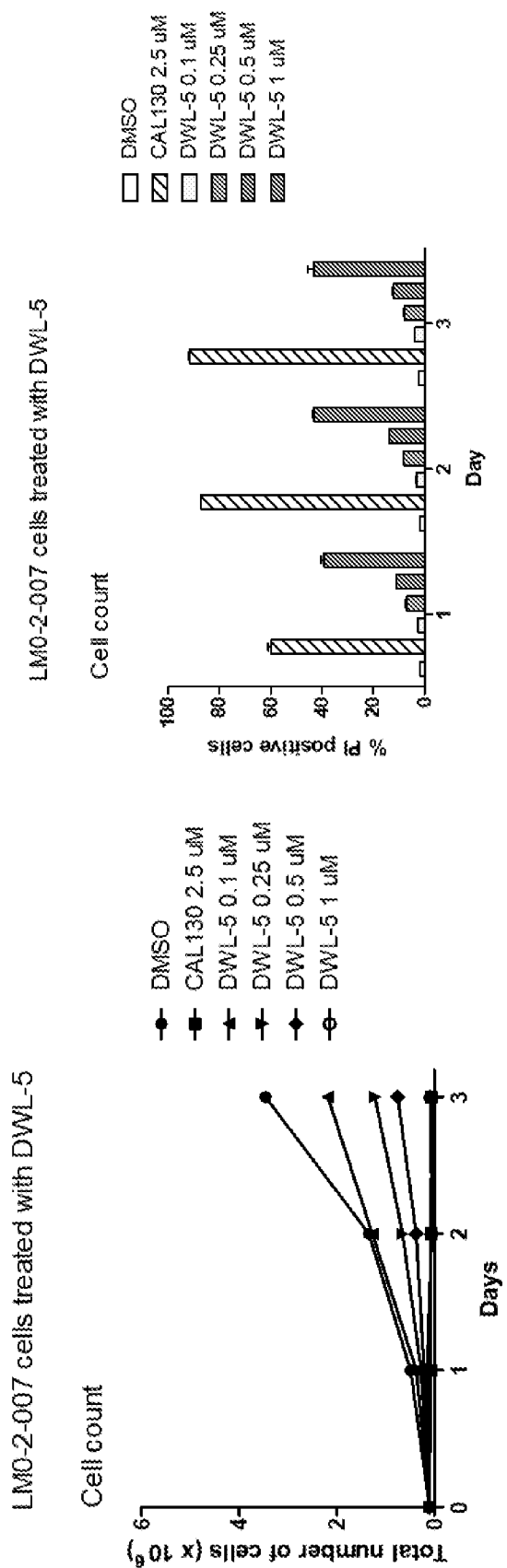
FIG. 12 shows results of treating LMO-2-007 cells with CAL130 and various concentrations of DWL-PI3K-5.
Figure 13:
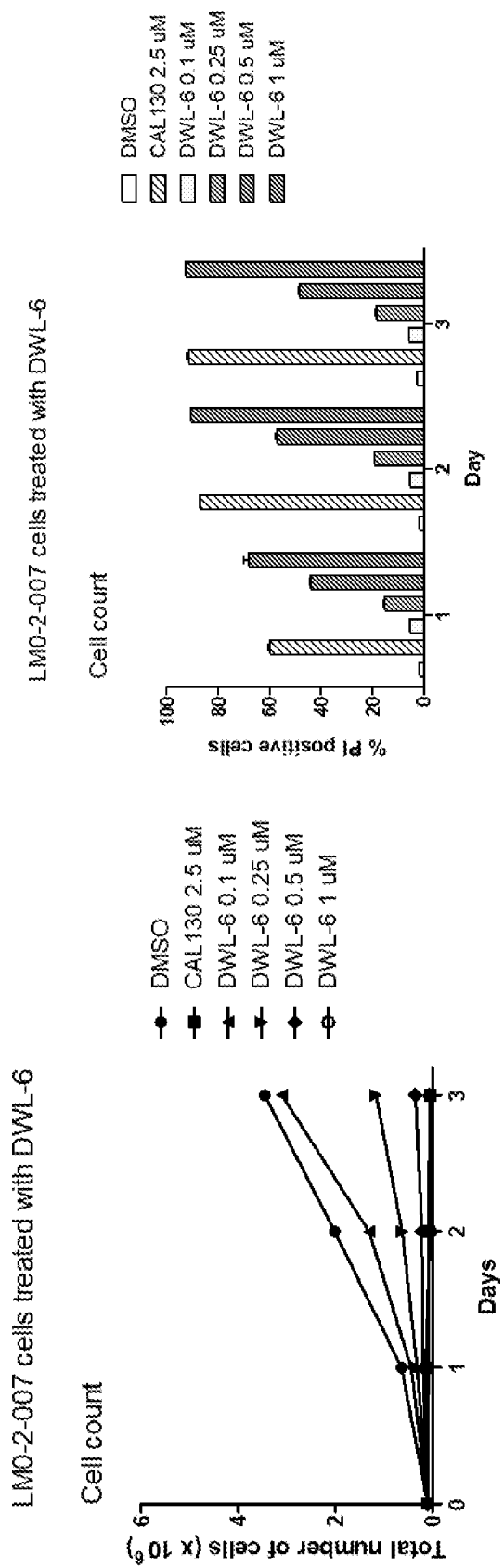
FIG. 13 shows results of treating LMO-2-007 cells with CAL130 and various concentrations of DWL-PI3K-6.
Figure 14:
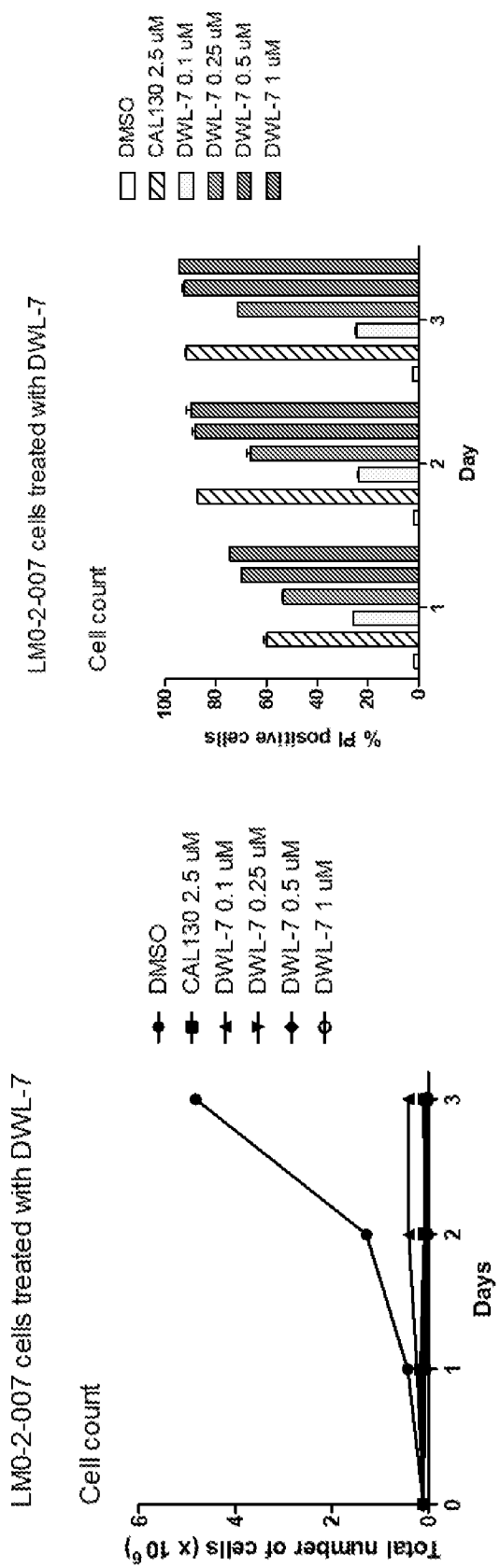
FIG. 14 shows results of treating LMO-2-007 cells with CAL130 and various concentrations of DWL-PI3K-7.
Figure 15:
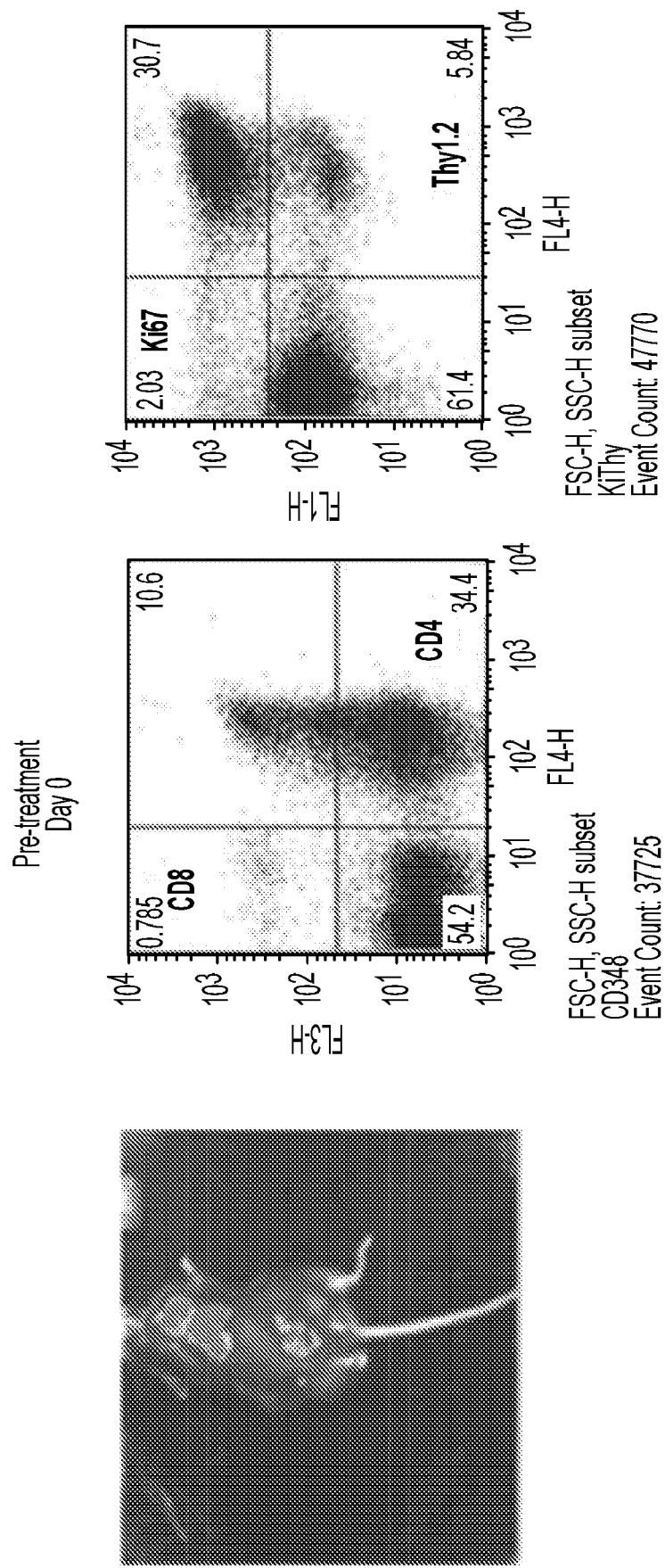
FIG. 15 (pre-treatment) and FIG. 16 (post-treatment) show in vivo results of treating mice with DWL-PI3K-3.

In some analogs the phenyl ring can be replaced with heteroaryl groups, such as pyridine, pyrimidine, thiophene. In Region B, the nitrogen (X═N) is replaced with a CH group (X═CH). In Region C, similar to Region A, in some analogs the phenyl ring can bear a number of different substituents or have a different substitution pattern. In Region D, heteroaryl groups, such as the ones listed in FIG. 5A, are introduced. FIG. 5B presents an example of a synthesis of an analog bearing a thiophene in place of the phenyl group in Region A, a CH group instead of a nitrogen in the pyrimidinone ring in Region B, an unsubstituted phenyl ring in Region C, and a pyrimidine ring in Region D.

In one embodiment of the present disclosure is a method for treating, preventing, or ameliorating the effects of a lymphoid malignancy. This method comprises administering to a subject in need thereof an effective amount of a PI3Kδ inhibitor and a PI3Kγ inhibitor.

As used herein, a "subject" is a mammal, preferably, a human. In addition to humans, categories of mammals within the scope of the present disclosure include, for example, agricultural animals, domestic animals, laboratory animals, etc. Some examples of agricultural animals include cows, pigs, horses, goats, etc. Some examples of domestic animals include dogs, cats, etc. Some examples of laboratory animals include rats, mice, rabbits, guinea pigs, etc.

As used herein, the terms "treat," "treating," "treatment" and grammatical variations thereof mean subjecting an individual subject to a protocol, regimen, process or remedy, in which it is desired to obtain a physiologic response or outcome in that subject, e.g., a patient. In particular, the methods and compositions of the present disclosure may be used to slow the development of disease symptoms or delay the onset of the disease or condition, or halt the progression of disease development. However, because every treated subject may not respond to a particular treatment protocol, regimen, process or remedy, treating does not require that the desired physiologic response or outcome be achieved in each and every subject or subject, e.g., patient, population. Accordingly, a given subject or subject, e.g., patient, population may fail to respond or respond inadequately to treatment.

As used herein, the terms "ameliorate", "ameliorating" and grammatical variations thereof mean to decrease the severity of the symptoms of a disease in a subject.

As used herein, the terms "prevent", "preventing" and grammatical variations thereof mean to administer a compound or composition of the present disclosure to a subject who has not been diagnosed as having the disease or condition at the time of administration, but who could be expected to develop the disease or condition or be at increased risk for the disease or condition. Preventing also includes administration of at least one compound or a composition of the present disclosure to those subjects thought to be predisposed to the disease or condition due to age, familial history, genetic or chromosomal abnormalities, due to the presence of one or more biological markers for the disease or condition and/or due to environmental factors.

As used herein, a "biologic" means a substance which is derived from or produced by a living organism or synthesized to mimic an in vivo-derived agent or a derivative or product thereof. A biologic may be, for example, a nucleic acid, a polypeptide, or a polysaccharide. Preferably, the biologic is a nucleic acid, a protein, or a combination thereof. More preferably, the nucleic acid comprises an shRNA.

As used herein, a "chemical" means a substance that has a definite chemical composition and characteristic properties and that is not a biologic. Non-limiting examples of chemicals include small organic compounds and small inorganic compounds.

The following examples serve to illustrate certain aspects of the disclosure and are not intended to limit the disclosure.

EXAMPLES

Figure 4C:
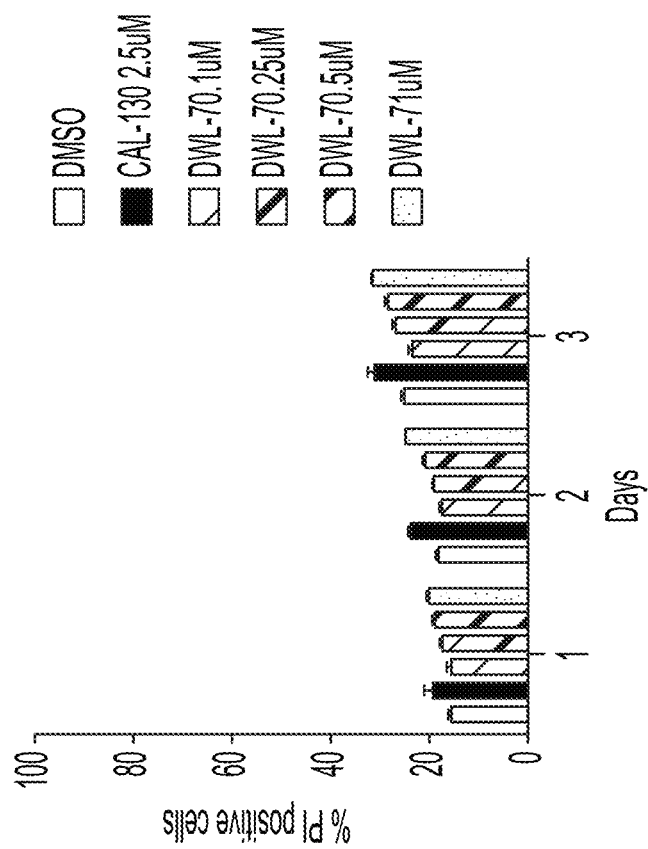
FIG. 4C shows limited killing effect of compound DWL-PI3K-7 (Ex. No. 1-50 as described herein) on a T-ALL cell line lacking p110γ and p110δ.
Figure 4B:
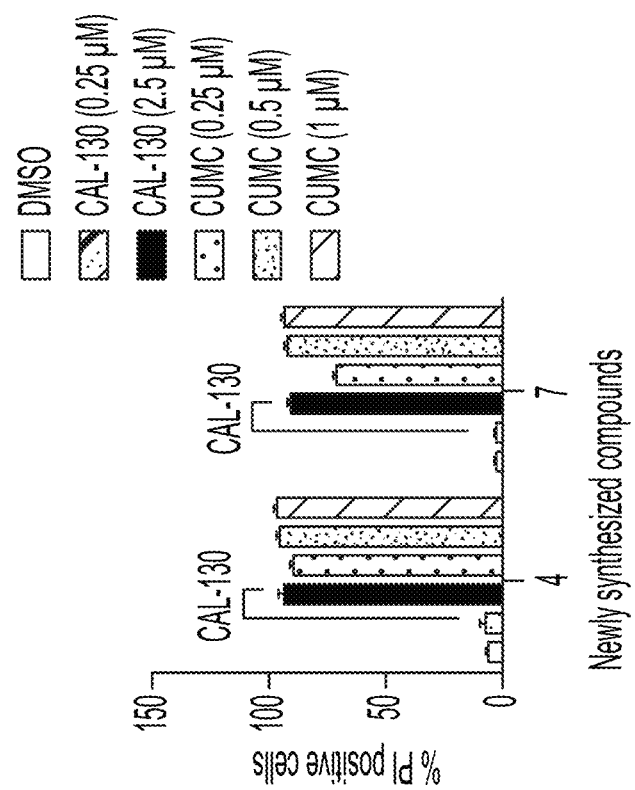
FIG. 4B shows effects of compounds DWL-PI3K-3 and DWL-PI3K-4 (respectively, Ex. Nos. 1-3 and 1-4 as described herein) on viability of the T-ALL cell line as compared to CAL-130.

The examples relate to representative compounds exhibiting improved properties over other PI3Kγ/δ inhibitors. For example, compounds described in Tables I, II, and III exhibit superior biological effects relative to other PI3Kγ/δ inhibitors. As described for example in FIG. 4, compounds such as I-50, DWL-PI3K-1, -2, -3, -4, -5, -6, and -7, and in particular DWL-PI3K-5, -6, and -7, have better pharmaco- kinetics and about 10-fold less may be needed relative to CAL-130 to achieve a similar reduction in tumor cell survival. Compounds described herein also appear to be selective for p110 catalytic domains of PI3Kγ and PI3Kδ as treatment, for example, of a T-ALL cell line lacking these two p110 isoforms results in limited cell killing.

Example 1: DWL-PI3K-1

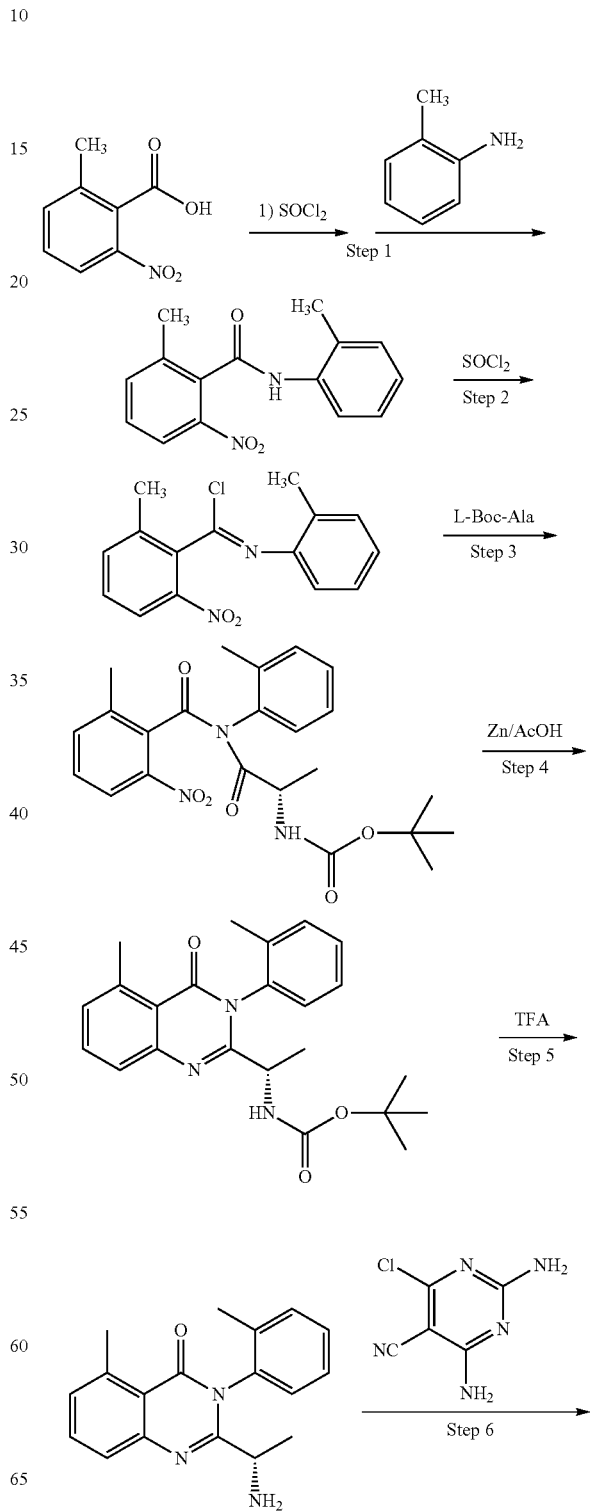

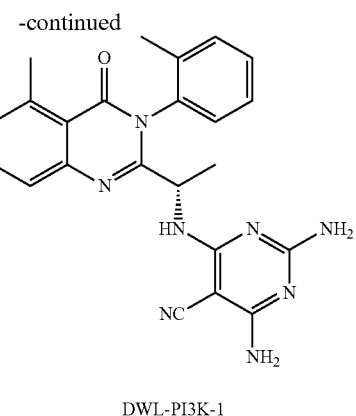

DWL-PI3K-1

Step 1: Synthesis of 2-methyl-6-nitro-N-(o-tolyl)benzamide. A mixture of 2-methyl-6-nitrobenzoic acid (4.0 g, 22.0 mmol), toluene (20 mL) and thionyl chloride (SOCl$_2$) (10 g, 84 mmol) was heated at reflux for 2 h. The reaction was then concentrated at 45° C. under reduced pressure, and THF (30 mL) was added to the resulting acid chloride. With cooling in an ice/water bath, N,N-diisopropylethylamine (10 mL) and o-toluidine (2.4 g, 22.4 mmol) were added. The reaction mixture was stirred at room temperature overnight. The mixture was then concentrated under reduced pressure, and the residue was dissolved in EtOAc (50 mL). This solution was washed with 1N HCl (2×20 mL) and an aqueous saturated NaHCO$_3$ solution (2×20 mL) and concentrated in vacuo to afford 2-methyl-6-nitro-N-(o-tolyl)benzamide as an off-white solid (5.94 g, yield: 100%).

Step 2: Synthesis of 2-methyl-6-nitro-N-(o-tolyl)benzimidoyl chloride. A mixture of 2-methyl-6-nitro-N-(o-tolyl)benzamide (3.0 g, 11 mmol), toluene (20 mL), thionyl chloride (6.0 mL) and DMF (40 µL) was refluxed for 2.5 h. The resulting solution was concentrated under reduced pressure at 45° C. to afford the crude product as a yellow oil (3.08 g, used without further purification).

Step 3: Synthesis of tert-butyl (S)-(1-(2-methyl-6-nitro-N-(o-tolylbenzamido)-1-oxopropan-2-yl)carbamate. The crude product (3.08 g), prepared in step 2 (2-methyl-6-nitro-N-(o-tolyl)benzimidoyl chloride), was dissolved in CH$_2$Cl$_2$ (8.0 mL) and added to a solution of Boc-L-alanine (1.9 g, 17.4 mmol) and N,N-diisopropylethylamine (3 mL) in CH$_2$Cl$_2$ (10 mL) at 0-5° C. The reaction mixture was stirred for 1 h at this temperature and then warmed to room temperature overnight. The resulting solution was washed with 10% aqueous citric acid (2×15 mL) followed by saturated aqueous NaHCO$_3$ (10 mL), and concentrated in vacuo. Purification by flash chromatography on silica gel eluting with 20% ethyl acetate in hexanes afforded the desired product as a solid (3.22 g, yield: yield: 67%). MS: m/z=442 (M+1).

Step 4: Synthesis of tert-butyl (S)-(1-(5-methyl-4-oxo-3-(o-tolyl)-3,4-dihydroquinazolin-2-yl)ethyl)carbamate. A suspension of zinc powder (4.8 g) in acetic acid (30 mL) and tert-butyl (S)-(1-(2-methyl-6-nitro-N-(o-tolylbenzamido)-1-oxopropan-2-yl)carbamate (3.22 g, 7.3 mmol, prepared in Step 3) was stirred at room temperature for 4 h. The mixture was concentrated in vacuo, and the resulting residue was dissolved in CH$_2$Cl$_2$ (40 mL). The solution was washed with saturated aqueous NaHCO$_3$ (2×10 mL) and concentrated in vacuo. The residue was purified by chromatography on silica gel (20% ethyl acetate in hexanes) to afford the product as a white solid (822 mg, yield 28.6%). MS: m/z=394 (M+1).

Step 5: Synthesis of (S)-2-(1-aminoethyl)-5-methyl-3-(o-tolyl)quinazolin-4(3H)-one. A mixture of tert-butyl (S)-(1-(5-methyl-4-oxo-3-(o-tolyl)-3,4-dihydroquinazolin-2-yl)ethyl)carbamate (822 mg, 2.1 mmol, prepared in Step 4) and trifluoroacetic acid (5 mL) in CH$_2$Cl$_2$ (20 mL) was stirred at room temperature overnight. The reaction mixture was concentrated in vacuo to provide the product in 100% yield as TFA salt (842 mg). MS: m/z=294 (M+1).

Step 6: Synthesis of (S)-2,4-diamino-6-((1-(5-methyl-4-oxo-3-(o-tolyl)-3,4-dihydroquinazolin-2-yl)ethyl)amino)pyrimidine-5-carbonitrile (DWL-PI3K-1). A mixture of (S)-2-(1-aminoethyl)-5-methyl-3-(o-tolyl)quinazolin-4(3H)-one (12 mg, 0.4 mmol, prepared in step 5), 2,4-diamino-6-chloropyrimidine-5-carbonitrile (10 mg, 0.034 mmol), N,N-diisopropylethylamine (0.1 mL) and potassium fluoride (18 mg) in DMSO (1 mL) was heated at 90° C. for overnight. The reaction mixture was cooled to room temperature, and to the mixture, was added EtOAc (20 mL). The solution was washed with distilled water (3×5 mL), 1N HCl (aq), and saturated aqueous NaHCO$_3$ (2×5 mL). The solvent was evaporated in vacuo, and the crude product was purified via column chromatography on silica gel (EtOAc/MeOH 20:1) to provide the desired product, DWL-PI3K-1, as a white solid (4.8 mg, yield: 33%). MS: m/z=427 (M+1).

Example 2: DWL-PI3K-2

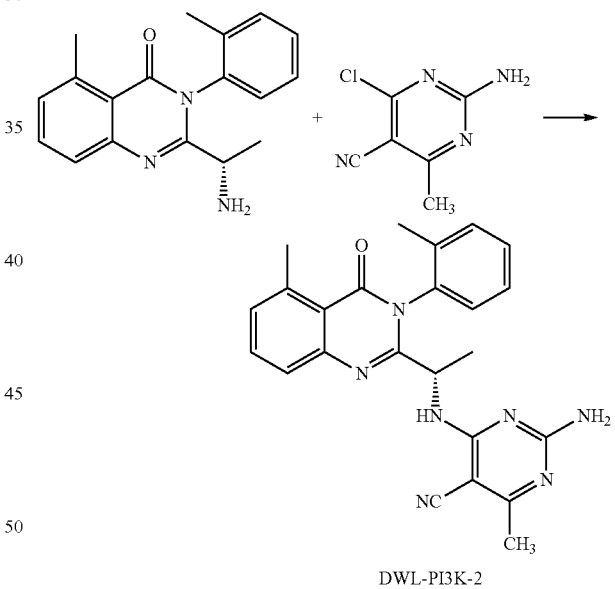

DWL-PI3K-2

Synthesis of (S)-2-amino-4-methyl-6-((1-(5-methyl-4-oxo-3-(o-tolyl)-3,4-dihydroquinazolin-2-yl)ethyl)amino)pyrimidine-5-carbonitrile (DWL-PI3K-2). A mixture of (S)-2-(1-aminoethyl)-5-methyl-3-(o-tolyl)quinazolin-4(3H)-one (133 mg, 0.45 mmol), 2-amino-4-chloro-6-methylpyrimidine-5-carbonitrile (86 mg, 0.51 mmol), N,N-diisopropylethylamine (0.2 mL) and potassium fluoride (96 mg) in DMSO (5 mL) was heated at 90° C. overnight. The reaction mixture was cooled to room temperature and EtOAc (20 mL) was added. The solution was washed with H$_2$O (3×5 mL), 1N HCl (aq), and saturated aqueous NaHCO$_3$ (2×5 mL), and was subsequently concentrated in vacuo. The crude product was purified via column chromatography on silica gel (EtOAc/MeOH 20:1) to provide the desired product, DWL-PI3K-2, as a white solid (115 mg, 60%). MS: m/z=426 (M+1).

Example 3: DWL-PI3K-3

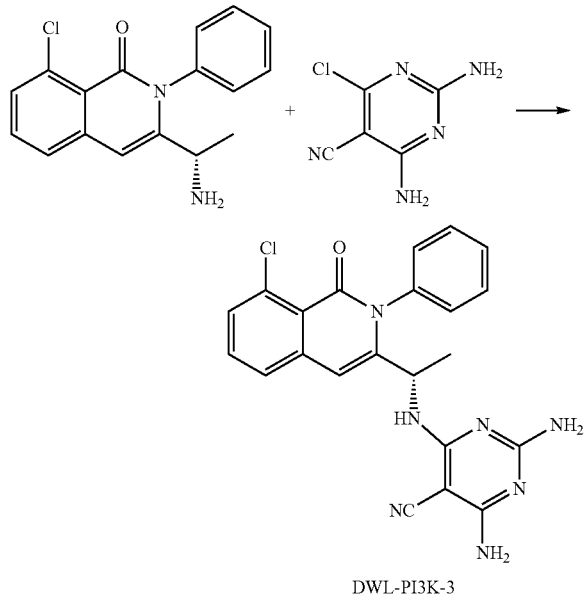

DWL-PI3K-3

Synthesis of (S)-2,4-diamino-6-((1-(8-chloro-1-oxo-2-phenyl-1,2-dihydroisoquinolin-3-yl)ethyl)amino)pyrimidine-5-carbonitrile (DWL-PI3K-3). A mixture of (S)-3-(1-aminoethyl)-8-chloro-2-phenylisoquinolin-1(2H)-one (23 mg, 0.077 mmol), 2,4-diamino-6-chloropyrimidine-5-carbonitrile (13 mg, 0.08 mmol), N,N-diisopropylethylamine (0.1 mL) and potassium fluoride (21 mg) in DMSO (1 mL) was heated at 90° C. overnight. The reaction mixture was cooled to room temperature and EtOAc (20 mL) was added. The solution was washed with H₂O (3×5 mL), and concentrated in vacuo. The crude product was purified via column chromatography on silica gel (EtOAc/MeOH 20:1) to provide the desired product, DWL-PI3K-3, as a white solid (23 mg, yield 70%). MS: m/z=432 (M+1).

Example 4: DWL-PI3K-4

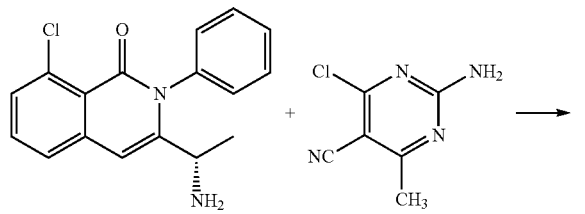

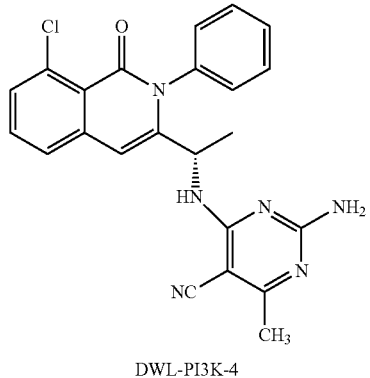

DWL-PI3K-4

Synthesis of (S)-2-amino-4-((1-(8-chloro-1-oxo-2-phenyl-1,2-dihydroisoquinolin-3-yl)ethyl)amino)-6-methylpyrimidine-5-carbonitrile (DWL-PI3K-4). A mixture of (S)-3-(1-aminoethyl)-8-chloro-2-phenylisoquinolin-1(2H)-one (23 mg, 0.077 mmol), 2-amino-4-chloro-6-methylpyrimidine-5-carbonitrile (13 mg, 0.08 mmol), N,N-diisopropylethylamine (0.1 mL) and potassium fluoride (21 mg) in DMSO (1 mL) was heated at 90° C. overnight. The reaction mixture was cooled to room temperature and EtOAc (20 mL) was added. The solution was washed with H₂O (3×5 mL), and concentrated in vacuo. The crude product was purified via column chromatography on silica gel (EtOAc/MeOH 20:1) to provide the desired product, DWL-PI3K-4, as a white solid (30 mg, 91% yield). MS: m/z=431 (M+1).

Example 5: DWL-PI3K-5

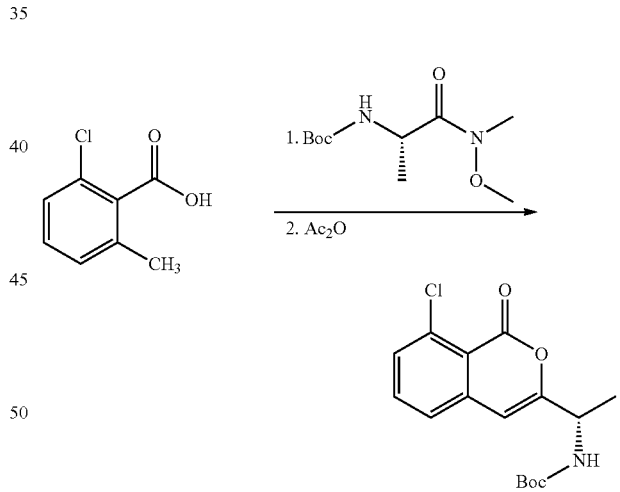

Synthesis of (S)-tert-butyl 1-(8-chloro-1-oxo-1H-isochromen-3-yl)ethylcarbamate. To the solution of 2-chloro-6-methylbenzoic acid (0.8 g, 4.7 mmol) in anhydrous THF (10 mL) was slowly added n-hexyllithium (8.8 mL, 2.3 M, 20.2 mmol) and the mixture was stirred at −20° C. for 20 min. In a separate flask, to the solution of (S)-tert-butyl 1-(methoxy(methyl)amino)-1-oxopropan-2-ylcarbamate (1.4 g, 6.1 mmol) in anhydrous THF (10 mL) was added iPrMgCl (6.33 mL, 2 M) and the mixture was stirred at −10° C. for 20 min. The resulting mixture was transferred to the above flask via cannula at −20° C. The resulting mixture was heated slowly to room temperature and kept at room temperature for 1.5 h. The reaction was quenched with water and acidified with 2N HCl (aq), and extracted with ethyl acetate (3×50 mL). The organic layer was dried and concentrated in vacuo. Column chromatography with 10% methanol in DCM provided the desired product. The product was dissolved in acetic anhydride (10 mL) and DMAP (10 mg) was added to the solution. The reaction mixture was kept at 70° C. for 2 h. The solvent was removed in vacuo, and the crude product was purified via column chromatography with 25% ethyl acetate in hexanes to provide (S)-tert-butyl 1-(8-chloro-1-oxo-1H-isochromen-3-yl)ethylcarbamate (1.3 g, 86%).

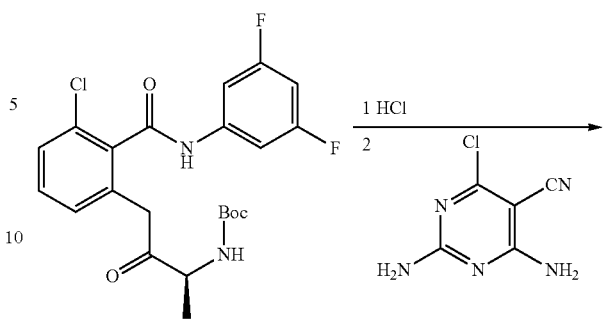

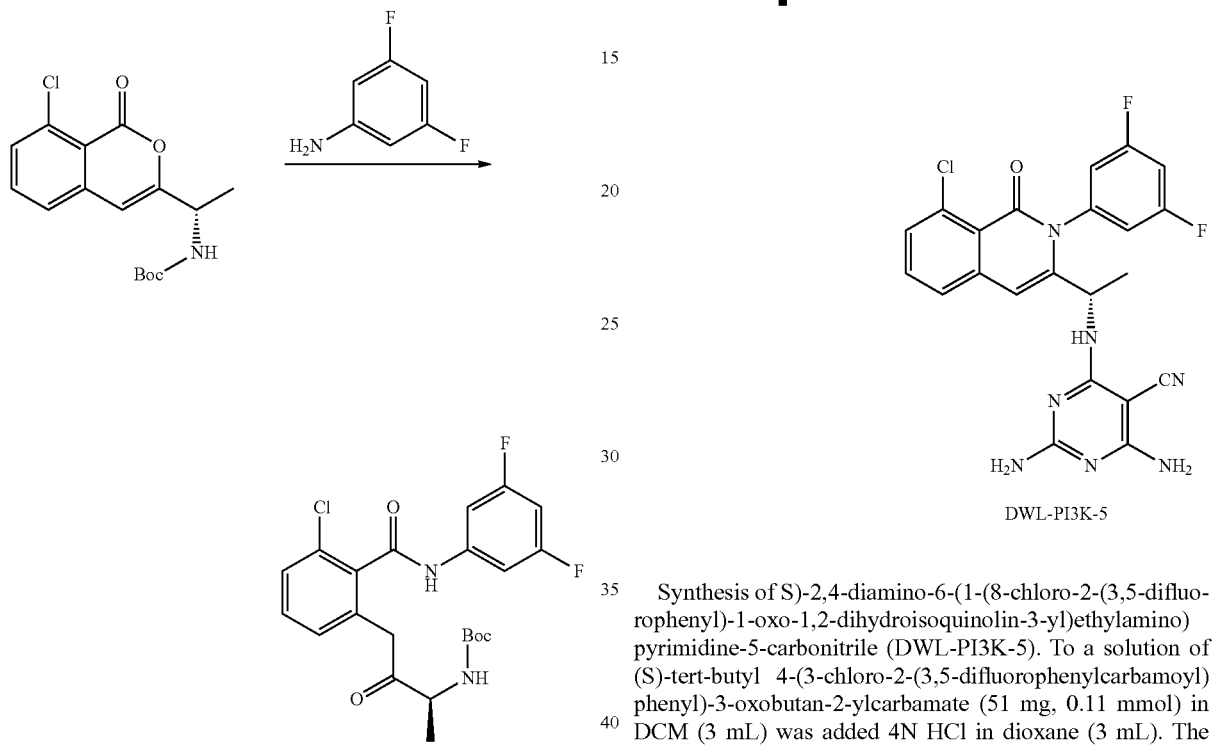

Synthesis of tert-butyl (S)-(4-(3-chloro-2-((3,5-difluorophenyl)carbamoyl)phenyl)-3-oxobutan-2-yl)carbamate. A solution of (S)-tert-butyl 1-(8-chloro-1-oxo-1H-isochromen-3-yl)ethylcarbamate (1.17 g, 3.62 mmol) in DCM (25 mL) was slowly added to a solution of 3,5-difluoroaniline (2.33 g, 18.1 mmol) and trimethylaluminum (9.05 mL, 2M, 18.1 mmol) in DCM (25 mL). The resulting mixture was stirred at room temperature for 2 h and slowly quenched with Rochelle salt. The organic phase was dried, concentrated in vacuo, and purified via column chromatography with 0-10% methanol in DCM to provide the product (1.53 g, 93.5%).

Synthesis of S)-2,4-diamino-6-(1-(8-chloro-2-(3,5-difluorophenyl)-1-oxo-1,2-dihydroisoquinolin-3-yl)ethylamino)pyrimidine-5-carbonitrile (DWL-PI3K-5). To a solution of (S)-tert-butyl 4-(3-chloro-2-(3,5-difluorophenylcarbamoyl)phenyl)-3-oxobutan-2-ylcarbamate (51 mg, 0.11 mmol) in DCM (3 mL) was added 4N HCl in dioxane (3 mL). The reaction mixture was stirred at room temperature for 2 h. The solvent was removed, and the crude product was dissolved in DMSO (1.2 mL). To the solution was added 2,4-diamino-6-chloropyrimidine-5-carbonitrile (23 mg) and DIPEA (0.1 mL). The resulting mixture was stirred at 125° C. overnight. The solvent was evaporated in vacuo, and the crude product was purified via preparative TLC with 12% methanol in DCM to provide the desired product, (S)-2,4-diamino-6-(1-(8-chloro-2-(3,5-difluorophenyl)-1-oxo-1,2-dihydroisoquinolin-3-yl)ethylamino)pyrimidine-5-carbonitrile (DWL-PI3K-5) (8.7 mg, 16.5%).

Example 6: DWL-PI3K-6

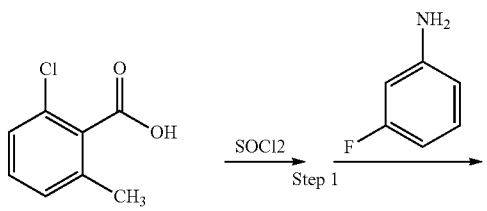

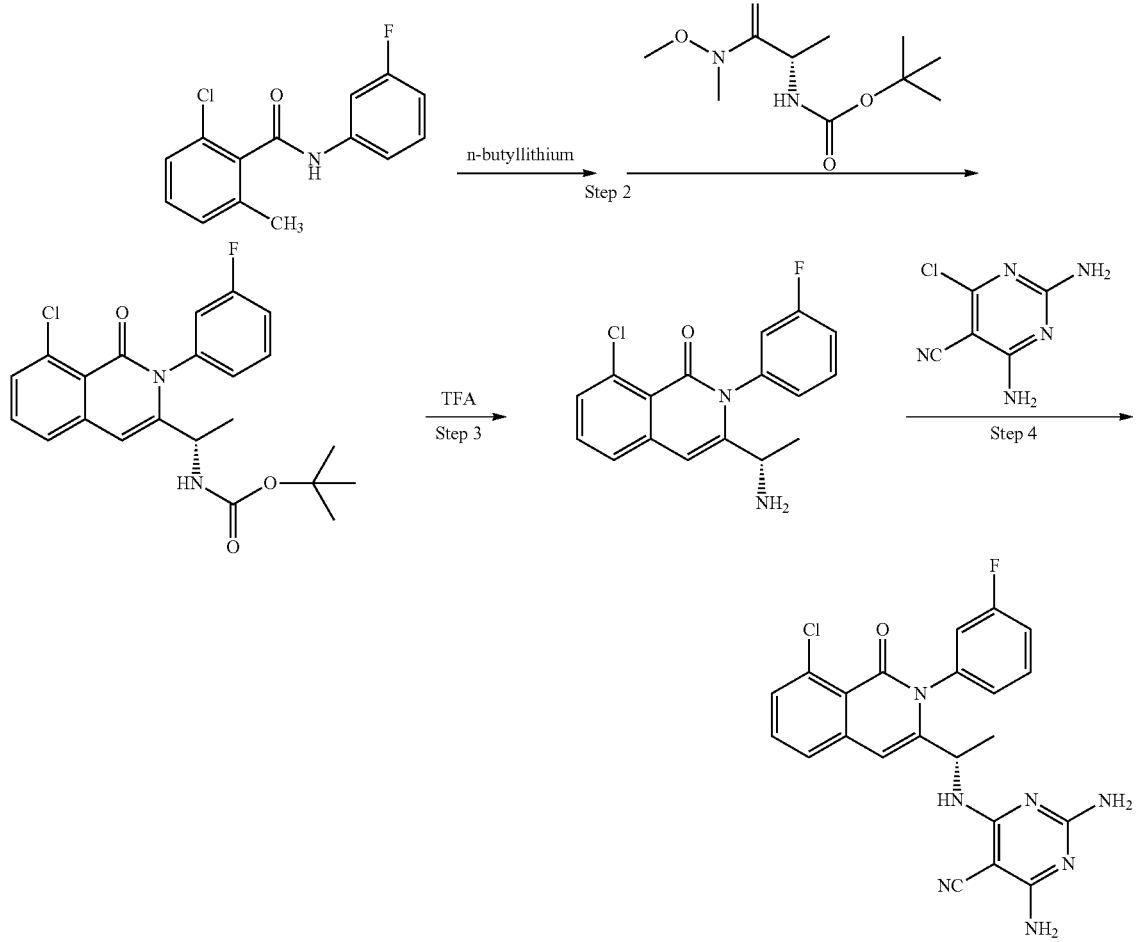

DWL-PI3K-6

Step 1: Synthesis of 2-chloro-N-(3-fluorophenyl)-6-methylbenzamide. A mixture of 2-chloro-6-methylbenzoic acid (7.5 g, 44 mmol), and thionyl chloride (30 mL) was heated at 70° C. for 3 h and concentrated at 45° C. under reduced pressure. The resulting acid chloride was dissolved in $CH_2Cl_2$ (30 mL) and mixed with 3-fluroaniline (8.3 g, 74.8 mmol) and trimethylamine (7.5 mL). The reaction mixture was stirred at room temperature overnight, then was concentrated under reduced pressure. The residue was dissolved in EtOAc (60 mL). The solution was washed with 2N HCl (aq) (2×20 mL) and saturated aqueous $NaHCO_3$ (2×20 mL) and concentrated in vacuo. The product was purified by chromatography to afford 2-chloro-N-(3-fluorophenyl)-6-methylbenzamide as a white solid (10.5 g, yield: 100%).

Step 2: Synthesis of tert-butyl (S)-(1-(8-chloro-2-(3-fluorophenyl)-1-oxo-1,2-dihydroisoquinolin-3-yl)ethyl)carbamate. To a mixture of 2-chloro-N-(3-fluorophenyl)-6-methylbenzamide (2.63 g, 10 mmol) in anhydrous THF (60 mL) at −30° C., stirred under argon, a solution of 2.5 M n-butyllithium in hexanes (2.6 mL, 2.5 eq) was added dropwise over 30 min. The resulting mixture was stirred at −30° C. for 30 min.

To a stirred mixture of tert-butyl (S)-(1-(methoxy(methyl) amino)-1-oxopropan-2-yl)carbamate (0.7 g, 1.5 eq) in anhydrous THF (30 mL) at −30° C., stirred under argon, a solution of isopropylmagnesium chloride in THF (3.2 mL, 1.65 eq) was added dropwise over 30 min at a temperature between −30° C. and −10° C. The resulting mixture was stirred at −30° C. for 30 min. This solution was then slowly added to the above reaction mixture while keeping the inner temperature between −30° C. and −10° C. The resulting mixture was stirred at −15° C. for 1 h, then was quenched with water (40 mL), and subsequently acidified with conc. HCl at −10° C. to 0° C. to adjust the pH to 1-3. The mixture was allowed to warm to room temperature and concentrated in vacuo. The residue was dissolved in MeOH (50 mL), and then conc. HCl (25 mL) was added. The resulting mixture was stirred at reflux for 1 h. The reaction mixture was concentrated in vacuo to reduce the volume to about 45 mL. The residue was extracted with a 2:1 mixture of heptane and ethyl acetate (2×60 mL). The aqueous layer was basified with concentrated ammonium hydroxide to adjust the pH to 9-10 while keeping the inner temperature between −10° C. and 0° C. The mixture was then extracted with $CH_2Cl_2$ (3×50 mL). The combined organic extracts were washed with brine. The solution is concentrated in vacuo. The product was purified by column chromatography with silica gel (EtOAc/MeOH 5:1) to afford tert-butyl (S)-(1-(8-chloro-2-(3-fluorophenyl)-1-oxo-1,2-dihydroisoquinolin-3-yl) ethyl)carbamate as a white solid (0.56 g, yield 13%). MS: m/z=417 (M+1).

Step 3: Synthesis of (S)-3-(1-aminoethyl)-8-chloro-2-(3-fluorophenyl)isoquinolin-1(2H)-one. A mixture of tert-butyl (S)-(1-(8-chloro-2-(3-fluorophenyl)-1-oxo-1,2-dihydroisoquinolin-3-yl)ethyl)carbamate (560 mg, 1.34 mmol, prepared in step 2) and trifluoroacetic acid (5 mL) in $CH_2Cl_2$ (20 mL) was stirred at room temperature overnight. The reaction mixture was concentrated in vacuo to afford the desired product, (S)-3-(1-aminoethyl)-8-chloro-2-(3-fluorophenyl)isoquinolin-1(2H)-one as a solid in quantitative yield. MS: m/z=317 (M+1).

Step 4: Synthesis of (S)-2,4-diamino-6-((1-(8-chloro-2-(3-fluorophenyl)-1-oxo-1,2-dihydroisoquinolin-3-yl)ethyl)amino)pyrimidine-5-carbonitrile (DWL-PI3K-6). A mixture of (S)-3-(1-aminoethyl)-8-chloro-2-(3-fluorophenyl)isoquinolin-1(2H)-one (59 mg, 0.18 mmol, prepared in step 3), 2,4-diamino-6-chloropyrimidine-5-carbonitrile (38 mg, 0.22 mmol), N,N-diisopropylethylamine (0.1 mL) and potassium fluoride (36 mg) in DMSO (3 mL) was heated at 90° C. overnight. The reaction mixture was cooled to room temperature and EtOAc (20 mL) was added. The solution was washed with $H_2O$ (3×5 mL), 1N HCl (aq), and saturated aqueous $NaHCO_3$ (2×5 mL). The organic extract was concentrated in vacuo. The crude product was purified via column chromatography on silica gel (EtOAc/MeOH 20:1) to provide the desired product, DWL-PI3K-6, as a white solid (21 mg, yield: 26%). MS: m/z=450 (M+1).

Example 7: DWL-PI3K-7

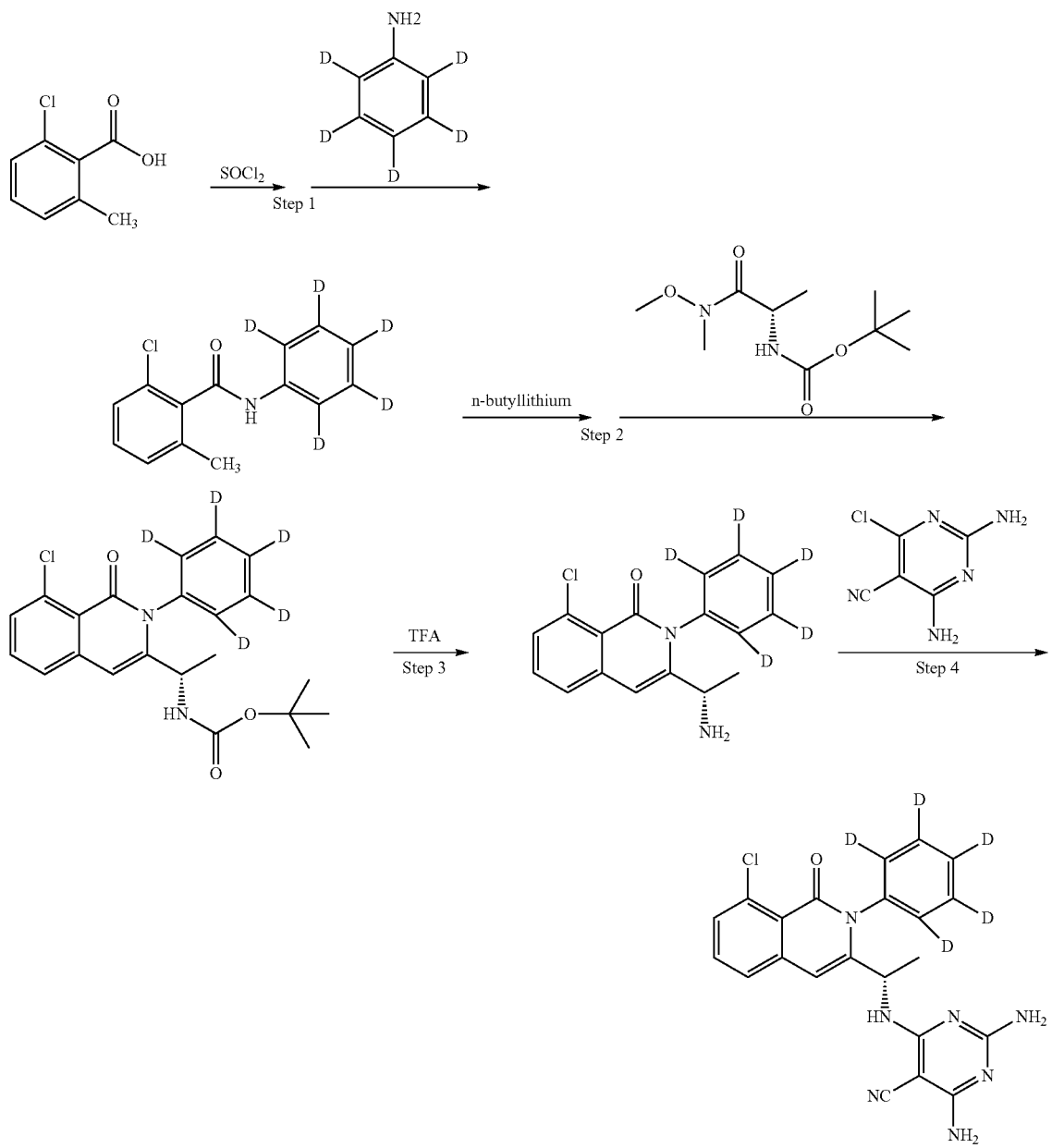

DWL-PI3K-7

Step 1: Synthesis of 2-chloro-6-methyl-N-(phenyl-d₅) benzamide. A mixture of 2-chloro-6-methylbenzoic acid (4.2 g, 24 mmol), and thionyl chloride (30 mL) was heated at 70° C. for 3 h and concentrated at 45° C. under reduced pressure. The resulting acid chloride was dissolved in $CH_2Cl_2$ (30 mL) and mixed with aniline-d₅ (2.0 g, 20 mmol) and triethylamine (4 mL, excess). The reaction mixture was stirred overnight at room temperature and was subsequently concentrated under reduced pressure. The residue was dissolved in EtOAc (60 mL) and washed with 2N HCl (aq) (2×20 mL) and saturated aqueous $NaHCO_3$ (2×20 mL). The solution was concentrated in vacuo to afford 2-chloro-6-methyl-N-(phenyl-d₅)benzamide as a solid (5.0 g, yield: 100%). MS: m/z=249 (M-1).

Step 2: Synthesis of tert-butyl (S)-(1-(8-chloro-1-oxo-2-(phenyl-d₅)-1,2-dihydroisoquinolin-3-yl)ethyl)carbamate. To a mixture of 2-chloro-6-methyl-N-(phenyl-d₅)benzamide (630 mg, 2.5 mmol) in anhydrous THF (30 mL) at −30° C., stirred under argon, a solution of 2.5 M n-butyllithium in hexanes (10 mL, 2.5 eq) was added dropwise over 30 min while keeping the temperature at −30° C. The resulting mixture was then stirred at −30° C. for 30 min. To a stirred mixture of tert-butyl (S)-(1-(methoxy(methyl)amino)-1-oxopropan-2-yl)carbamate (2.7 g, 1.5 eq) in anhydrous THF (60 mL) at −30° C., stirred under argon, a solution of isopropylmagnesium chloride in THF (12.4 mL, 1.65 eq) was added dropwise over 30 min while keeping the inner temperature between −30° C. and −10° C. The resulting mixture was stirred at −30° C. for 30 min. This solution was then slowly added to the above reaction mixture while keeping the inner temperature between −30° C. and −10° C. The resulting mixture was stirred at −15° C. for 1 h, then was quenched with water (50 mL) and acidified with conc. HCl at −10° C. to 0° C. to adjust the pH to 1-3. The mixture was allowed to warm to room temperature and was concentrated in vacuo. The residue was dissolved in MeOH (50 mL), and then conc. HCl (25 mL) was added. The resulting mixture was stirred at reflux for 1 h. The reaction mixture was concentrated in vacuo to reduce the volume to about 45 mL. The residue was extracted with a 2:1 mixture of heptane and ethyl acetate (2×20 mL). The aqueous layer was basified with concentrated ammonium hydroxide to adjust the pH to 9-10 while keeping the inner temperature between −10° C. and 0° C. The mixture was then extracted with $CH_2Cl_2$ (3×20 mL) and was washed with brine. The solution was concentrated in vacuo. The product was purified via column chromatography with silica gel (EtOAc/MeOH 10:1) to afford tert-butyl (S)-(1-(8-chloro-1-oxo-2-(phenyl-d₅)-1,2-dihydroisoquinolin-3-yl)ethyl)carbamate as a white solid (140 mg, yield: 13.9%). MS: m/z=404 (M+1).

Step 3: Synthesis of (S)-3-(1-aminoethyl)-8-chloro-2-(phenyl-d₅)isoquinolin-1(2H)-one. A mixture of tert-butyl (S)-(1-(8-chloro-1-oxo-2-(phenyl-d₅)-1,2-dihydroisoquinolin-3-yl)ethyl)carbamate (140 mg. 0.34 mmol), prepared in Step 2, and trifluoroacetic acid (5 mL) in $CH_2Cl_2$ (20 mL) was stirred at room temperature overnight. The reaction mixture was concentrated in vacuo to provide the desired product in quantitative yield. (S)-3-(1-aminoethyl)-8-chloro-2-(phenyl-d₅)isoquinolin-1(2H)-one. MS: m/z=304 (M+1).

Step 4: Synthesis of (S)-2,4-diamino-6-((1-(8-chloro-1-oxo-2-(phenyl-d₅)-1,2-dihydroisoquinolin-3-yl)ethyl) amino)pyrimidine-5-carbonitrile (DWL-PI3K-7). A mixture of (S)-3-(1-aminoethyl)-8-chloro-2-(phenyl-d₅)isoquinolin-1(2H)-one (45 mg, 0.15 mmol), prepared in Step 3, 2,4-diamino-6-chloropyrimidine-5-carbonitrile (38 mg, 0.22 mmol), N,N-diisopropylethylamine (0.1 mL) and potassium fluoride (36 mg) in DMSO (3 mL) was heated at 90° C. overnight. The reaction mixture was cooled to room temperature and EtOAc (20 mL) was added. The solution was washed with $H_2O$ (3×10 mL), 1N HCl (aq) and saturated aqueous $NaHCO_3$ (2×5 mL). The organic extract was concentrated in vacuo. The crude product was purified by column chromatography with silica gel (EtOAc/MeOH 20:1) to provide the desired product, DWL-PI3K-7, as a white solid (23 mg, yield 35%). MS: m/z=437 (M+1).

Example 8

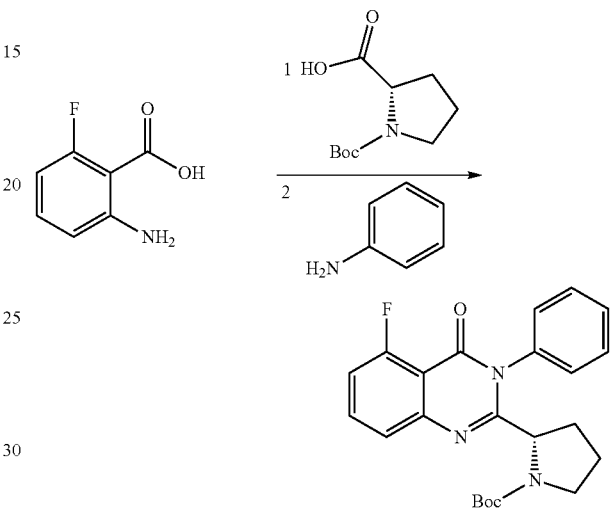

Synthesis of tert-butyl (S)-2-(5-fluoro-4-oxo-3-phenyl-3,4-dihydroquinazolin-2-yl)pyrrolidine-1-carboxylate. To the solution of 2-amino-6-fluorobenzoic acid (0.5 g, 3.22 mmol) and (S)-1-(tert-butoxycarbonyl)pyrrolidine-2-carboxylic acid (0.69 g, 3.22 mmol) in pyridine (3 mL) was added triphenylphosphite (2.11 mL, 8.05 mmol). The reaction mixture was heated to 70° C. and kept at said temperature for 2 h. Aniline (0.35 mL, 3.9 mmol) was added to the above mixture, which was then stirred for 8 h. The reaction mixture was diluted with ethyl acetate and washed with aqueous sodium bicarbonate, water, and brine, dried over sodium sulfate and concentrated in vacuo. Column chromatography with 25% ethyl acetate in hexanes provided the product (0.99 g, 75%).

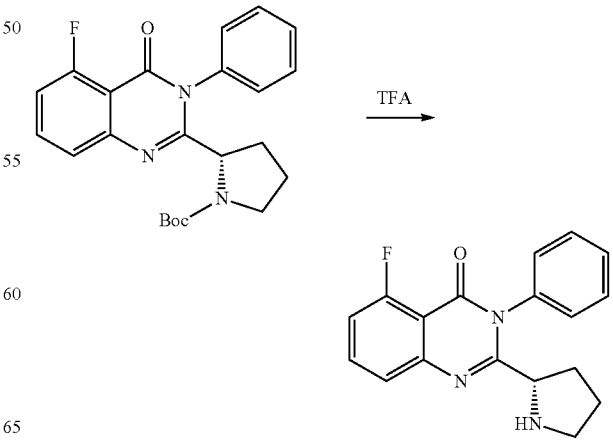

Synthesis of (S)-5-fluoro-3-phenyl-2-(pyrrolidin-2-yl)quinazolin-4(3H)-one. The above product, tert-butyl (S)-2-(5-fluoro-4-oxo-3-phenyl-3,4-dihydroquinazolin-2-yl)pyrrolidine-1-carboxylate was dissolved in DCM/TFA (ratio 2:1) and the reaction mixture was stirred at room temperature for 1 h and then concentrated to provide the product, (S)-5-fluoro-3-phenyl-2-(pyrrolidin-2-yl)quinazolin-4(3H)-one, in quantitative yield.

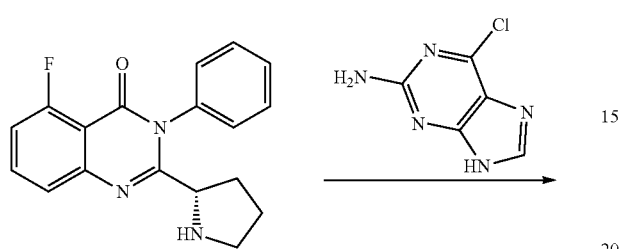

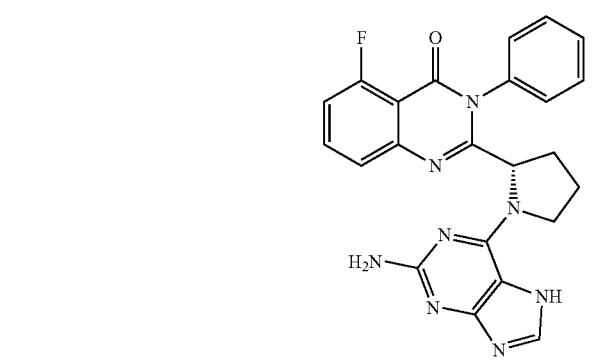

Synthesis of (S)-2-(1-(2-amino-7H-purin-6-yl)pyrrolidin-2-yl)-5-fluoro-3-phenylquinazolin-4(3H)-one. To the solution of (S)-5-fluoro-3-phenyl-2-(pyrrolidin-2-yl)quinazolin-4(3H)-one (0.07 mmol) in DMF (0.5 mL) was added 2-amino-6-chloropurine and N,N-diisopropylethylamine (0.04 mL) and the reaction was stirred at 150° C. for 1 h under argon. The solvent was removed and the crude product was purified via preparative TLC with 10% methanol in dichloromethane to provide the product, (S)-2-(1-(2-amino-7H-purin-6-yl)pyrrolidin-2-yl)-5-fluoro-3-phenylquinazolin-4(3H)-one (18.9 mg, 60%).

Example 8

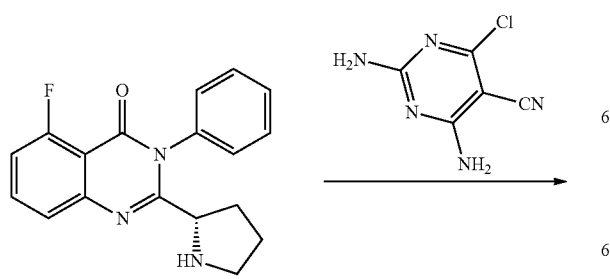

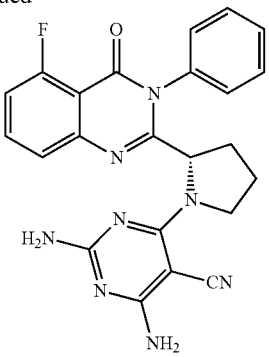

Synthesis of (S)-2,4-diamino-6-(2-(5-fluoro-4-oxo-3-phenyl-3,4-dihydroquinazolin-2-yl)pyrrolidin-1-yl)pyrimidine-5-carbonitrile. To the solution of (S)-5-fluoro-3-phenyl-2-(pyrrolidin-2-yl)quinazolin-4(3H)-one (0.06 mmol) in DMF (0.5 mL) was added 2,4-diamino-6-chloropyrimidine-5-carbonitrile (10.2 mg) and DIPEA (0.031 mL, 0.18 mmol), and the resulting mixture was stirred at 125° C. for 2 h under argon. The solvent was then removed in vacuo, and the crude mixture was purified via preparative TLC with 10% methanol in dichloromethane to give the product, (S)-2,4-diamino-6-(2-(5-fluoro-4-oxo-3-phenyl-3,4-dihydroquinazolin-2-yl)pyrrolidin-1-yl)pyrimidine-5-carbonitrile (20.9 mg, 79%).

Example 9

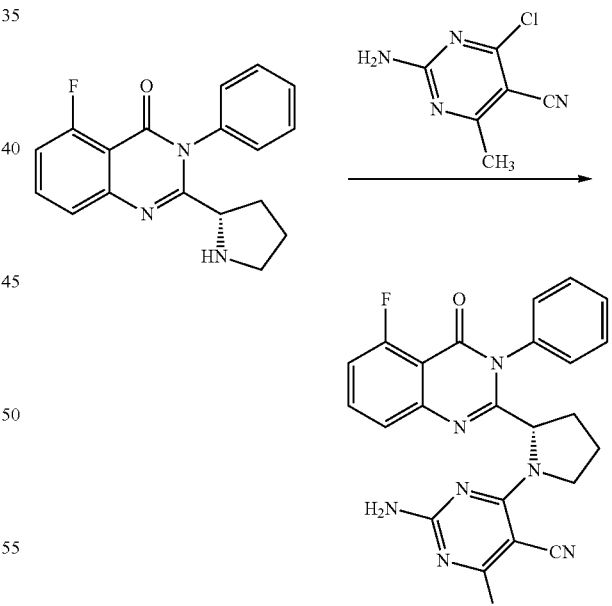

Synthesis of (S)-2-amino-4-(2-(5-fluoro-4-oxo-3-phenyl-3,4-dihydroquinazolin-2-yl)pyrrolidin-1-yl)-6-methylpyrimidine-5-carbonitrile. To the solution of (S)-5-fluoro-3-phenyl-2-(pyrrolidin-2-yl)quinazolin-4(3H)-one (0.06 mmol) in DMF (0.5 mL) was added 2-amino-4-chloro-6-methylpyrimidine-5-carbonitrile (10.1 mg) and DIPEA (0.031 mL, 0.18 mmol), and the resulting mixture was stirred at 125° C. for 2 h under argon. The solvent was then removed, and the crude mixture was purified via preparative TLC with 10% methanol in dichloromethane to give the product, (S)-2-amino-4-(2-(5-fluoro-4-oxo-3-phenyl-3,4-dihydroquinazolin-2-yl)pyrrolidin-1-yl)-6-methylpyrimidine-5-carbonitrile (22.2 mg, 84%).

Example 10: PI3K Inhibition

The compounds shown below were tested for inhibition of PI3Kα, PI3Kβ, PI3Kγ, and PI3Kδ:

DWL-PI3K-1
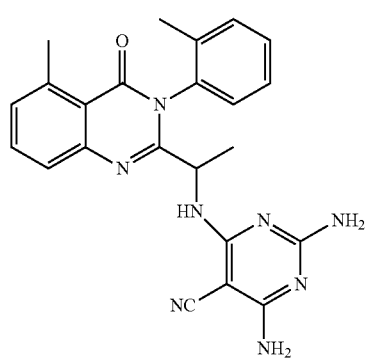

DWL-PI3K-2
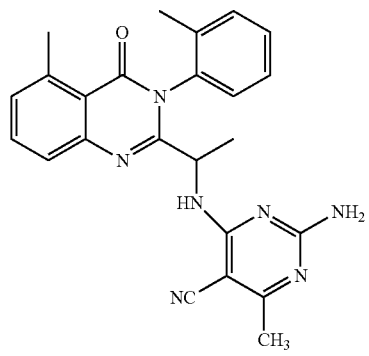

DWL-PI3K-3
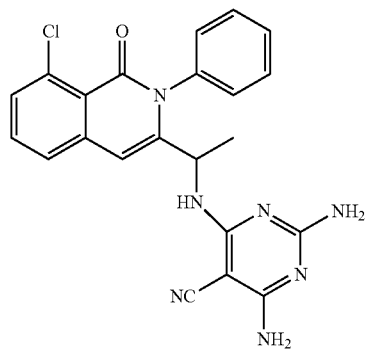

DWL-PI3K-4
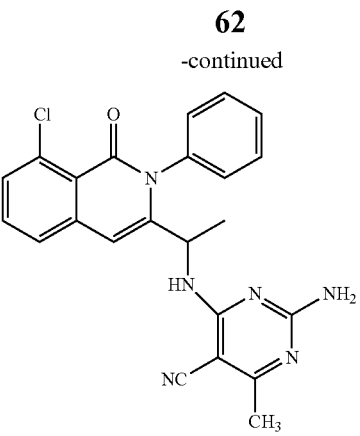

DWL-PI3K-5
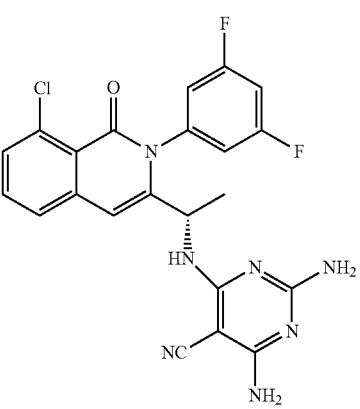

DWL-PI3K-6
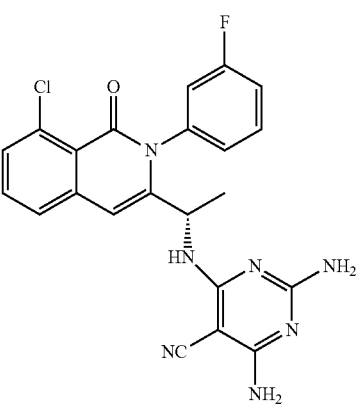

DWL-PI3K-7
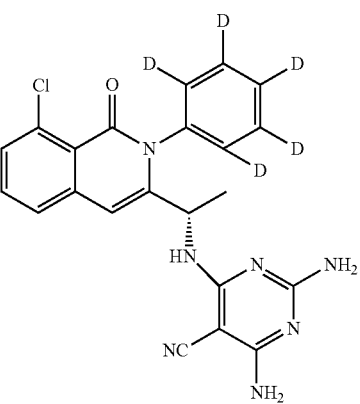

The compounds were tested using KINOMEscan™ (DiscoverX), which is based on a competition binding assay that quantitatively measures the ability of a compound to compete with an immobilized, active-site directed ligand. The assay is performed by combining three components: DNA-tagged kinase; immobilized ligand; and a test compound. The ability of the test compound to compete with the immobilized ligand is measured via quantitative PCR of the DNA tag.

For most assays, kinase-tagged T7 phage strains were prepared in an E. coli host derived from the BL21 strain. E. coli were grown to log-phase and infected with T7 phage and incubated with shaking at 32° C. until lysis. The lysates were centrifuged and filtered to remove cell debris. The remaining kinases were produced in HEK-293 cells and subsequently tagged with DNA for qPCR detection. Strepta-vidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific binding. Binding reactions were assembled by combining kinases, liganded affinity beads, and test compounds in 1× binding buffer (20% SeaBlock, 0.17×PBS, 0.05% Tween 20, 6 mM DTT). Test compounds were prepared as 111× stocks in 100% DMSO. Kds were determined using an 11-point 3-fold compound dilution series with three DMSO control points. All compounds for Kd measurements are distributed by acoustic transfer (non-contact dispensing) in 100% DMSO. The compounds were then diluted directly into the assays such that the final concentration of DMSO was 0.9%. All reactions performed in polypropylene 384-well plate. Each was a final volume of 0.02 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 μM non-biotinylated affinity ligand) and incubated at room temperature with shaking for 30 minutes. The kinase concentration in the eluates was measured by qPCR.

An 11-point 3-fold serial dilution of each test compound was prepared in 100% DMSO at 100× final test concentration and subsequently diluted to 1× in the assay (final DMSO concentration=1%). Most Kds were determined using a compound top concentration=30,000 nM. If the initial Kd determined was <0.5 nM (the lowest concentration tested), the measurement was repeated with a serial dilution starting at a lower top concentration. A Kd value reported as 40,000 nM indicates that the Kd was determined to be >30,000 nM.

Binding constants (Kds) were calculated with a standard dose-response curve using the Hill equation:

$$\text{Response} = \frac{\text{Background} + (\text{Signal} - \text{Background})}{1 + (Kd^{Hill\ Slope} / Dose^{Hill\ Slope})}$$

The Hill Slope was set to −1. Curves were fitted using a non-linear least square fit with the Levenberg-Marquardt algorithm. Table 4 below shows the results found for these compounds, where PIK3CA is PI3Kα, PIK3CB is PI3Kβ, PIK3CD is PI3Kγ, and PIK3CG is PI3Kδ:

| Compound Name | DiscoveRx Gene Symbol | Kd (nM) |
|---|---|---|
| DWL-PI3K-1 | PIK3CA | 20 |
| DWL-PI3K-1 | PIK3CB | 0.92 |
| DWL-PI3K-1 | PIK3CD | 0.39 |
| DWL-PI3K-1 | PIK3CG | 0.2 |
| DWL-PI3K-2 | PIK3CA | 53 |
| DWL-PI3K-2 | PIK3CB | 4.3 |
| DWL-PI3K-2 | PIK3CD | 0.62 |
| DWL-PI3K-2 | PIK3CG | 0.62 |
| DWL-PI3K-3 | PIK3CA | 4 |
| DWL-PI3K-3 | PIK3CB | 0.084 |
| DWL-PI3K-3 | PIK3CD | 0.14 |
| DWL-PI3K-3 | PIK3CG | 0.12 |
| DWL-PI3K-4 | PIK3CA | 2.2 |
| DWL-PI3K-4 | PIK3CB | 0.15 |
| DWL-PI3K-4 | PIK3CD | 0.042 |
| DWL-PI3K-4 | PIK3CG | 0.089 |
| DWL-PI3K-5 | PIK3CA | 30 |
| DWL-PI3K-5 | PIK3CB | 1.4 |
| DWL-PI3K-5 | PIK3CD | 0.12 |
| DWL-PI3K-5 | PIK3CG | 0.38 |
| DWL-PI3K-6 | PIK3CA | 10 |
| DWL-PI3K-6 | PIK3CB | 0.46 |
| DWL-PI3K-6 | PIK3CD | 0.11 |
| DWL-PI3K-6 | PIK3CG | 0.27 |
| DWL-PI3K-7 | PIK3CA | 6.1 |
| DWL-PI3K-7 | PIK3CB | 0.3 |
| DWL-PI3K-7 | PIK3CD | 0.12 |
| DWL-PI3K-7 | PIK3CG | 0.17 |

Example 11: Cell Assays

Compounds DWL-PI3K-1, DWL-PI3K-2, DWL-PI3K-3, DWL-PI3K-4, DWL-PI3K-5, DWL-PI3K-6 and DWL-PI3K-7, and reference compounds CAL-130, tenalisib, duvelisib were evaluated for efficacy (cell viability by measuring ATP (CellTiter-Glo) or propidium iodide (PI) uptake) against a number of cancer cells, including LMO-2-007, OCI-LY-10, HH, H9, PF382 and CCRF-CEM. The results are shown in FIGS. 7-14 and 17-20.

Example 12: DWL-PI3K-3 Treated

Figure 16:
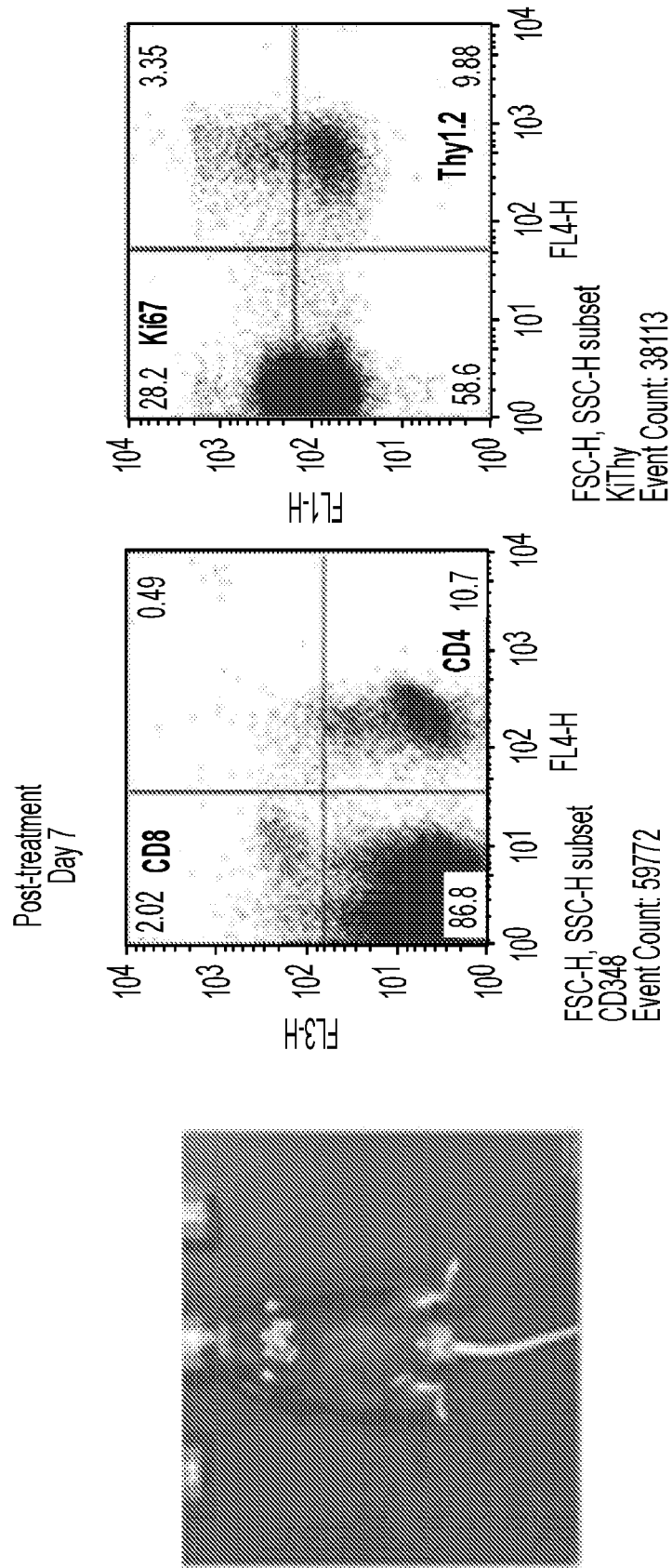
Figure 17:
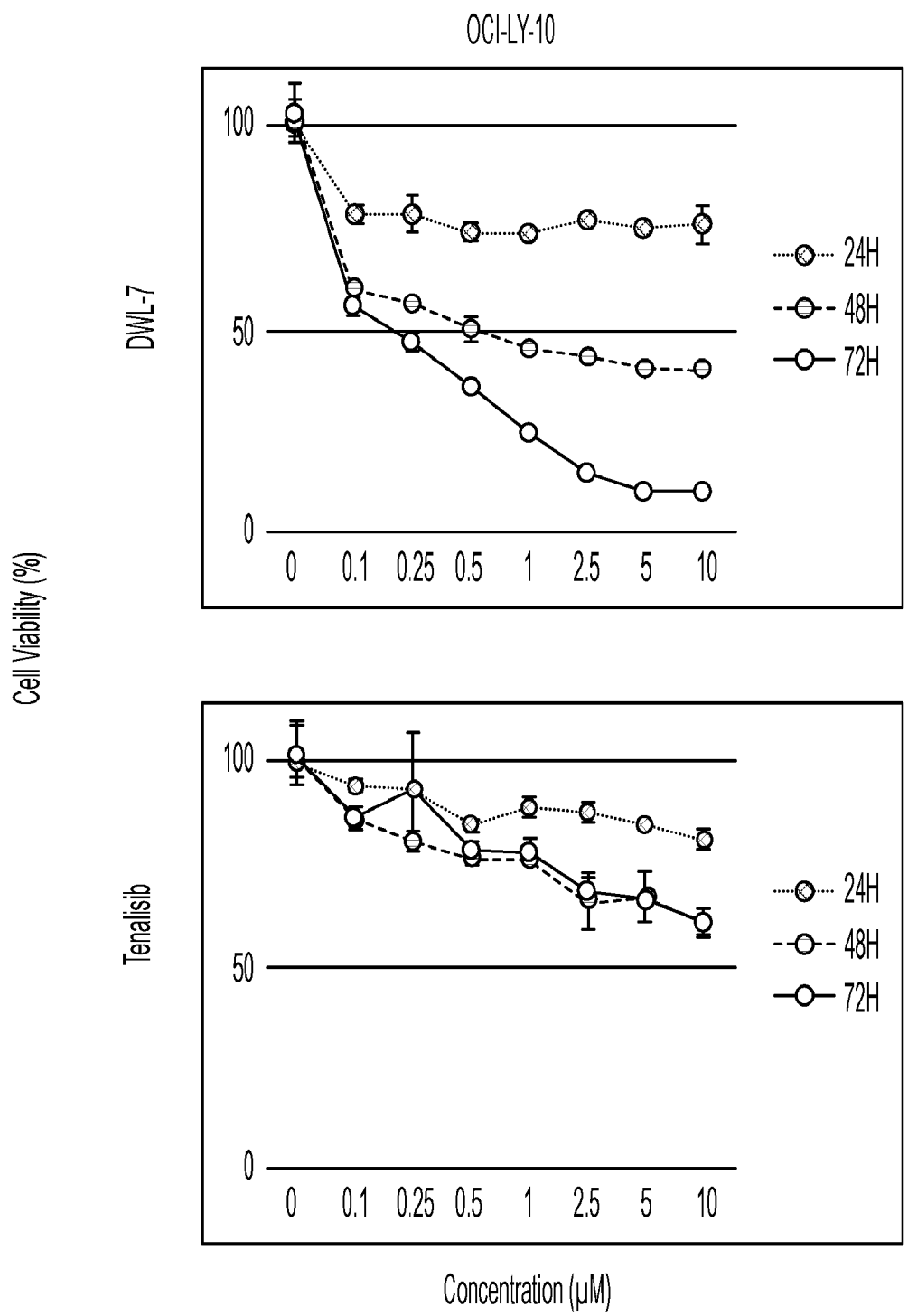
FIG. 17 contains charts comparing DWL-PI3K-7 to tenalisib in a cell viability assay for PI3Kγ/δ inhibitors (CellTiter-Glo) using aggressive B cell lymphoma cells (OCI-LY-10).
Figure 18:
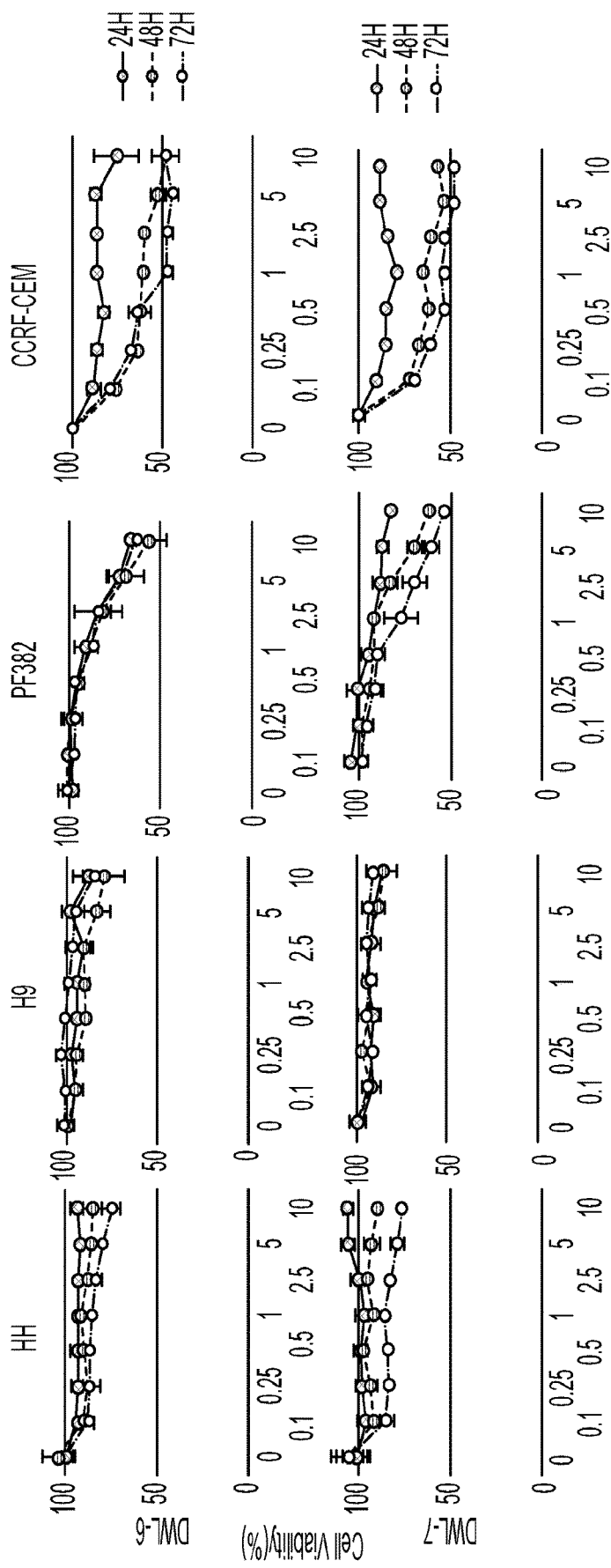
FIG. 18 contains charts comparing DWL-PI3K-6 and DWL-PI3K-7 to duvelisib and tenalisib in a cell viability assay for PI3Kγ/δ inhibitors (CellTiter-Glo) using CTCL lines (HH and H9) or T-ALL lines (PF382 and CCRF-CEM).
Figure 18:
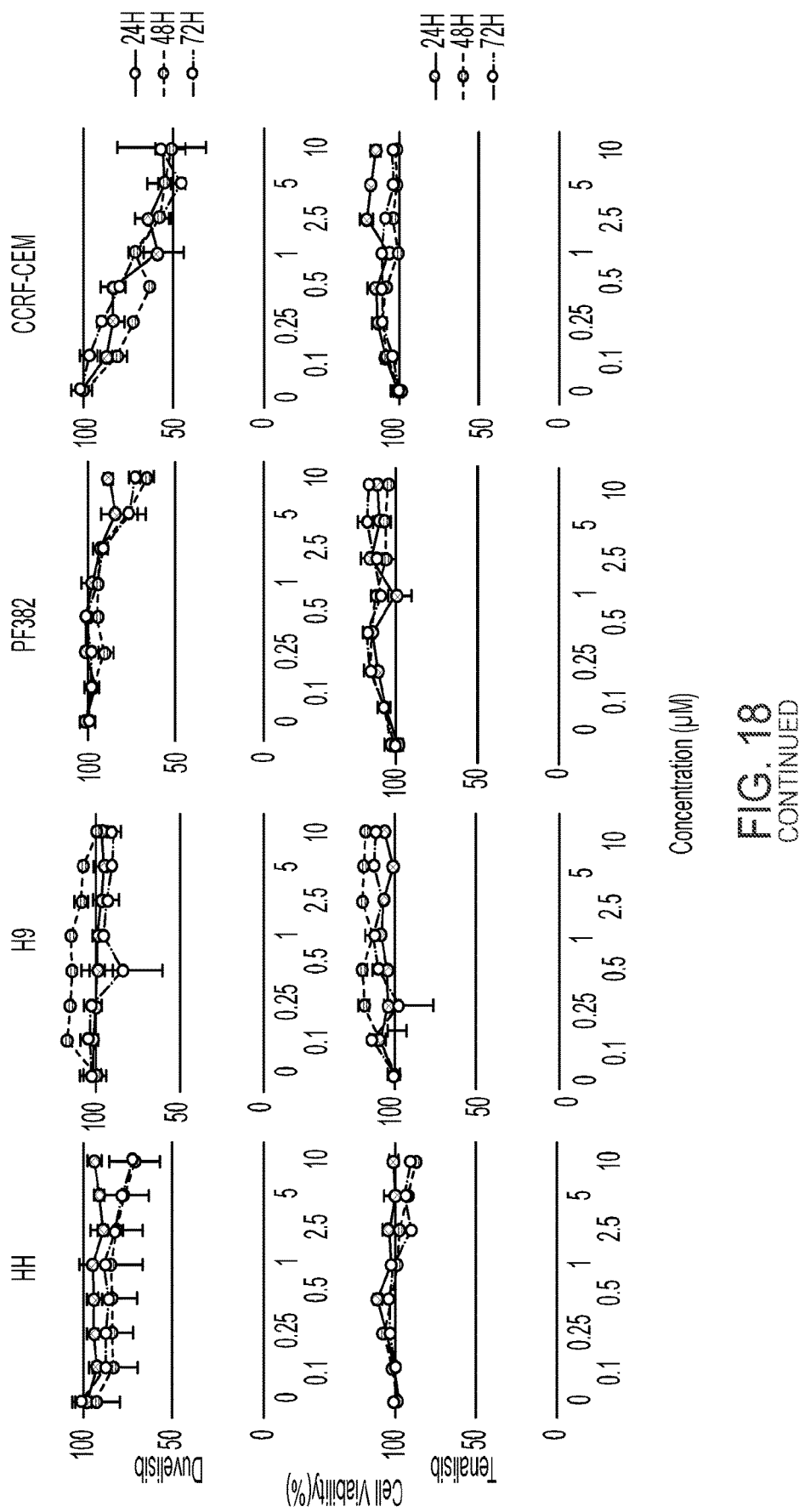
Figure 19:
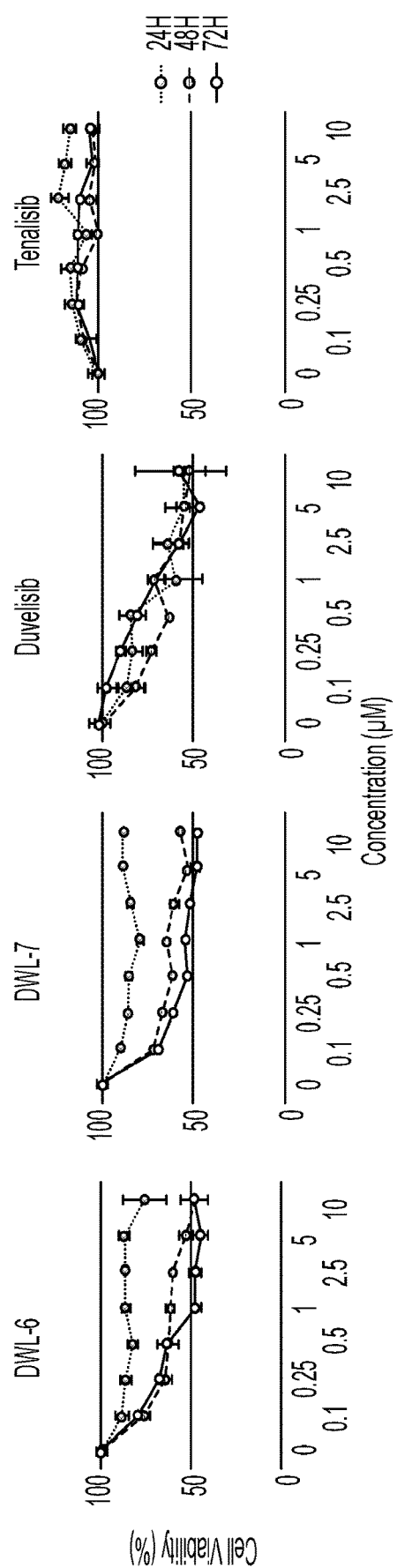
FIG. 19 compares results of a viability assay in T-ALL CCRF-CEM cell line (CellTiter-Glo) for DWL-PI3K-6, DWL-PI3K-7, duvelisib, and tenalisib.
Figure 19:
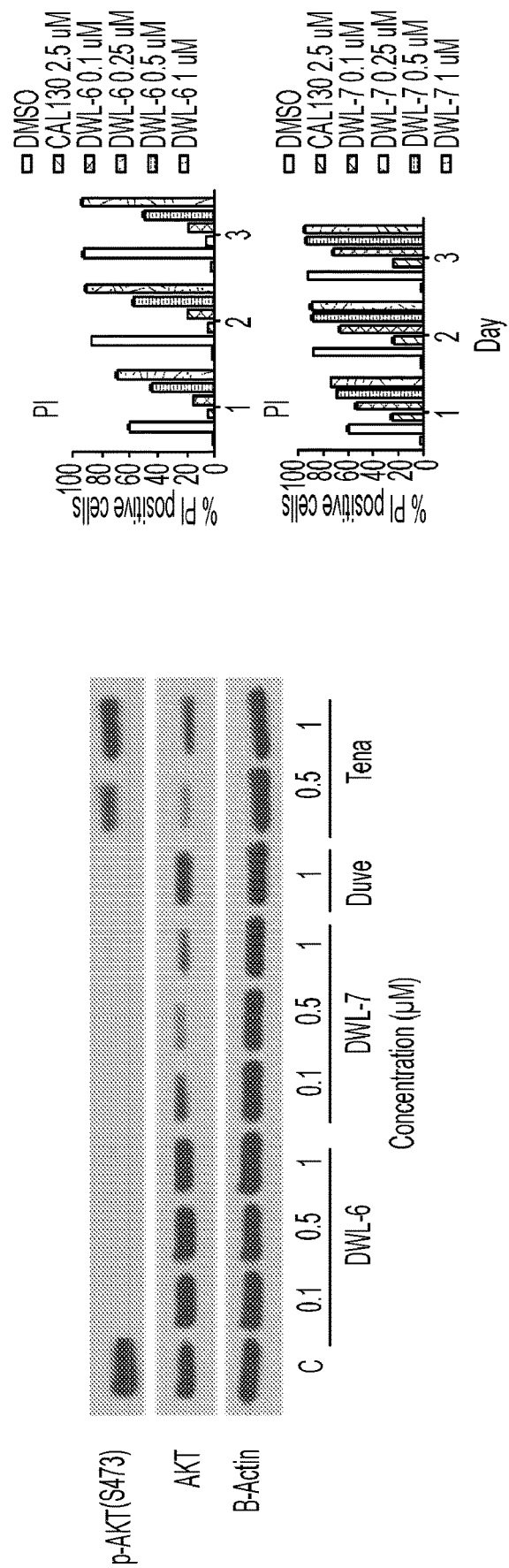
Figure 20:
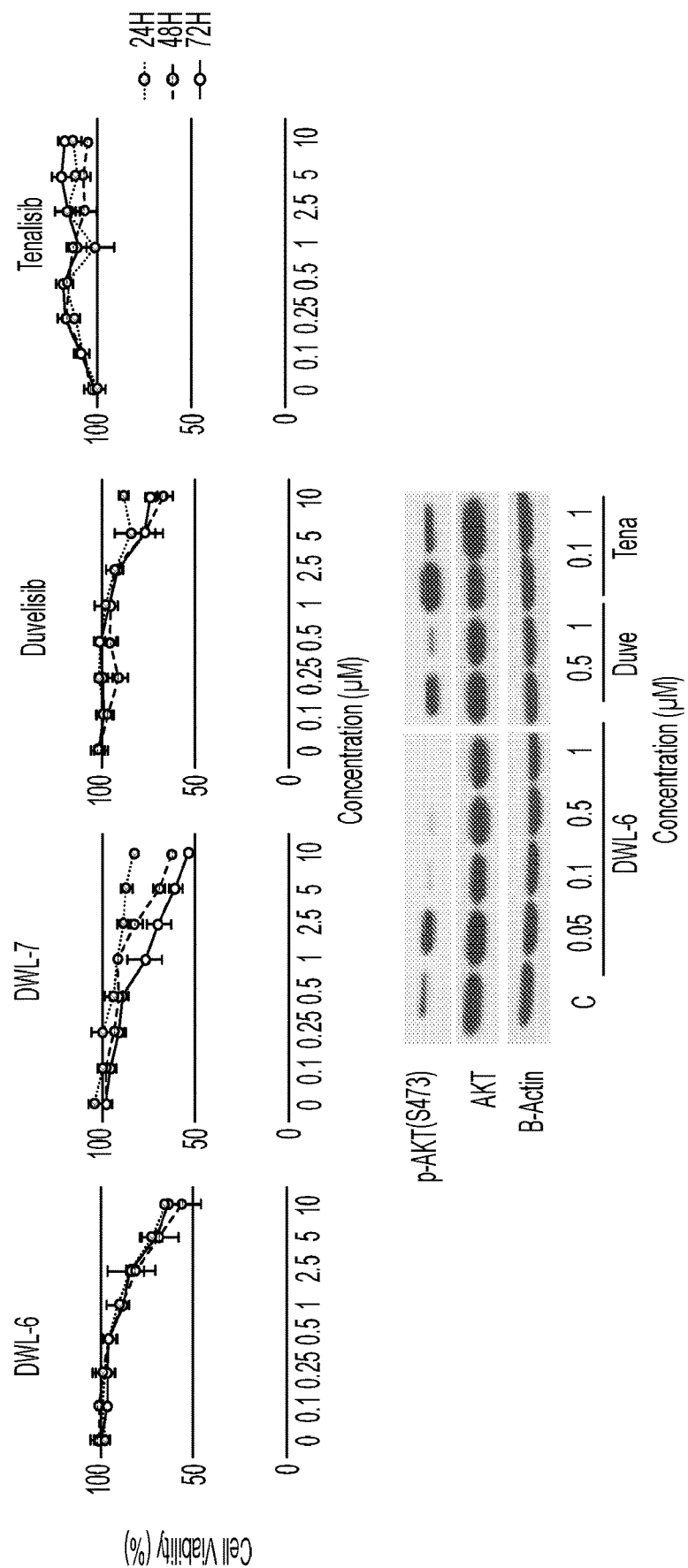
FIG. 20 compares results of a viability assay in T-ALL PF-382 cell line (CellTiter-Glo) for DWL-PI3K-6, DWL-PI3K-7, duvelisib, and tenalisib.

Mice with genetically induced T-ALL that express luciferase were treated with 10 mg/kg of compound DWL-PI3K-3 every 12 h for 7 days. Results are shown in FIGS. 16-17 demonstrating a significant reduction in tumor burden as evidenced by a loss of luciferin signal and reduction in Ki67/thy1.2 positive population after treatment.

The contents of all references, pending patent applications and published patents, cited throughout this application are hereby expressly incorporated by reference.

The foregoing embodiments are presented by way of example only. A person of ordinary skill in the relevant field would understand that various modifications may be made without deviating from the spirit and scope of the present invention.

The invention claimed is:
1. A compound of the following formula or salt thereof:

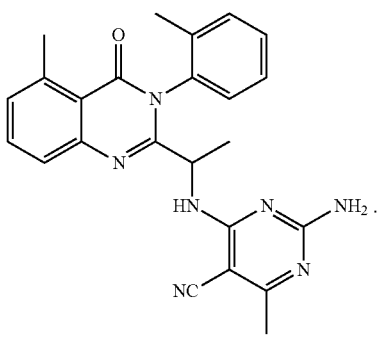 [SMILES: Cc1ccccc1-n1c(C(C)Nc2nc(N)nc(C)c2C#N)nc2cccc(C)c2c1=O]

2. The compound according to claim 1, wherein the compound is:

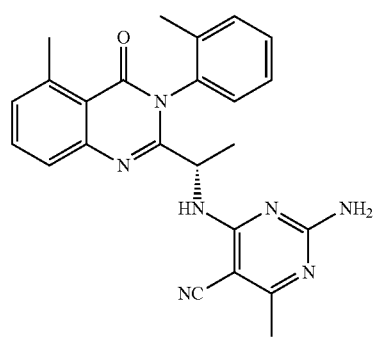 [SMILES: Cc1ccccc1-n1c([C@H](C)Nc2nc(N)nc(C)c2C#N)nc2cccc(C)c2c1=O]

or a salt thereof.

3. The compound according to claim 1, wherein the compound is an inhibitor of both PI3Kδ and PI3Kγ.

4. A pharmaceutical composition comprising a compound of claim 1 and a pharmaceutically acceptable carrier.

5. A pharmaceutical composition comprising a compound of claim 2 and a pharmaceutically acceptable carrier.

6. The compound according to claim 1, wherein the compound is in the form of a pharmaceutical composition, wherein the compound is a dual inhibitor of PI3Kδ and PI3Kγ.

7. A method for treating a non-Hodgkin's lymphoma comprising administering an effective amount of a compound of claim 1 to a subject in need thereof.

8. The method according to claim 7, wherein the non-Hodgkin's lymphoma is a T-cell lymphoma.

9. The method according to claim 8, wherein the T-cell lymphoma is peripheral T-cell lymphoma.

10. The method according to claim 7, further comprising co-administering to the subject at least one chemotherapeutic agent.

11. The method according to claim 10, wherein the chemotherapeutic agent is actinomycin, amsacrine, anthracycline, busulfan, cisplatin, cytoxan, epirubicin, hexamethylmelamineoxaliplatin, iphosphamide, mitoxantrone, teniposide, triethylenethiophosphoramide, hydrocortisone, cortisone, methylprednisolone, prednisolone, dexamethasone, prednisone, betamethasone, triamcinolone, beclometasone, fludrocortisone, deoxycorticosterone, aldosterone, oxaliplatin, zoledronic acid, ibandronate, verapamil, podophyllotoxin, carboplatin, procarbazine, mechlorethamine, cyclophosphamide, camptothecin, ifosfamide, melphalan, chlorambucil, bisulfan, nitrosourea, dactinomycin, daunorubicin, doxorubicin, bleomycin, plicomycin, mitomycin, etoposide (VP16), tamoxifen, transplatinum, 5-fluorouracil, vincristin, vinblastin, methotrexate, L-asparaginase, rapamycin, dibenzazepine (DBZ), uramustine, carmustine, lomustine, streptozocin, temozolomide, idarubicin, topotecan, pemetrexed, 6-mercaptopurine, darcarbazine, fludarabine, arabinosycytosine, arabinosylcytosine, capecitabine, gemcitabine, decitabine, vinca alkaloids, paclitaxel (TAXOL®), docetaxel (TAXOTERE®), ixabepilone (IXEMPRA®), or combinations thereof.

12. The method according to claim 11, wherein the chemotherapeutic agent is a glucocorticoid selected from the group consisting of hydrocortisone, cortisone, methylprednisolone, prednisolone, dexamethasone, prednisone, betamethasone, triamcinolone, beclometasone, fludrocortisones, deoxycorticosterone, aldosterone, and combinations thereof.

13. The method according to claim 12, wherein the chemotherapeutic agent is dexamethasone.

14. The method according to claim 7, wherein the compound is in the form of a pharmaceutical composition comprising an effective amount of the compound and a pharmaceutically acceptable carrier.

15. The method according to claim 14, wherein the composition is in a unit dosage form.

16. A method of treating a lymphoma or leukemia comprising administering an effective amount of a compound of claim 1 to a subject in need thereof.

17. The method of claim 16, wherein the lymphoma or leukemia is acute lymphoblastic leukemia (ALL), T cell acute lymphoblastic leukemia (T-ALL), B cell acute lymphoblastic leukemia (B-ALL), T cell lymphoma, peripheral T cell lymphoma (PTCL), cutaneous T cell lymphoma (CTCL), B cell lymphoma, follicular lymphoma, cutaneous B cell lymphoma, or chronic lymphocytic leukemia (CLL).

18. The method of claim 16, wherein the lymphoma or leukemia is T-ALL.

19. A method for treating a non-Hodgkin's lymphoma comprising administering an effective amount of a compound of claim 2 to a subject in need thereof.

20. The method according to claim 19, wherein the non-Hodgkin's lymphoma is a T-cell lymphoma.

21. The method according to claim 20, wherein the T-cell lymphoma is peripheral T-cell lymphoma.

22. The method according to claim 19, further comprising co-administering to the subject at least one chemotherapeutic agent.

23. The method according to claim 22, wherein the chemotherapeutic agent is actinomycin, amsacrine, anthracycline, busulfan, cisplatin, cytoxan, epirubicin, hexamethylmelamineoxaliplatin, iphosphamide, mitoxantrone, teniposide, triethylenethiophosphoramide, hydrocortisone, cortisone, methylprednisolone, prednisolone, dexamethasone, prednisone, betamethasone, triamcinolone, beclometasone, fludrocortisone, deoxycorticosterone, aldosterone, oxaliplatin, zoledronic acid, ibandronate, verapamil, podophyllotoxin, carboplatin, procarbazine, mechlorethamine, cyclophosphamide, camptothecin, ifosfamide, melphalan, chlorambucil, bisulfan, nitrosourea, dactinomycin, daunorubicin, doxorubicin, bleomycin, plicomycin, mitomycin, etoposide (VP16), tamoxifen, transplatinum, 5-fluorouracil, vincristin, vinblastin, methotrexate, L-asparaginase, rapamycin, dibenzazepine (DBZ), uramustine, carmustine, lomustine, streptozocin, temozolomide, idarubicin, topotecan, pemetrexed, 6-mercaptopurine, darcarbazine, fludarabine, arabinosycytosine, arabinosylcytosine, capecitabine, gemcitabine, decitabine, vinca alkaloids, paclitaxel (TAXOL®), docetaxel (TAXOTERE®), ixabepilone (IX-EMPRA®), or combinations thereof.

24. The method according to claim 23, wherein the chemotherapeutic agent is a glucocorticoid selected from the group consisting of hydrocortisone, cortisone, methylprednisolone, prednisolone, dexamethasone, prednisone, betamethasone, triamcinolone, beclometasone, fludrocortisones, deoxycorticosterone, aldosterone, and combinations thereof.

25. The method according to claim 24, wherein the chemotherapeutic agent is dexamethasone.

26. A method of treating a lymphoma or leukemia comprising administering an effective amount of a compound of claim 2 to a subject in need thereof.

27. The method of claim 26, wherein the lymphoma or leukemia is acute lymphoblastic leukemia (ALL), T cell acute lymphoblastic leukemia (T-ALL), B cell acute lymphoblastic leukemia (B-ALL), T cell lymphoma, peripheral T cell lymphoma (PTCL), cutaneous T cell lymphoma (CTCL), B cell lymphoma, follicular lymphoma, cutaneous B cell lymphoma, or chronic lymphocytic leukemia (CLL).

28. The method of claim 26, wherein the lymphoma or leukemia is T-ALL.

* * * * *